(12) United States Patent
Hirata

(10) Patent No.: US 8,400,500 B2
(45) Date of Patent: Mar. 19, 2013

(54) ENDOSCOPE WITH ALTERNATING IRRADIATE LIGHT

(75) Inventor: Yasuo Hirata, Tokyo (JP)

(73) Assignee: Olympus Corporation (JP)

( * ) Notice: Subject to any disclaimer, the term of this patent is extended or adjusted under 35 U.S.C. 154(b) by 1506 days.

(21) Appl. No.: 11/559,197

(22) Filed: Nov. 13, 2006

(65) Prior Publication Data

US 2007/0112247 A1    May 17, 2007

(30) Foreign Application Priority Data

Nov. 16, 2005   (JP) .............................. P2005-331574

(51) Int. Cl.
   *A61B 1/04* (2006.01)
   *A61B 1/06* (2006.01)
(52) U.S. Cl. .......................................... 348/68; 600/179
(58) Field of Classification Search .................. 348/68; 600/179
   See application file for complete search history.

(56) References Cited

U.S. PATENT DOCUMENTS

| | | | | |
|---|---|---|---|---|
| 6,796,939 B1 * | 9/2004 | Hirata et al. | .................. | 600/179 |
| 2002/0101566 A1 * | 8/2002 | Elsner et al. | .................. | 351/200 |
| 2006/0122619 A1 * | 6/2006 | Kablik et al. | .................. | 606/88 |

FOREIGN PATENT DOCUMENTS

| | | |
|---|---|---|
| JP | 61-121575 | 6/1986 |
| JP | 2-304413 | 12/1990 |
| JP | 4-036716 | 2/1992 |
| JP | 05-111460 | 5/1993 |
| JP | 05-184530 | 7/1993 |
| JP | 07-178046 | 7/1995 |
| JP | 9-215659 | 8/1997 |
| JP | 11-216113 | 8/1999 |
| JP | 11-216114 | 8/1999 |
| JP | 11-225952 | 8/1999 |
| JP | 11-281897 | 10/1999 |
| JP | 11-318806 | 11/1999 |
| JP | 2000-147389 | 5/2000 |
| JP | 2000-147615 | 5/2000 |
| JP | 2000-300514 | 10/2000 |
| JP | 2001-104249 | 4/2001 |
| JP | 2002-000562 | 1/2002 |
| JP | 2002-034911 | 2/2002 |
| JP | 2003-038424 | 2/2003 |
| JP | 2003-140030 | 5/2003 |

(Continued)

OTHER PUBLICATIONS

Office Action issued in counterpart Japanese Patent Application No. 2004-147507 dated Mar. 2, 2010 and English language translation.

(Continued)

*Primary Examiner* — Richard Torrente
(74) *Attorney, Agent, or Firm* — Ostrolenk Faber LLP

(57) ABSTRACT

An endoscope that has an insertion portion that is inserted into an interior of an object and an image pickup device that is provided in the insertion portion, and that observes the interior of the object via the image pickup device, includes: a first LED unit that is provided in the insertion portion and has an LED chip that is used to irradiate light into the interior of the object; a second LED unit that is provided in the insertion portion and has an LED chip that is used to irradiate light into the interior of the object; and an alternating conduction control unit that conducts power alternatingly to the first LED unit and the second LED unit.

7 Claims, 41 Drawing Sheets

FOREIGN PATENT DOCUMENTS

| | | |
|---|---|---|
| JP | 2003-334161 | 11/2003 |
| JP | 2004-065575 | 3/2004 |
| JP | 2005-118137 | 5/2005 |
| JP | 2005-177134 | 7/2005 |

OTHER PUBLICATIONS

Office Action issued in counterpart Japanese Patent Application No. 2005-331574 dated May 10, 2011 and English language translation.

Office Action issued by the Japanese Patent Office on Mar. 6, 2012 in connection with corresponding Japanese Patent Application No. 2005-331574.

Translation of Office Action issued by the Japanese Patent Office on Mar. 6, 2012 in connection with corresponding Japanese Patent Application No. 2005-331574.

* cited by examiner

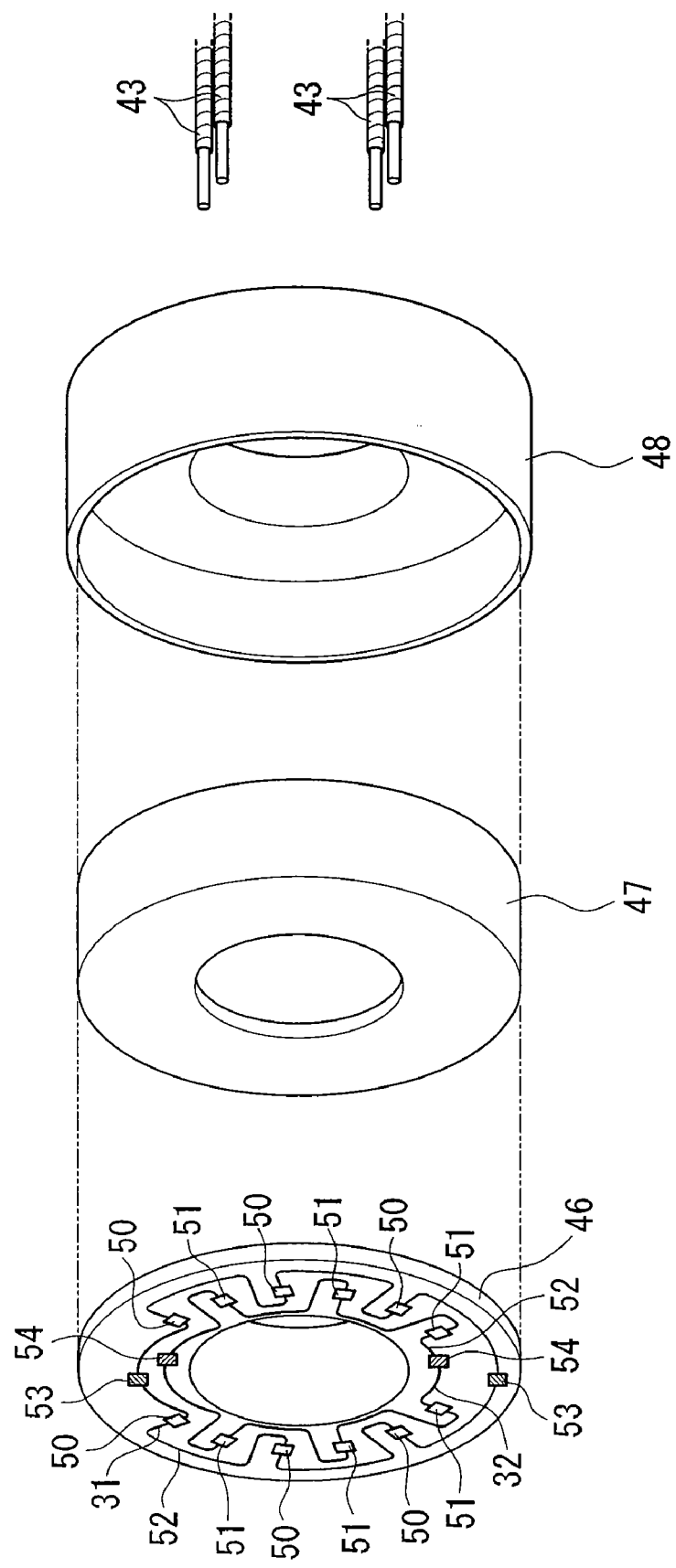

ENDOSCOPE WITH ALTERNATING IRRADIATE LIGHT

BACKGROUND OF THE INVENTION

1. Field of the Invention

The present invention relates to an endoscope that is used to observe an object.

Priority is claimed on Japanese Patent Application No. 2005-331574, filed Nov. 16, 2005, the contents of which are incorporated herein by reference.

2. Description of the Related Art

In recent years, endoscopes have been used in various fields such as the field of medicine and the field of industry in order to observe the interior of an object.

Of these endoscopes, those that are provided with a light emitting diode (referred to below as an LED) as an illumination device are well known (see, for example, Japanese Unexamined Patent Application, First Publication No. 2000-300514).

Endoscopes that are provided with an LED that irradiates illumination light and a CMOS sensor for obtaining an observation image are also known (see, for example, Japanese Unexamined Patent Application, First Publication No. 2002-562)

Furthermore, endoscopes that are provided with a CCD and LED at a distal end of an insertion portion of the endoscope and with a picture signal processing circuit to process signals output from the CCD are also known (see, for example, Japanese Unexamined Patent Application, First Publication No. H11-225952).

In addition, endoscopes that are provided with an LED and a temperature sensor to detect the temperature in the vicinity of the LED are also known (see, for example, Japanese Unexamined Patent Application, First Publication No. 2005-118137).

SUMMARY OF THE INVENTION

The endoscope of the present invention is provided with an insertion portion that is inserted into an interior of an object and an image pickup device that is provided in the insertion portion, and observes the interior of the object via the image pickup device. This endoscope includes: a first LED unit that is provided in the insertion portion and has an LED chip that is used to irradiate light into the interior of the object; a second LED unit that is provided in the insertion portion and has an LED chip that is used to irradiate light into the interior of the object; and an alternating conduction control unit that conducts power alternatingly to the first LED unit and the second LED unit.

In the endoscope of the present invention, it is preferable for the alternating conduction control unit to alternatingly switch conduction between the first LED unit and the second LED unit at regular time intervals.

It is preferable for the endoscope of the present invention to be further provided with a temperature detecting device that detects temperatures, and, when a detection signal from the temperature detecting device reaches a predetermined threshold value that has been set in advance, for the alternating conduction control unit to switch conduction to the first LED unit or the second LED unit.

In the endoscope of the present invention, it is preferable for the temperature detecting device to be provided adjacent to the LED chip.

It is preferable for the endoscope of the present invention to be further provided with: an acceleration detecting device that is provided in the insertion portion and detects a rate of acceleration of the insertion portion; and a simultaneous conduction control unit that conducts power simultaneously to the first LED unit and the second LED unit, and for the driving of the alternating conduction control unit or the simultaneous conduction control unit to be switched in accordance with an output from the acceleration detecting device.

In the endoscope of the present invention, it is preferable for the first LED unit to be provided with a plurality of first LED chips; for the second LED unit to be provided with a plurality of second LED chips; and for the first LED chips and the second LED chips to be placed in the insertion portion so as to alternate in the circumferential direction of the insertion portion.

It is preferable for the endoscope of the present invention to be further provided with a constant current supply device that is provided in the first LED unit and the second LED unit, and that supplies current of a fixed magnitude.

The endoscope of the present invention includes: an insertion portion that is inserted into an object; an illumination device that illuminates the object; an image pickup device that is provided in the insertion portion; a display device that displays an image that has been picked up by the image pickup device; a detecting device that detects a usage environment or a usage state of the insertion portion; and a brightness altering device that alters a brightness of an image that is displayed on the display device in accordance with a result of a detection by the detecting device.

It is preferable for the endoscope of the present invention to be further provided with an adaptor for an endoscope that is removably provided in the insertion portion, and for the detecting device to be provided in either the insertion portion or the endoscope adaptor.

In the endoscope of the present invention, it is preferable for the brightness altering device to be provided with a light amount adjusting device that adjusts an amount of light from the illumination device.

It is preferable for the endoscope of the present invention to be further provided with a diaphragm mechanism that adjusts an amount of reflection light from the object that enters into the insertion portion, and for the brightness altering device to be provided with a diaphragm control unit that controls the driving of the diaphragm mechanism.

It is preferable for the endoscope of the present invention to be further provided with a diaphragm mechanism that adjusts an amount of reflection light from the object that enters into the insertion portion. It is also preferable for the brightness altering device to be provided with: a light amount adjusting device that adjusts an amount of light from the illumination device; a diaphragm control unit that controls the driving of the diaphragm mechanism; and a joint control unit that jointly controls the light amount adjusting device in conjunction with the diaphragm control unit in accordance with a result of a detection by the detecting device.

In the endoscope of the present invention, it is preferable for the detecting device to be provided with a temperature sensor that detects a temperature around the illumination device.

In the endoscope of the present invention, it is preferable for the detecting device to be provided with a light amount sensor that detects an amount of reflection light from the object that enters into the insertion portion.

In the endoscope of the present invention, it is preferable for the detecting device to be provided with a distance sensor that detects a distance between the insertion portion and the object.

In the endoscope of the present invention, it is preferable for the detecting device to be provided with an acceleration sensor that detects a rate of acceleration of the insertion portion.

The endoscope of the present invention includes: an insertion portion that is inserted into an interior of an object; a first LED unit that is provided in the insertion portion and has an LED chip that is used to irradiate light into the interior of the object; a second LED unit that is provided in the insertion portion and has an LED chip that is used to irradiate light into the interior of the object; and an alternating conduction control unit that conducts power alternatingly to the first LED unit and the second LED unit; an image pickup device that is provided in the insertion portion; a display device that displays an image that has been picked up by the image pickup device; a detecting device that detects a usage environment or a usage state of the insertion portion; and a brightness altering device that alters a brightness of an image that is displayed on the display device in accordance with a result of a detection by the detecting device.

BRIEF DESCRIPTION OF THE DRAWINGS

FIG. 3 is an exploded perspective view showing a first LED unit and a second LED unit that are provided in the first embodiment of the endoscope of the present invention.

DETAILED DESCRIPTION OF THE INVENTION (First Embodiment)

The first embodiment of the endoscope of the present invention will now be described with reference made to FIG. 1A through 6.

Figure 1A:
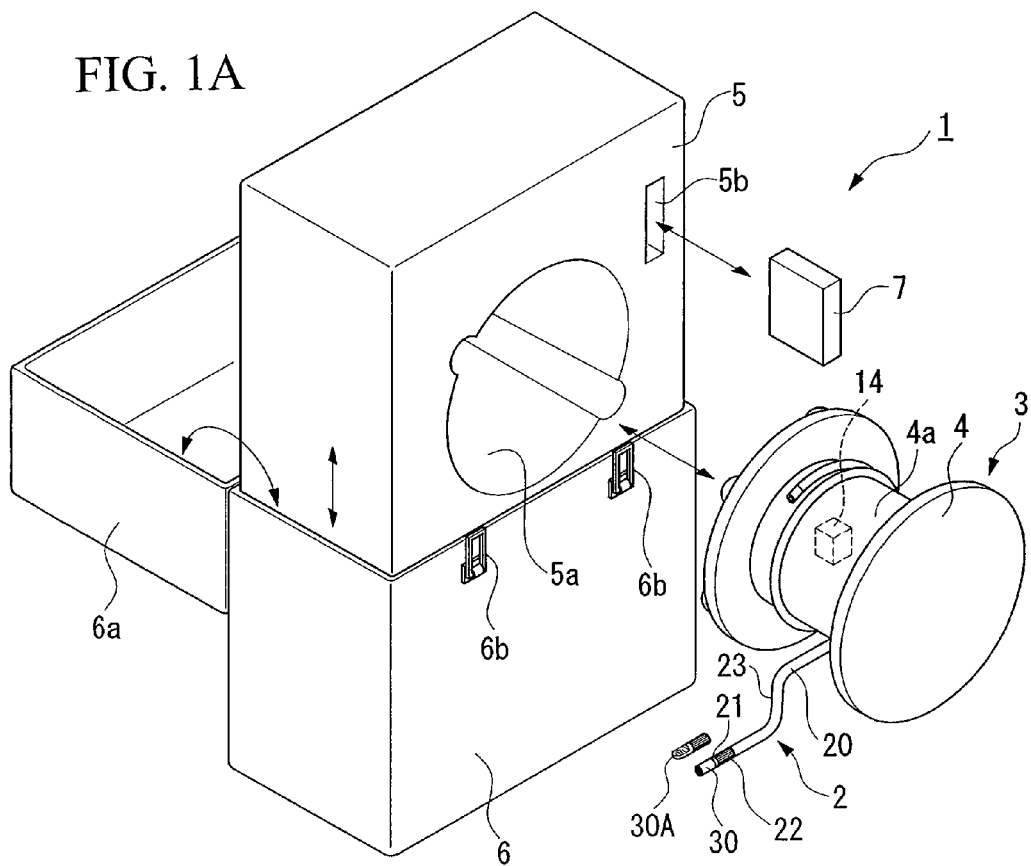
FIG. 1A is a view showing a first embodiment of the endoscope of the present invention, and is an exploded perspective view showing a state before the endoscope body is placed inside a case.
Figure 1B:
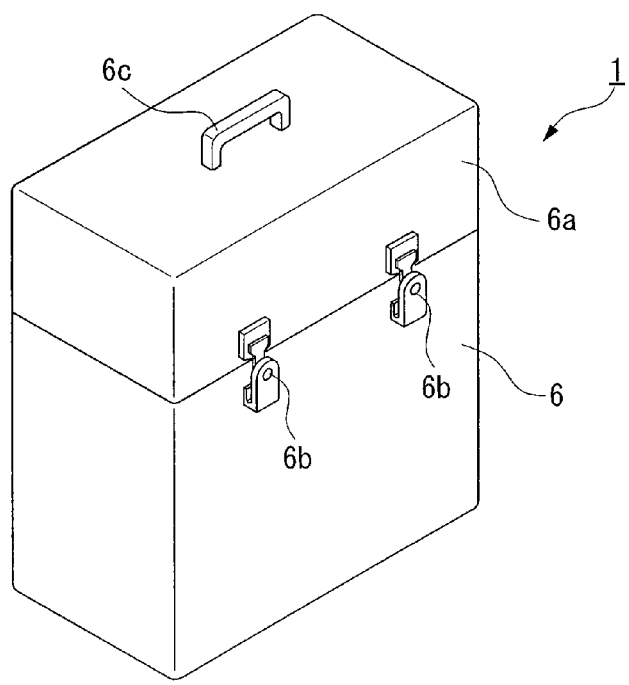
FIG. 1B is a view showing a first embodiment of the endoscope of the present invention, and is a perspective view showing a state when the endoscope body is placed inside the case.

FIG. 1A is an exploded perspective view showing a state before an endoscope body of an endoscope 1 of the present embodiment is placed inside a case, and FIG. 1B is a perspective view showing a state when this endoscope body is placed inside the case.

The endoscope 1 has as its principal component elements an endoscope body 3 that is provided with a narrow elongated insertion portion 2, and a drum portion 4 onto which the insertion portion 2 of the endoscope body 3 is wound and stored. The endoscope body 3 is held by being inserted into a concave housing position 5a of a housing portion 5 that is made of a cushioning material with the insertion portion 2 wound onto the drum portion 4. The endoscope body 3 is then stored inside a case 6 together with the housing portion 5, and may be transported. Note that the symbol 5b in the drawings shows a concave housing portion that is used to house an adaptor case 7, the symbol 6a is an opening and closing lid that is mounted via hinges on the case 6, the symbols 6b are clasps, and 6c is a handle.

The drum 4 is formed in the shape of a bobbin, for example, having disk-shaped flanges attached to the top and bottom of a cylindrical winding portion 4a onto which the insertion portion 2 is wound. The drum portion 4 is provided with an image display device such as an LCD monitor (not shown) that is positioned at a suitable location (for example, a flange or the like). Furthermore, a battery housing portion (not shown) that houses a power supply 40 (see FIG. 5) in the form of battery and a control unit (i.e., an alternating conduction control unit) 14 that performs a variety of controls are also provided inside the winding portion 4a.

In addition, a remote controller (not shown) of an operating section that is provided with a joystick that is used to perform a bend operation of the insertion portion 2 is connected via an operating cable to the drum portion 4.

Furthermore, this insertion portion 2 is provided with a tube-shaped flexible tube portion 20 and an optical adaptor 30 that is used to obtain an observation image. The optical adaptor 30 is removably fitted onto a distal end of the flexible tube portion 20.

The flexible tube 20 is equipped with a distal end hard portion 21 that is provided at the distal end of the flexible tube portion 20, a bending portion 22 that is used to orient a distal end surface of the optical adaptor 30 so that it faces in a predetermined observation direction, and a flexible portion 23 that is long and bendable and is connected to the distal end hard portion 21 and the bending portion 22. The bending portion 22 is provided at a position slightly to the rear of the distal end hard portion 21 and is provided with a plurality of fluid pressure actuators for performing a bending operation. Note that a non-combustible gas such as, for example, carbon dioxide, freon, nitrogen, helium, and argon is used for the operating fluid for a bending operation.

Figure 2A:
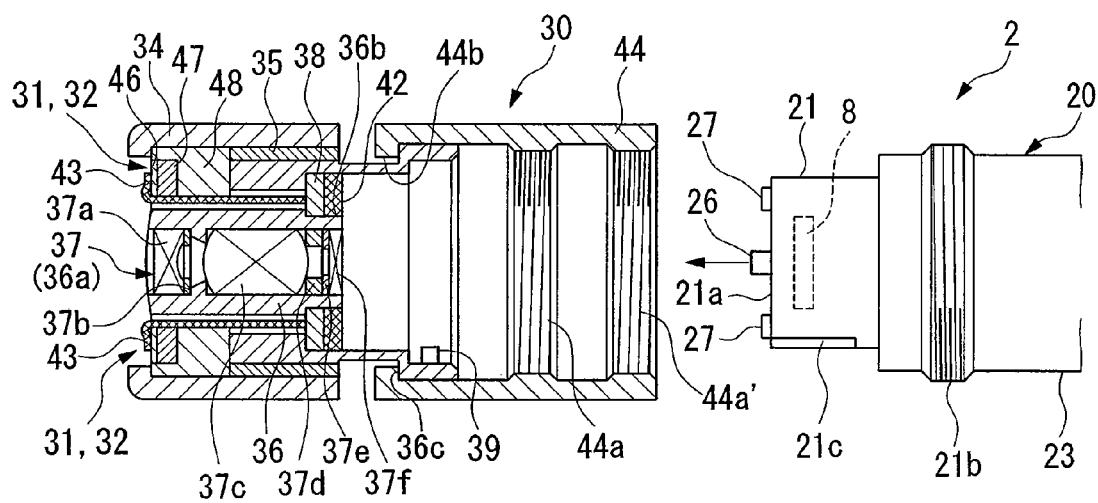
FIG. 2A is a side view of an insertion portion of the first embodiment of the endoscope of the present invention, and is a side cross-sectional view of an optical adaptor that is fitted into a distal end of the insertion portion.

As is shown in FIG. 2A, first protruding electrodes 26 and second protruding electrodes 27 that protrude in a longitudinal direction from a distal end surface 21a of the distal end hard portion 21 are provided on this distal end surface 21a. A pair of the first protruding electrodes 26 and a pair of the second protruding electrodes 27 are provided. When the optical adaptor 30 is attached to the distal end of the flexible tube portion 20, the first protruding electrodes 26 and the second protruding electrodes 27 are in contact with predetermined positions of the optical adaptor 30 and supply power to the optical adaptor 30.

Furthermore, a male threaded portion 21b that is used to attach the optical adaptor 30 is formed on an outer circumferential surface of the distal end hard portion 21. A key groove 21c that extends in the longitudinal direction of the insertion portion 2 is also formed on the outer circumferential surface of the distal end hard portion 21 to act as a positioning device during the attachment of the optical adaptor 30.

An image pickup device in the form of, for example, a CCD camera 8, is incorporated within the distal end hard portion 21 of the insertion portion 2 in order to pick up images that are acquired from the optical adaptor 30. The CCD 8 is connected via an image pickup cable (not shown) that is laid inside an internal space of the insertion portion 2 to the endoscope body 3. The CCD 8 is supplied with power from inside the drum portion 4 shown in FIG. 1A and transmits image signals that have been picked up. Note that the aforementioned observation device is not limited to the CCD camera 8 and may also be a C-MOS or an image guide fiber or the like.

As is shown in FIG. 2A, the optical adaptor 30 is formed by joining together a cylinder-shaped outer frame member 34 and a connecting ring 44.

A first LED unit 31 and a second LED unit 32 are placed inside a distal end portion of the outer frame member 34. In addition, by inserting an LED fixing portion 35 and an LED holder 36 through an aperture portion on the rear end side of the outer frame member 34, the first LED unit 31 and the second LED unit 32 are fixed inside the outer frame member 34. An objective lens group 37 that forms an optical lens system is provided in a space portion 36a that is formed extending along the axial center of the LED holder 36. In the example in the drawings, the objective lens group 37 is constructed having a first lens 37a, a spacer 37b, a second lens 37c, a spacer 37d, a diaphragm 37e, and a third lens 37f lined up in the axial direction in this sequence from the distal end side of the outer frame member 34.

An electrode substrate 38 and a conductive rubber 42 that is formed by an anisotropic elastic member are inserted in this sequence from the distal end surface side at an outer circumferential surface side of an inner cylinder portion 36b of the LED holder 36 that forms the space portion 36a.

Figure 2B:
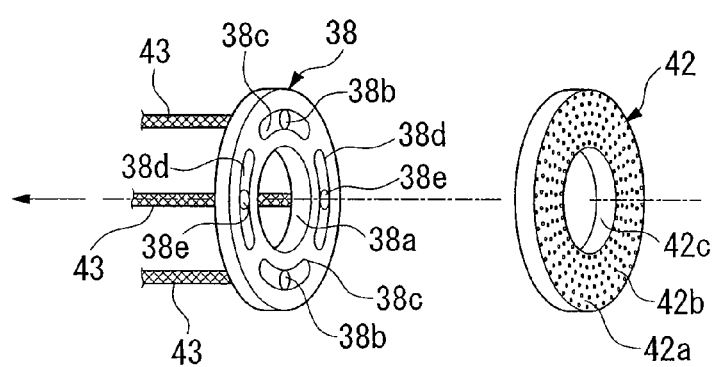
FIG. 2B is a perspective view as seen from an obliquely rearward direction of an electrode substrate and conductive rubber that are provided in the first embodiment of the endoscope of the present invention.

As is shown in FIG. 2B, the electrode substrate 38 is formed in a donut shape having a through hole 38a provided in the center portion of a circular resin substrate (referred to below as a circular plate) in order to make positioning easier. A vertical pair of first through holes 38b and a horizontal pair of second through holes 38e that each have a conductive body coated on their inner circumferential surfaces are provided around the through hole 38a. Electric wires 43 that supply power for illumination to the first LED unit 31 and the second LED unit 32 are electrically connected by soldering or the like to the first through holes 38b and the second through holes 38e. In addition, the electric wires 43 are each connected to the first LED unit 31 and the second LED unit 32.

Moreover, a vertical pair of first electrode patterns 38c that are made conductive with the conductive body that is coated on the inner circumferential surfaces of the first through holes 38b, and a left and right pair of second electrode patterns 38d that are in a conductive state in the interior of the substrate are each independently provided in the rear end surface of the electrode substrate 38.

One of the first electrode patterns 38c is provided independently for each of the pair of first through holes 38b. In other words, the pair of first electrode patterns 38c are separated from each other so that short circuiting between them does not occur, and each one is formed in an arc shape. Moreover, one of the second electrode patterns 38d is provided independently for each of the pair of second through holes 38e and each one is formed in an arc shape.

The aforementioned conductive rubber 42 is formed by an elastic body 42a, which is a non-conductive member, in which a number of conductive members 42b have been arranged in a dot formation. This conductive rubber 42 is also known as, for example, a dot type of anisotropic rubber. In the conductive rubber 42, conductive members 42b such as nickel grains or metal grains that have been gold plated are arranged in the thickness direction of, for example, an elastic body 42a that is made by forming silicon rubber or the like into a sheet shape. Accordingly, by lightly pressing the conductive rubber 42 in the thickness direction thereof, the conductivity between the densely arrayed conductive members 42b is improved, and excellent conductivity in this thickness direction can be obtained. However, because the elastic body 42a is a non-conductive member, a non-conductive state remains in directions other than the thickness direction of the conductive rubber 42 (for example, the circumferential direction). In this case, the respective conductive members 42b that are arranged in a dot shape (i.e., the shape on both exposed surfaces is a dot shape) are separated into members that are insulated from each other and are placed in a non-conductive independent state.

Moreover, in the same manner as for the above described electrode substrate 38, the conductive rubber 42 is also formed in a donut shape by providing a through hole 42c in a center portion thereof in order to make positioning easier.

Note that in the above described embodiment a dot type of conductive rubber 42 is employed in which the conductive members 42b are arranged in a dot shape, however, in addition to this, it is also possible to use, for example, a stripe type of conductive rubber.

In a stripe type of conductive rubber, the conductive members that are arranged in rows in the thickness direction are placed in a stripe configuration in an elastic body which is a non-conductive member. In this case, the respective conductive members that are arranged in a stripe shape (i.e., the shape of exposed portions of both surfaces and of the respective cross-sections are in a stripe shape) are separated into members that are insulated from each other and are in an independent state. Note that, provided that they are separated from each other, the layout direction and layout shape (i.e., they may be laid out in parallel or the like) of the stripe shaped conductive members is not particularly restricted.

Moreover, a protruding portion 39 that engages with a key-shaped groove in the insertion portion 2 is provided in an inner circumferential surface at a rear end side of the LED holder 36, and a substantially cylinder-shaped connecting ring 44 is provided on the outer circumferential surface thereof. Namely, as a result of the LED holder 36 being inserted into the connecting ring 44 and an anchoring portion 44b that is provided at a distal end of the connecting ring 44 being engaged with a step portion 36c of the LED holder 36, the connecting ring 44 is supported such that it is able to rotate but is not able to be withdrawn in the axial direction. An inner threaded portion 44a that meshes with the male threaded portion 21b of the insertion member 2 is formed in the inner circumferential surface of the connecting ring 44. Furthermore, an inner threaded portion 44a' that prevents the connecting ring 44 falling off the insertion portion 2 is provided at a rear end side of the inner threaded portion 44a.

On the basis of the above described structure, if the optical adaptor 30 is attached to the distal end of the distal end hard portion 21, the protruding portion 39 engages with the key groove 21c so that the relative rotation position of the optical adaptor 30 relative to the insertion portion 2 is set. As a result, the first protruding electrodes 26 and the second protruding electrodes 27 are in contact with predetermined positions of the conductive rubber 42, and power is supplied to a predetermined first LED unit 31 and second LED unit 32.

In addition to a direct view type of optical adaptor 30 that has an LED illumination source provided in its distal end surface, there is also, for example, as is shown in FIG. 1A, a side view type of optical adaptor 30A that has an observation window and an LED illumination source provided in a side surface (i.e., circumferential surface) thereof, and an adaptor in which the optical specifications can be changed by changing the structure of the subjective lens group 37.

Furthermore, the endoscope 1 of the present embodiment is provided with the first LED unit 31 and the second LED unit 32 inside the optical adaptor 30. As is shown in FIG. 3, the first LED unit 31 and the second LED unit 32 are provided at a distal end surface of a cylinder-shaped flexible substrate 46.

The first LED unit 31 is provided with a plurality of first LED chips (i.e., LED chips) 50 and with a first pattern 53 that is used to supply current to the first LED chips 50. The first LED chips 50 are electrically connected via wires 52 to the first pattern 53. In the same way, the second LED unit 32 is provided with a plurality of second LED chips (i.e., LED chips) 51 and with a second pattern 54 that is used to supply current to the second LED chips 51. The second LED chips 51 are electrically connected via wires 52 to the second pattern 54.

Furthermore, the first LED chips 50 and the second LED chips 51 are arranged in parallel with each other in the circumferential direction of the flexible substrate 46. Accordingly, each of the wires 52 is arranged in a zigzag such that they do not come into contact with each other. In addition, a first pattern 53 and a second pattern 54 are placed at both the top and bottom such that the first LED chips 50 and the second LED chips 51 are divided into blocks that each have the same number of LED chips. Namely, in the present embodiment, the first LED chips 50 and the second LED chips 51 are set such that three of each are arranged in a straight line in two parallel rows.

Figure 4:
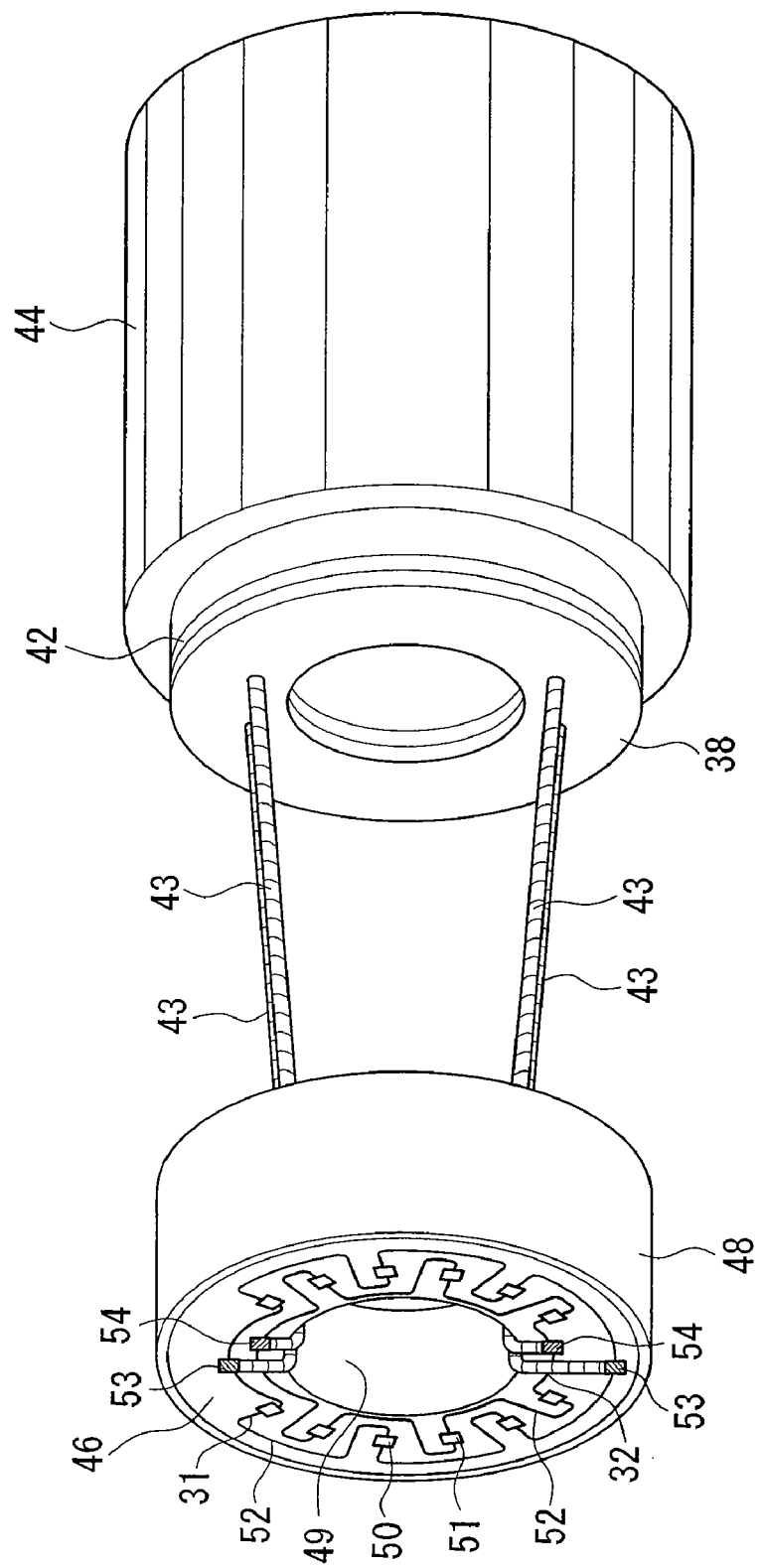
FIG. 4 is a perspective view showing a state in which electric wires are connected to the first LED unit and the second LED unit that are provided in the first embodiment of the endoscope of the present invention.

The flexible substrate 46 is attached to a distal end surface of a cylinder-shaped LED case 48 via an aluminum substrate 47. As is shown in FIG. 4, when the flexible substrate 46 is attached, the electric wires 43 that extend from the electrode substrate 38 pass from the rear end side of the LED case 48 into a cavity portion 49 that is formed in the center of the flexible substrate 46. The electric wires 43 are further bent at the distal end of the flexible substrate 46 and are each connected to the first pattern 53 and the second pattern 54. As a result, current from the first protruding electrodes 26 and the second protruding electrodes 27 is supplied to each first LED chip 50 and second LED chip 51 via the electric wires 43.

Figure 5:
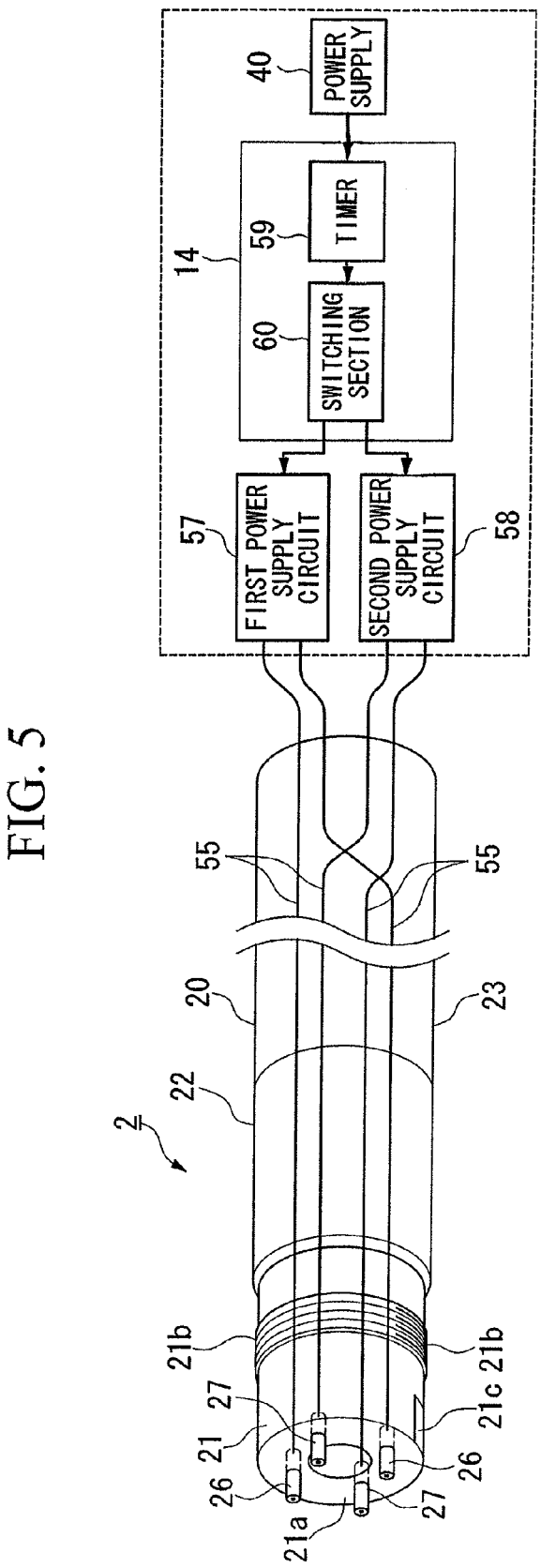
FIG. 5 is a system diagram of the power supply of the insertion portion of the first embodiment of the endoscope of the present invention.
Figure 6:
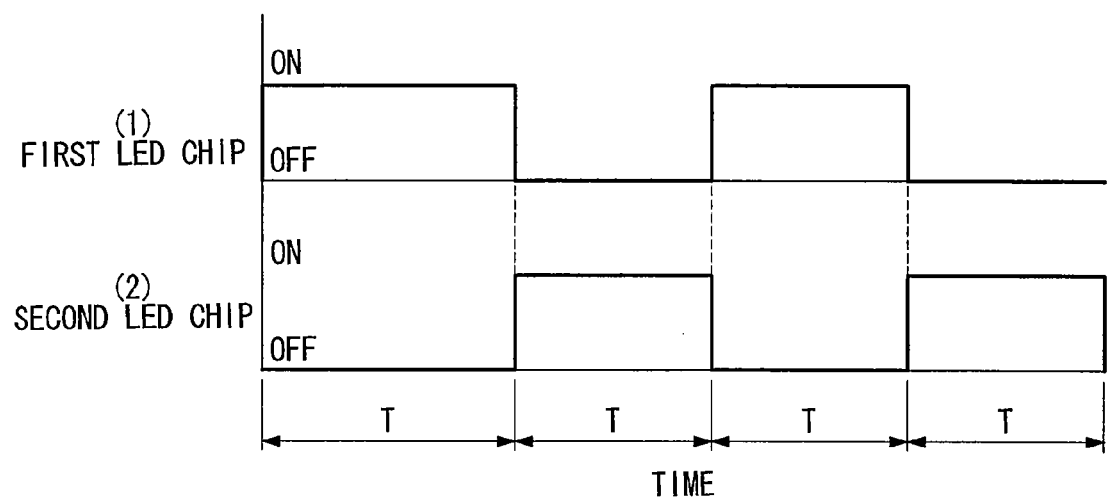
FIG. 6 is a time chart showing relationships between elapsed time and drive states of a first LED chip and a second LED chip that are provided in the first embodiment of the endoscope of the present invention.
Figure 7A:
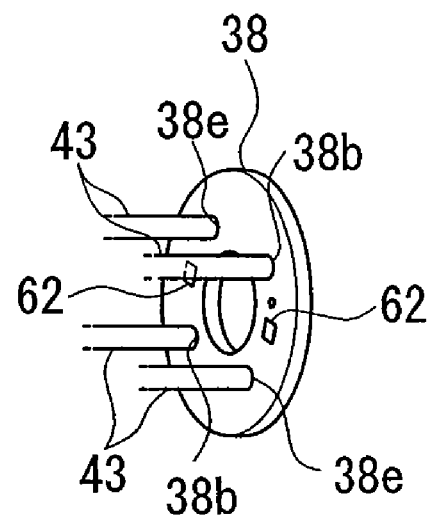
FIG. 7A is a perspective view as seen from an obliquely forward direction of an electrode substrate that is provided in the second embodiment of the endoscope of the present invention.
Figure 7B:
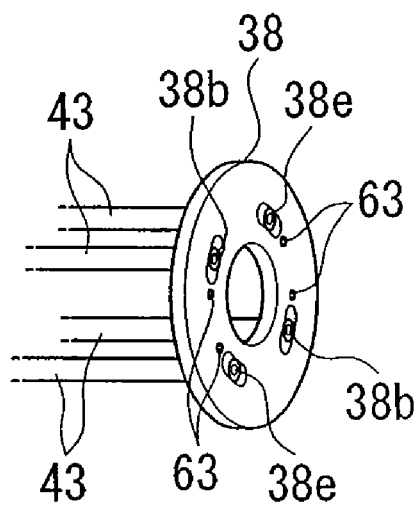
FIG. 7B is a perspective view as seen from an obliquely rearward direction of an electrode substrate that is provided in the second embodiment of the endoscope of the present invention.

Moreover, as is shown in FIG. 5, the first protruding electrodes 26 and the second protruding electrodes 27 are each electrically connected via a cable 55 to a first power supply circuit (i.e., constant current supply device) 57 and a second power supply circuit (i.e., constant current supply device) 58. The first power supply circuit 57 and the second power supply circuit 58 supply current of a fixed magnitude, and are connected to the above described control unit 14. The control unit 14 is provided with a switching section 60 that is connected to the first power supply circuit 57 and the second power supply circuit 58, and a timer 59 that outputs switching signals at fixed time intervals.

On the basis of the above described structure, the first power supply circuit 57 and the second power supply circuit 58 are driven alternatingly at fixed time intervals by the switching section 60 in accordance with switching signals from the timer 59.

Next, an operation of the endoscope 1 of the present embodiment that has the above described structure will be described.

Firstly, the desired optical adapter 30 is selected and the distal end of the flexible tube portion 20 is inserted through the rear end side aperture of the connecting ring 44 thereof. Next, the connecting ring 44 is rotated so that the optical adapter 30 and the flexible tube portion 20 are joined together. At this time, the male threaded portion 21b of the distal end hard portion 21 meshes at first with the inner threaded portion 44a' of the connecting ring 44, however, by further rotating the connecting ring 44, the male threaded portion 21b moves across the inner threaded portion 44a' towards the distal end portion side and becomes unmeshed. As a result, because the male threaded portion 21b is positioned between the pair of threaded portions 44a and 44a' that have a predetermined gap between them and is able to move freely, the inner threaded portion 44a' anchors the male threaded portion 21b and functions as a stopper to prevent the optical adapter 30 dropping off the flexible tube portion 20.

If the connecting ring 44 is further rotated so as to push in the insertion portion 2 from this locked position, the male threaded portion 21b meshes with the inner threaded portion 44a on the distal end side, with the key groove 21c and the protruding portion 39 in an engaged state. Therefore, the optical adapter 30 is joined to the distal end portion of the insertion portion 2, with the optical adapter 30 being fixed at a predetermined position. In addition, when the optical adapter 30 is joined at a predetermined position, the distal end of the first protruding electrode 26 and the distal end of the second protruding electrode 27 come into contact with the conductive rubber 42, and this conductive rubber 42 is pressed in the direction of the distal end of the optical adapter 30 and is compressed. Because of this, the conductivity of the conductive members 42b that are arrayed in the thickness direction of the conductive rubber 42 is improved due to their high density, and the conductive members 42b are placed in a conductive state.

At this point, as is described below, power is supplied to the first LED unit 31 or the second LED unit 32, and the first LED chips 50 or the second LED chips 51 are made to emit light. The insertion portion 2 is then gradually inserted inside an object and light is irradiated inside the object. At this time, reflection light from the interior of the object forms an image on the CCD 8 via the subjective lens group 37, and an image signal from the CCD 8 is displayed by predetermined processing on a monitor. The object can then be examined by observing the observation image on the monitor.

Here, the temperature inside the optical adapter 30 rises due to the emitted light from the first LED chips 50 or the second LED chips 51, however, in the endoscope 1 of the present embodiment, any excessive rise in temperature is prevented in the following manner.

Namely, if a switch is turned on and power is supplied from the power supply 40 to the timer 59, a switching signal is output from the timer 59, and this switching signal is input into the switching section 56. Based on this switching signal, the switching section 56 drives the first power supply circuit 57. Consequently, constant current is supplied from the first power supply circuit 57 via the cable 55 to the first protruding electrodes 26, and this constant current arrives at the first pattern 53 via the conductive rubber 42, the electrode substrate 38, and the electric wires 43. The constant current is then supplied from here to each of the first LED chips 50. As a result, each of the first LED chips 50 emits light and the interior of the object is illuminated.

The temperature inside the optical adapter 30 gradually rises because of the light and heat generated by the first LED chips 50, however, once the predetermined time T (shown in FIG. 6) from the driving of the first power supply circuit 57 has lapsed, a switching signal is output by the timer 59. Based on this switching signal, the switching section 56 stops the driving of the first power supply circuit 57. At the same time, the second power supply circuit 58 is driven and constant current is supplied to the second LED chips 51. The second LED chips 51 then emit light.

Furthermore, when the predetermined time T has elapsed, at the same time as the driving of the second power supply circuit 58 is stopped, the first power supply circuit 57 is driven, and this alternate driving at fixed time intervals is repeated. As a result, the temperature that had initially been raised by the light and the heat emitted from the first LED chips 50 is lowered as a result of the switch to the second LED chips 51. However, the temperature that had temporarily dropped is once again raised by the light and heat emitted from the second LED chips 51. This raised temperature is also again lowered by the switching to the cooled LED chips 50 once a predetermined time has elapsed.

By repeating these actions, the temperature inside the optical adapter 30 is adjusted to so as not to increase and exceed a predetermined temperature.

As is described above, according to the endoscope 1 of the present embodiment, by switching alternatingly between a light emission from the first LED chips 50 and a light emission from the second LED chips 51, it is possible to suppress any excessive heat generation from the first LED chips 50 and the second LED chips 51, and it is possible to suppress any temperature increase inside the optical adapter 30.

Moreover, by suppressing any excessive temperature increase, not only is it possible to improve the durability of the first LED chips 50 and the second LED chips 51, but it is also possible to inhibit any adverse effects on an observation image.

Furthermore, by placing the first LED chips 50 and the second LED chips 51 alternatingly in the circumferential direction of the flexible substrate 46, light can be irradiated uniformly on an object being examined, and a clear observation image with little unevenness in brightness can be obtained.

Moreover, as a result of constant current being supplied by the first power supply circuit 57 and the second power supply circuit 58, the brightness of the first LED chips 50 and the second LED chips 51 is kept constant. Because of this, it is possible to irradiate light of a uniform brightness onto an object being examined, and a clear observation image with little flickering can be obtained.

(Second Embodiment)

The second embodiment of the present invention will now be described with reference made to FIG. 7A through FIG. 10. In FIG. 7A through FIG. 10, component elements that have the same structure as those described in FIG. 1 through FIG. 6 are given the same symbols and a description thereof is limited.

The basic structure of the present embodiment is the same as that of the first embodiment, however, it differs in the following points.

Namely, in the present embodiment, a pair of temperature sensors (i.e., temperature detecting devices) 62 that have a predetermined resistance built into them are provided in the electrode substrate 38. These temperature sensors 62 are provided on a distal end surface of the electrode substrate 38 so as to be close to the first LED chips 50 and the second LED chips 51. When a predetermined current is supplied to the temperature sensors 62, a voltage that corresponds to the surrounding temperature is applied thereto. An electrode 63 for the sensor on the substrate side that is electrically connected to the temperature sensors 62 is provided at a rear end surface of the electrode substrate 38.

Figure 8:
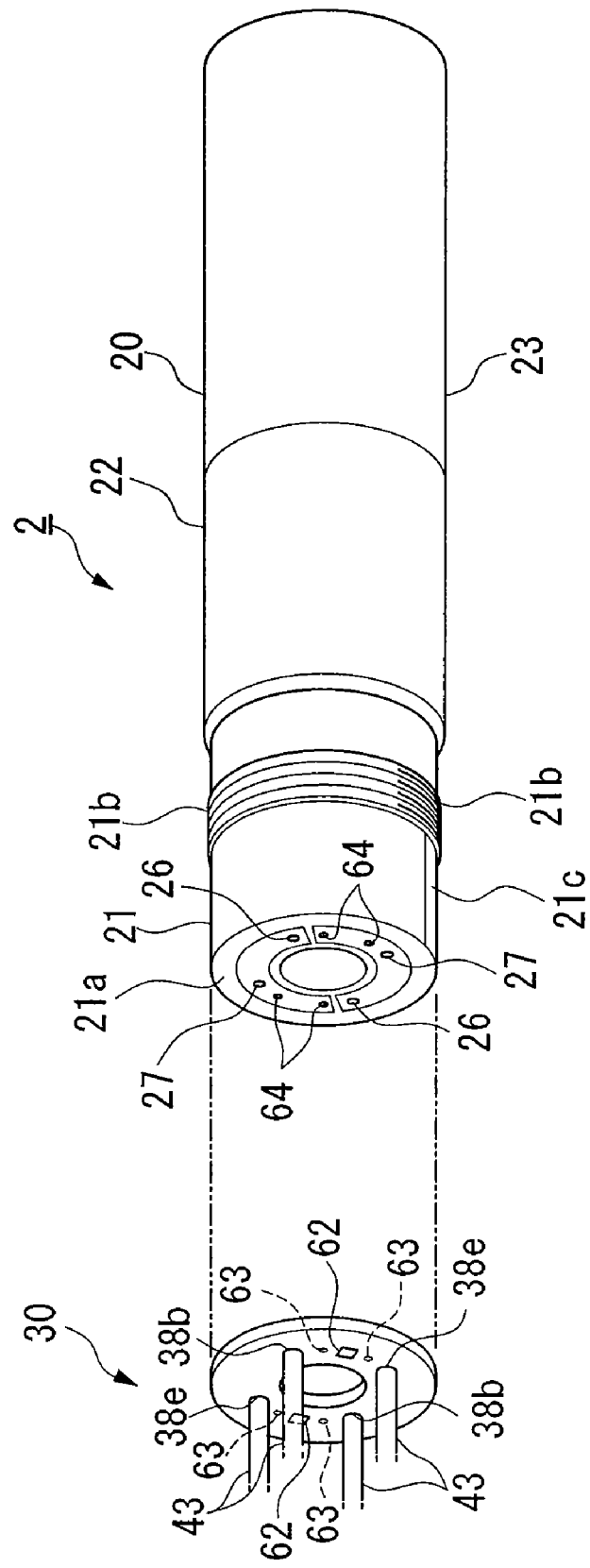
FIG. 8 is a perspective view showing a distal end of an insertion portion of the second embodiment of the endoscope of the present invention.

Moreover, in the present embodiment, as is shown in FIG. 8, in addition to the first protruding electrodes 26 and the second protruding electrodes 27, an electrode 64 for the sensor on the flexible tube portion side is provided on a distal end surface 21a of the distal end hard portion 21 so as to face the substrate side sensor electrode 63. In addition, when the optical adapter 30 is attached to the flexible tube portion 20, the substrate side sensor electrode 63 and the flexible tube side sensor electrode 64 are able to conduct power to each other via the conductive rubber 42.

Figure 9:
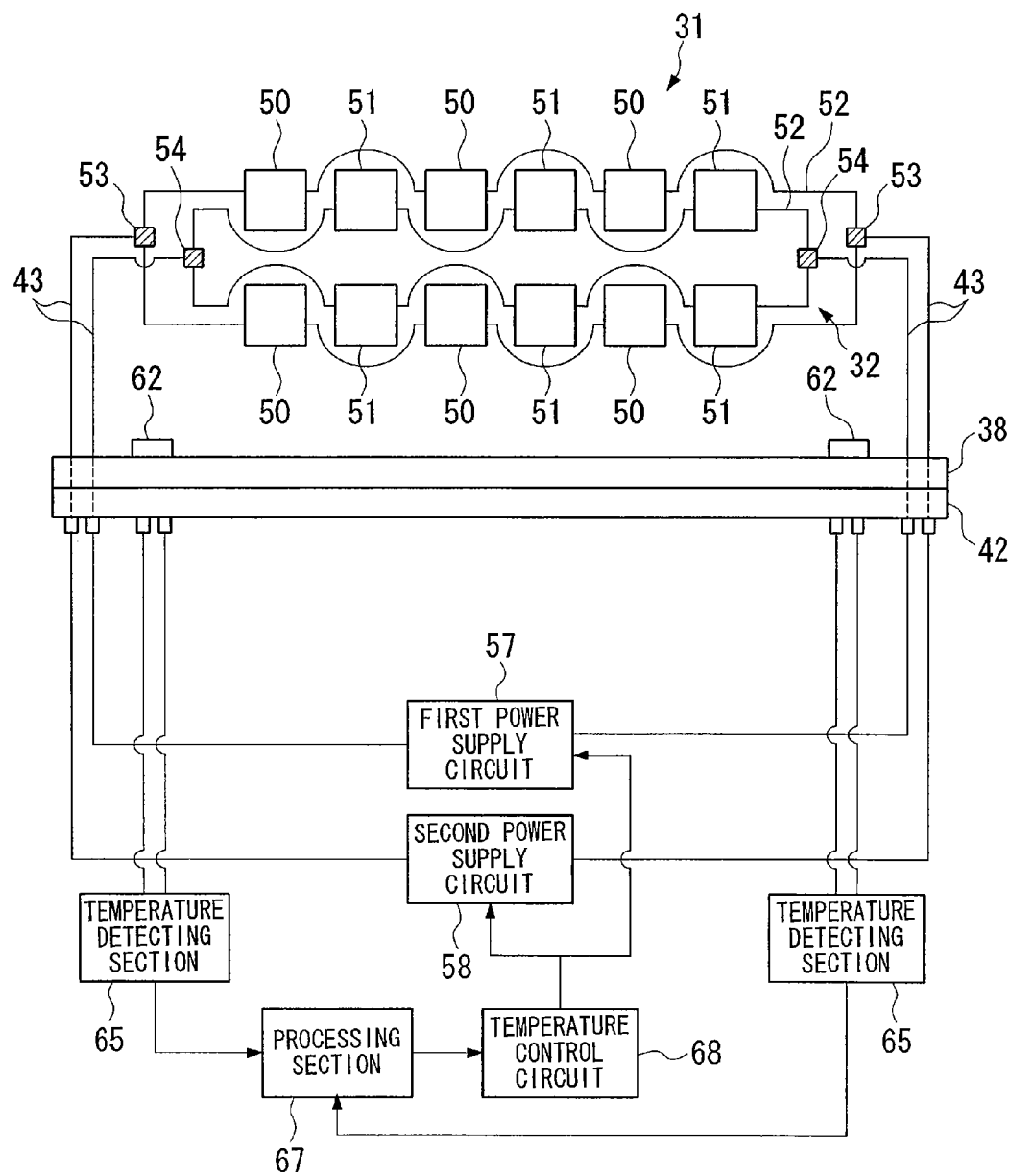
FIG. 9 is a system diagram of the power supply of a first LED unit and a second LED unit that are provided in the second embodiment of the endoscope of the present invention.

Furthermore, in the present embodiment, as is shown in FIG. 9, there are also provided temperature detecting sections (i.e., temperature detecting devices) 65 that are electrically connected to the respective temperature sensors 62, a processing section 67 that calculates an average value of the detection results from the respective temperature detecting sections 65, and a temperature control circuit (i.e., an alternating conduction control unit) 68 that compares this average value (i.e., the calculated result from the processing section 67) with a threshold value $\theta_1$ that has been set in advance (shown in FIG. 10) and switches between driving the first power supply circuit 57 and the second power supply circuit 58.

On the basis of the above described structure, the temperature surrounding the temperature sensors 62 is detected by the respective temperature sensors 62 and temperature detecting sections 65, and the respective detection results are input into the processing section 67.

Figure 10:
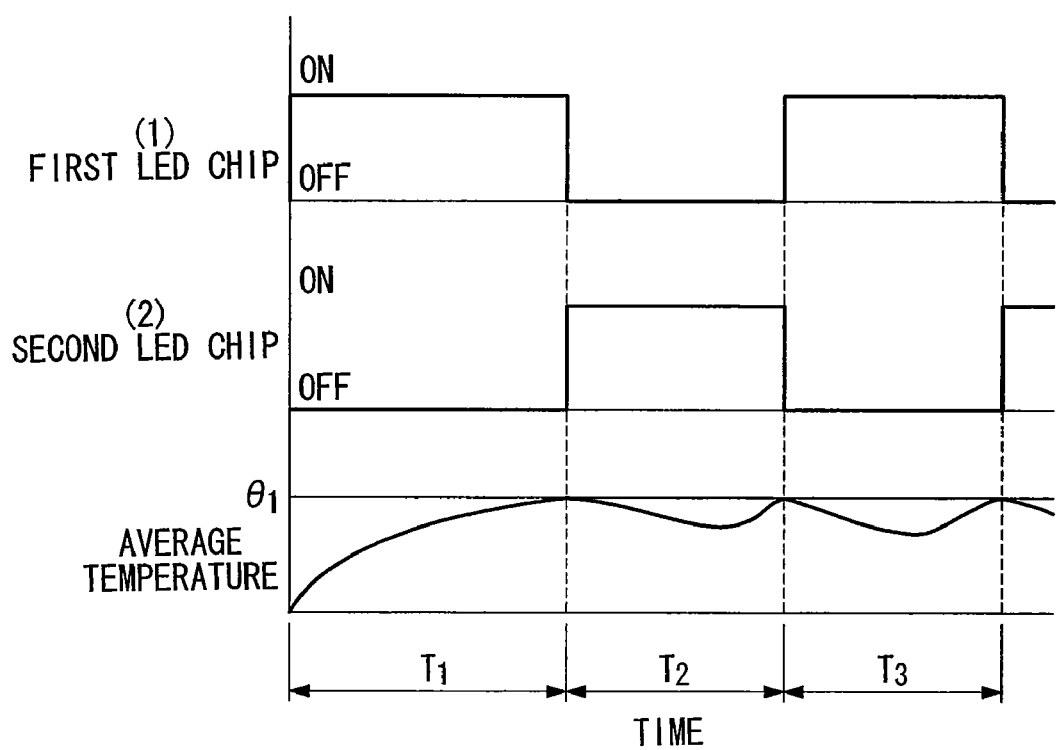
FIG. 10 is a time chart showing relationships between elapsed time and the temperature inside an optical adaptor as well as drive states of a first LED chip and a second LED chip that are provided in the second embodiment of the endoscope of the present invention.

The processing section 67 calculates an average value of both temperatures from the respective detection results, and outputs this calculation result to the temperature control circuit 68. The temperature control circuit 68, as is shown in FIG. 10, compares the input average value with the preset threshold value $\theta_1$, and when the average value reaches the threshold value $\theta_1$, switches between driving the first power supply circuit 57 and driving the second power supply circuit 58. As a result, the driving of the first LED chips 50 or the second LED chips 51 is switched. Consequently, the temperature inside the optical adapter 30 is prevented from rising and exceeding the threshold value $\theta_1$.

As a result of the above, by using the temperature sensors 62 and of the temperature detecting sections 65, the heat generated by the first LED chips 50 and the second LED chips 51 can be controlled accurately and reliably, and it is possible to suppress any increase in the temperature inside the optical adapter 30.

Moreover, by providing the temperature sensors 62 beside the first LED chips 50 and the second LED chips 51, the temperature sensors 62 are positioned close to the first LED chips 50 and the second LED chips 51 that are the source of the generated heat. Consequently, it is possible to detect the temperature inside the optical adapter 30 more accurately.

(Third Embodiment)

Figure 11:
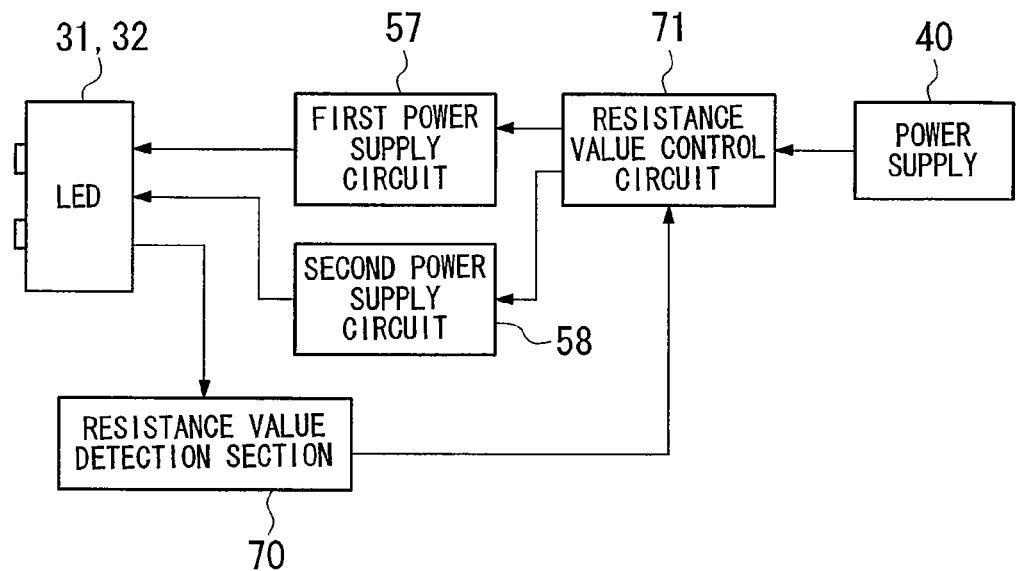
FIG. 11 is a system diagram of the power supply of a first LED unit and a second LED unit that are provided in the third embodiment of the endoscope of the present invention.

Next, the third embodiment of the present invention will be described with reference made to FIG. 11. Note that in FIG. 11 component elements that have the same structure as those described in FIG. 1 through FIG. 4 are given the same symbols and a description thereof is limited.

In the present embodiment, a structure is employed in which a resistance value detecting section 70 is electrically connected to the first LED unit 31 and the second LED unit 32, and an output from the resistance value detecting section 70 is input into a resistance value control circuit 71.

On the basis of this structure, the resistance value of the first LED unit 31 and the second LED unit 32 that changes depending on the temperature is detected by the resistance value detecting section 70, and the result of this detection is input into the resistance value control circuit 71. In addition, when this resistance value reaches a predetermined value or less, the driving of the first power supply circuit 57 or the second power supply circuit 58 is switched by the resistance value control circuit 71.

By employing the above described structure, the same effects as those described above can be achieved.

(Fourth Embodiment)

Figure 12:
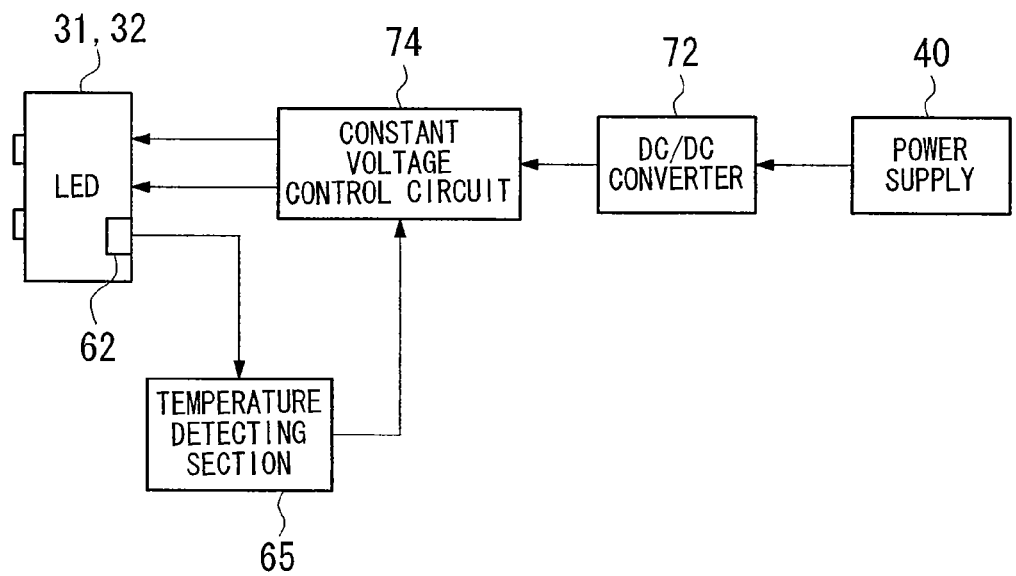
FIG. 12 is a system diagram of the power supply of a first LED unit and a second LED unit that are provided in the fourth embodiment of the endoscope of the present invention.

Next, the fourth embodiment of the present invention will be described with reference made to FIG. 12.

In the present embodiment, a structure is employed in which there is provided a DC/DC converter 72 that receives voltage supplied from the power supply 40 and outputs a stable constant voltage, and a constant voltage control circuit 74 that is electrically connected to the DC/DC converter 72. In addition, in the present embodiment, instead of the first power supply circuit and the second power supply circuit being installed, the first LED unit 31 and the second LED unit 32 are electrically connected to the constant voltage control circuit 74.

On the basis of this structure, constant voltage is supplied from the power supply 40 via the DC/DC converter 72 to the constant voltage control circuit 74. As a result, stable current is supplied to the first LED unit 31 or the second LED unit 32. Note that the switching by the constant voltage control circuit 74 of the driving between the first LED unit 31 and the second LED unit 32 in accordance with outputs from the temperature detecting section 65 is the same as in the above described second embodiment.

By employing the above described structure, not only is it possible to achieve the same effects as those described above, but variations in brightness can be suppressed by supplying stable current to the first LED unit 31 and the second LED unit 32, and the first power supply circuit 57 and the second power supply circuit 58 can be omitted. As a result, it is possible to reduce the number of components and simplify the structure.

(Fifth Embodiment)

Figure 13:
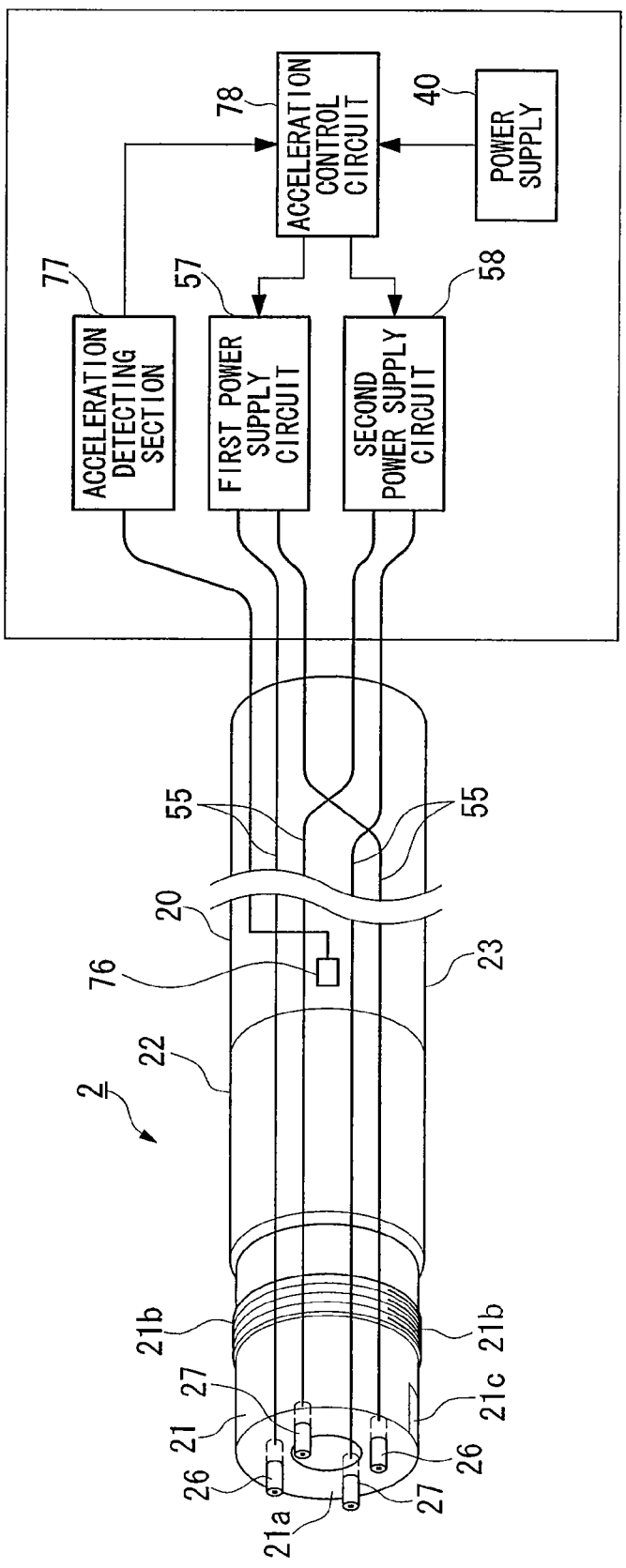
FIG. 13 is a system diagram of the power supply of a first LED unit and a second LED unit that are provided in the fifth embodiment of the endoscope of the present invention.
Figure 14:
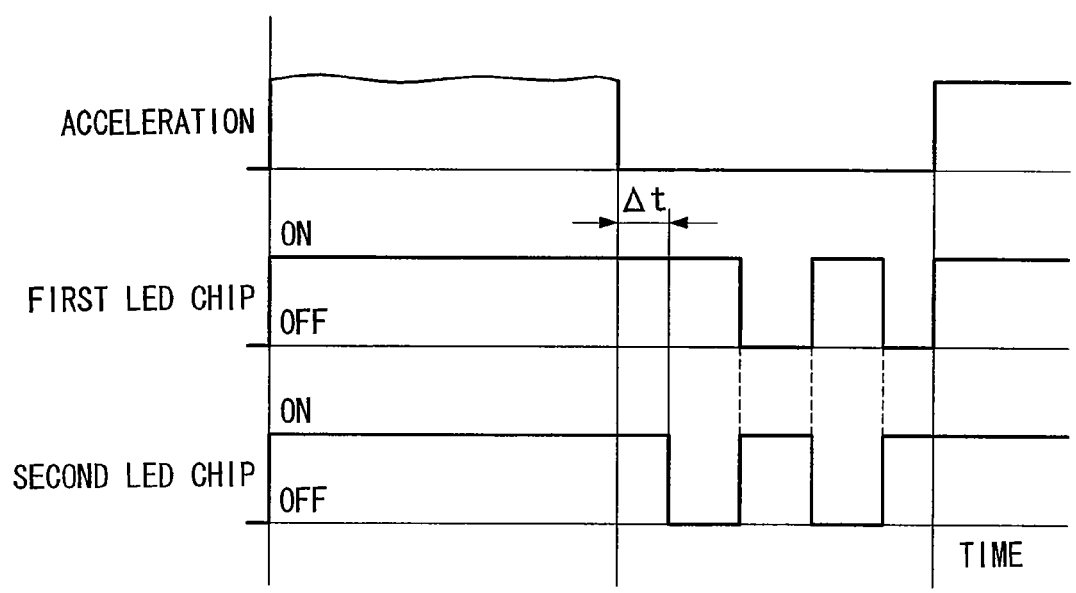
FIG. 14 is a time chart showing relationships between elapsed time and drive states of a first LED chip and a second LED chip as well as a rate of acceleration of an insertion portion that are provided in the fifth embodiment of the endoscope of the present invention.

Next, the fifth embodiment of the present invention will be described with reference made to FIG. 13 and FIG. 14.

In the present embodiment, a structure is employed in which there are provided an acceleration sensor (i.e., an acceleration detecting device) 76 that is located inside the flexible tube 23, an acceleration detecting section (i.e., an acceleration detecting device) 77 that is electrically connected to the acceleration sensor 76, and an acceleration control circuit (i.e., an alternating conduction control unit and a simultaneous conduction control unit) 78 that receives the input of detection signals from the acceleration detecting section 77.

The acceleration sensor 76 may be, for example, an electrostatic capacity type of sensor and is provided with a fixed type of fixed electrode (not shown) and a movable electrode that moves in accordance with the movement of the insertion portion 2. In addition, the acceleration detecting section 77 detects the size of the width between the fixed electrode and the movable electrode of the acceleration sensor 76, namely, detects the electrostatic capacity between these two, and outputs a signal corresponding to the size of this electrostatic capacity.

Moreover, the acceleration control circuit 78 selects whether to drive the first power supply circuit 57 and the second power supply circuit 58 simultaneously or whether to drive these two alternatingly in accordance with detection signals from the acceleration detection section 77. The first power supply circuit 57 or the second power supply circuit 58 is then driven in accordance with this selection.

Based on the above described structure, when the insertion portion 2 is inserted into an object and the interior of the object is then observed as the insertion portion 2 is moved forwards, in accordance with the forward movement of the insertion portion 2 the acceleration of the insertion portion 2 is detected by the acceleration section 76 and the acceleration detecting section 77, and a detection signal is input into the acceleration control circuit 78. Based on the detection signal at this time, as is shown in FIG. 14, the first power supply circuit 57 and the second power supply circuit 58 are both driven by the acceleration control circuit 78 and the interior of the object is sufficiently illuminated. In contrast, when the movement of the insertion portion 2 is halted and other processing is performed, then based on detection signals from the acceleration detection section 77 at this time, when a predetermined time Δt has elapsed the driving of the second power supply circuit 58 is stopped while the driving of the first power supply circuit 57 continues. When a further fixed time has elapsed, the second power supply circuit 58 is driven while the driving of the first power supply circuit 57 is stopped. As a result, the driving of the first LED unit 31 and the second LED unit 32 is controlled in accordance with the movement of the insertion portion 2.

By employing the above described structure, when the insertion portion 2 is inserted into an object and the object is observed as the insertion portion 2 is moved forward, the amount of generated light is increased so that observation is made easier. When the movement of the insertion portion 2 is stopped and other processing is performed, it is possible to suppress the amount of generated light and prevent the temperature inside the optical adaptor 30 from rising.

Note that, in the present embodiment, the first LED chips 50 and the second LED chips 51 are set such that three of each are arranged in a straight line in two parallel rows, however, the present invention is not limited to this and the number of LED chips that are installed may be set as is appropriate.

(Sixth Embodiment)

Next, the sixth embodiment of the endoscope of the present invention will be described with reference made to FIG. 15A through FIG. 25.

Figure 15A:
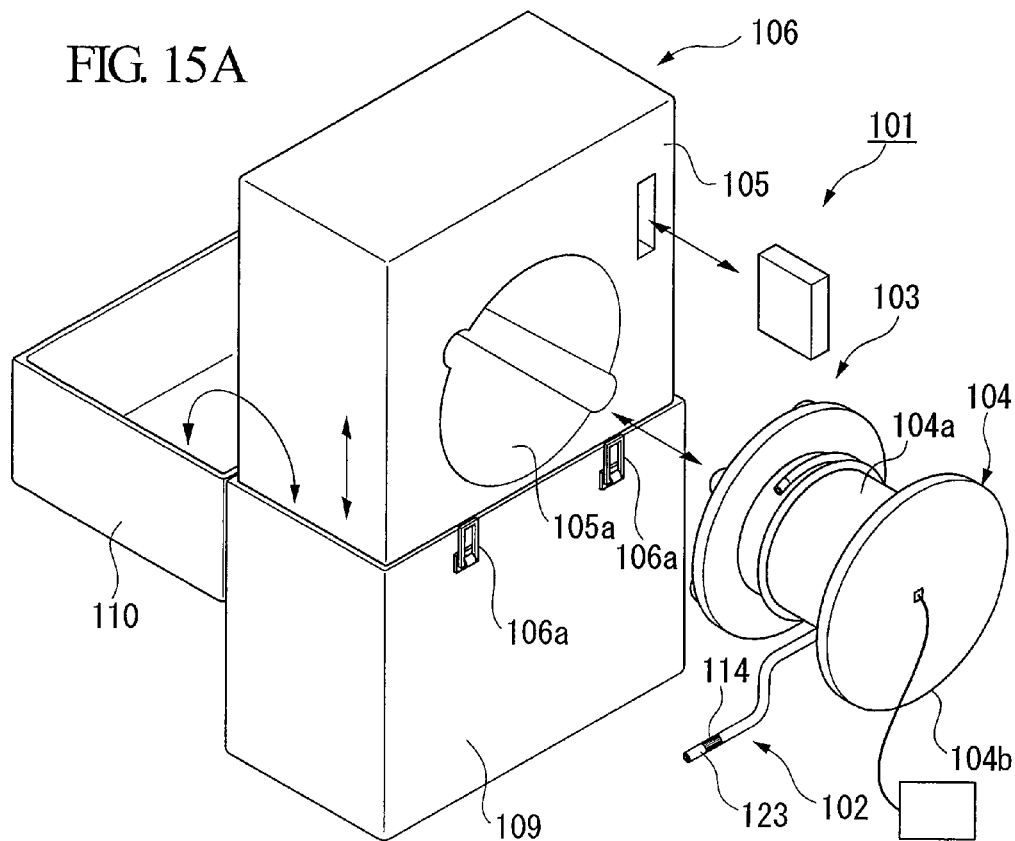
FIG. 15A is a view showing a sixth embodiment of the endoscope of the present invention, and is an exploded perspective view showing a state before the endoscope body is placed inside a case.
Figure 15B:
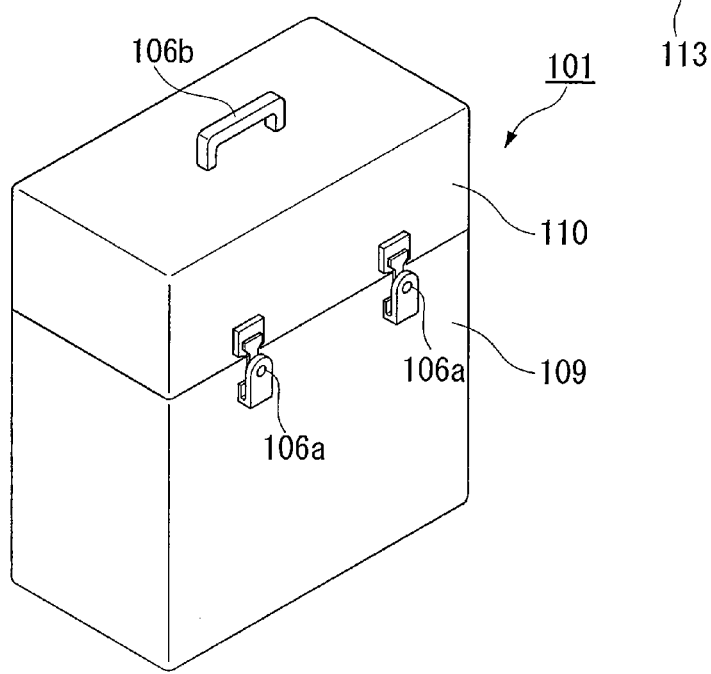
FIG. 15B is a view showing a sixth embodiment of the endoscope of the present invention, and is an exterior perspective view showing a state when the endoscope body is placed inside the case.

FIG. 15A is an exploded perspective view showing a state before an endoscope body of an endoscope 101 of the present embodiment is placed inside a case, and FIG. 15B is an exterior perspective view showing a state when this endoscope body is placed inside the case.

The endoscope 101 is provided with a case 106 that is formed in the shape of a box, and an endoscope body 103 that can be placed inside the case 106. The case 106 is provided with a box-shaped body portion 109, and a lid portion 110 that is attached to the body portion 109 and is able to be opened and closed. A housing portion 105 that is formed from a cushioning material or the like is provided inside the case 106, and a housing concave portion 105a in which the endoscope body 103 is housed is formed in the housing portion 105.

On the basis of this structure, by housing the endoscope body 103 inside the housing concave portion 105a and then closing the lid portion 110, the endoscope body 103 may be stored and transported together with the case 106. Note that the symbols 106a are clasps, and the symbol 106b is a handle.

The endoscope body 103 has as its principal component elements a narrow elongated insertion portion 102 that is inserted into an object, and a drum portion 104 onto which the insertion portion 102 is wound and stored.

The drum portion 104 is formed in the shape of a bobbin, for example, having disk-shaped flanges 104b that are attached to both ends in a longitudinal direction of a cylindrical winding portion 104a onto which the insertion portion 102 is wound. An LCD monitor (i.e., a display device) 113 that is used to display images is connected to a flange 104b. In addition, a remote controller (not shown) that is provided with a joystick or the like that is used to perform a bending operation to bend the insertion portion 102 is connected via an operating cable to the drum portion 104.

Figure 16:
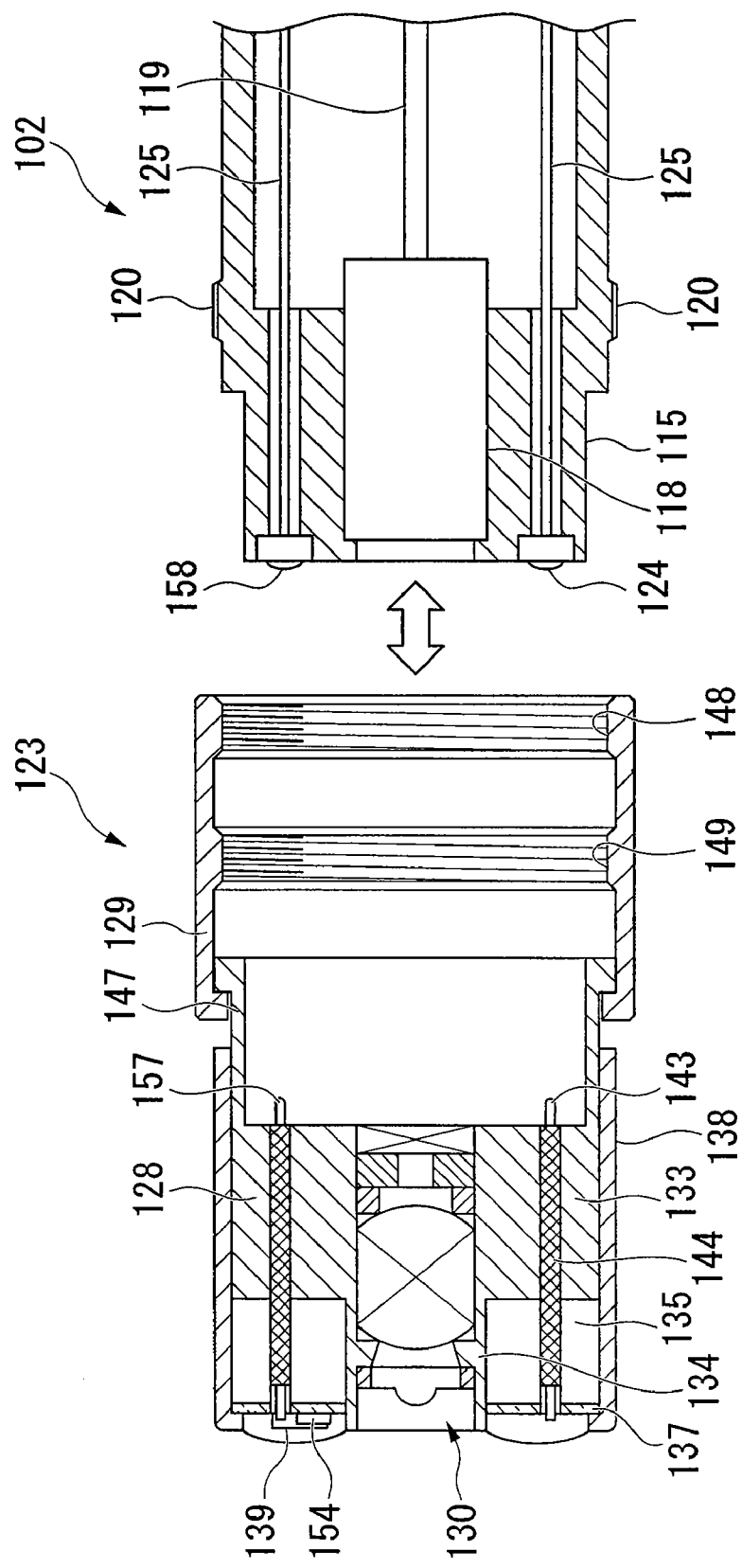
FIG. 16 is a side cross-sectional view of an insertion portion and an optical adaptor that is fitted into a distal end of the insertion portion of the sixth embodiment of the endoscope of the present invention.

Furthermore, a bending portion 114 that is able to be bent is provided in the vicinity of a distal end portion of the insertion portion 102. The bending portion 114 is provided with a plurality of fluid pressure actuators for performing a bending operation. Note that a non-combustible gas such as, for example, carbon dioxide, freon, nitrogen, helium, and argon is used for the operating fluid for a bending operation. As is shown in FIG. 16, a distal end hard portion 115 is provided at the distal end of the bending portion 114. A threaded portion 120 that extends in the circumferential direction is provided around the entire outer circumference of the distal end hard portion 115. A CCD 118 is built into the distal end hard portion 115 as an image pickup device. The CCD 118 transmits signals of picked up images via a CCD cable 119 that passes through an internal space inside the insertion portion 102.

An insertion portion side electrode terminal 124 to which an electric wire 125 is connected is provided on a distal end surface of the distal end hard portion 115.

Furthermore, an optical adaptor (i.e., an adaptor for the endoscope) 123 is removably attached to the distal end portion of the insertion portion 102. The optical adaptor 123 is provided with a substantially cylindrical adapter body portion 128 and a connecting cylinder portion 129. The adapter body portion 128 and the connecting cylinder portion 129 are joined together such that they can be rotated relative to each other.

The adapter body portion 128 is formed by a heat conductive member made of brass, copper, aluminum, or the like, and a cylinder-shaped outer cylinder portion 138 made of stainless steel or the like is provided at an outer circumference thereof. The adapter body portion 128 is constructed such that a large diameter portion 133 and a small diameter portion 134 are joined together integrally. An observation optical system 130 is provided in the cylinder holes of the large diameter portion 133 and the small diameter portion 134.

Figure 17:
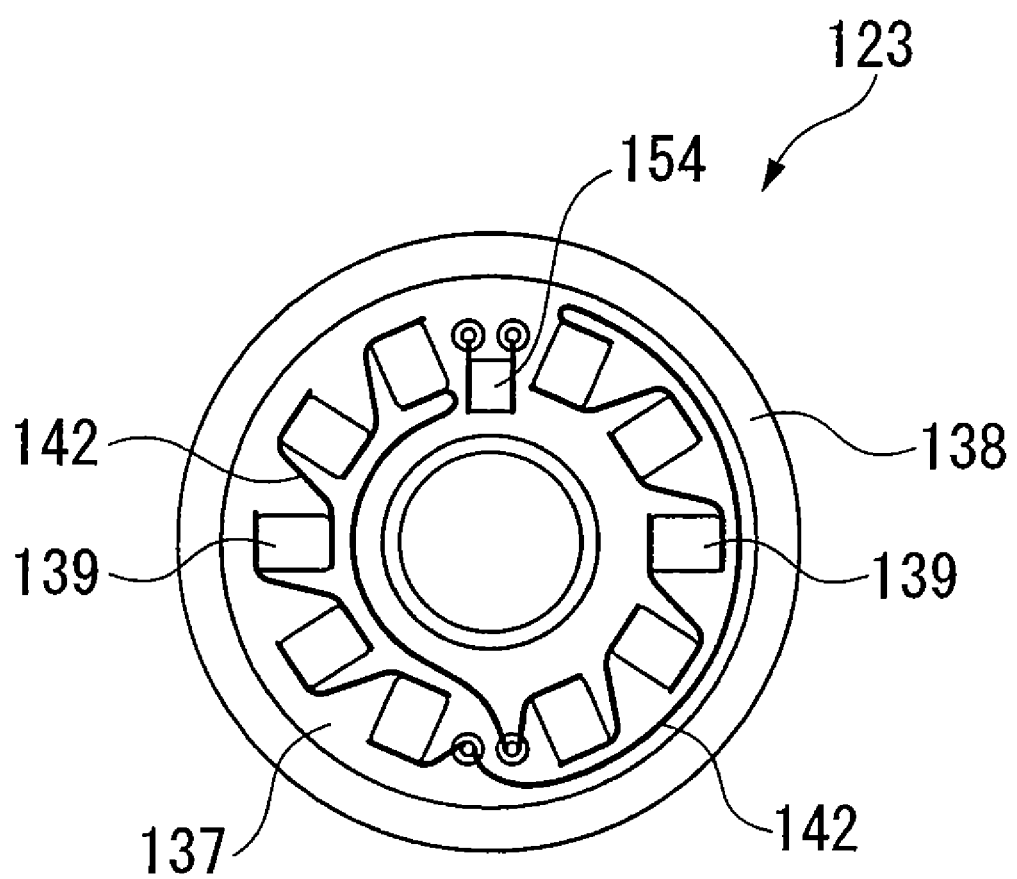
FIG. 17 is a front view of the optical adaptor of the sixth embodiment of the endoscope of the present invention.

A donut-shaped aluminum substrate 135 is provided at a distal end surface of the large diameter portion 133, and a flexible substrate 137 is provided at a distal end surface of the aluminum substrate 135. The aluminum substrate 135 and the flexible substrate 137 are formed by heat conductive members, and are supported by the insertion of the small diameter portion 134. As is shown in FIG. 17, a plurality of LED (i.e., illumination devices) 139 are provided extending in a circumferential direction on the flexible substrate 137. The LED 139 are connected together via LED wiring 142.

An adaptor side electrode terminal 143 is provided at a rear end surface of the large diameter portion 133. This adapter side electrode terminal 143 is electrically connected to the LED 139 via an electrode rod 144 that is covered by a non-conductive body. Furthermore, a joining portion 147 that protrudes towards the rear is incorporated into the rear end surface of the large diameter portion 133. The connecting cylinder portion 129 is rotatably attached to the joining portion 147.

The connecting portion 129 is formed from stainless steel or the like and a first female threaded portion 148 is formed at a rear end portion thereof extending around the entire inner circumferential surface. Furthermore, a second female threaded portion 149 is formed on the distal end side a predetermined distance away from the first female threaded portion 148.

Based on the above described structure, if the distal end of the insertion portion 102 is inserted into the rear end of the optical adapter 123 and the connecting cylinder portion 129 is rotated, then, firstly, the male threaded portion 120 and the first female threaded portion 148 mesh together. If the connecting cylinder portion 129 is then further rotated in the same direction, the male threaded portion 120 moves past the first female threaded portion 148 and meshes with the second female threaded portion 149. As a result, the optical adapter 123 is removably attached to the distal end of the insertion portion 102. Namely, the first female threaded portion 148 functions as a stopper to prevent the optical adapter 123 coming off the insertion portion 102. Furthermore, if the optical adapter 123 is attached to the distal end of the insertion portion 102, then the insertion portion side electrode terminal 124 and the adapter side electrode terminal 143 are electrically connected.

Figure 18:
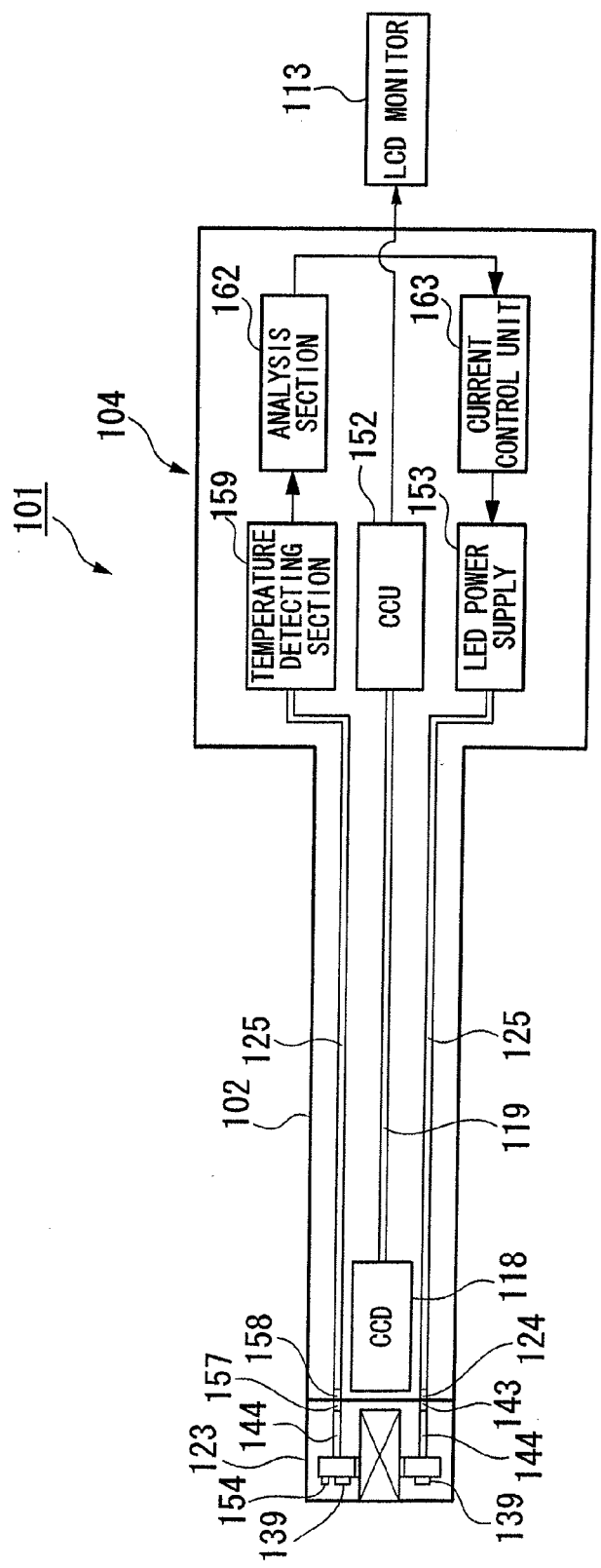
FIG. 18 is a block diagram illustrating functions of the sixth embodiment of the endoscope of the present invention.

Moreover, as is shown in FIG. 18, a CCU (i.e., a camera control unit) 152 that is connected via a CCD cable 119 to the CCD 118 is provided on the drum portion 104, and the CCU 152 is connected to the LCD monitor 113. An LED power supply 153 is also provided on the drum portion 104 and current having a predetermined current value is supplied from this LED power supply 153 via the electric wire 125 and the electrode rod 144 to the LED 139.

Furthermore, as is shown in FIG. 16 and FIG. 17, the endoscope 101 of the present embodiment is provided with a temperature sensor (i.e., a detecting device) 154 that has a predetermined resistance built into it. The temperature sensor 154 is provided in the vicinity of the LED 139 on the flexible substrate 137. When a predetermined current is supplied to the temperature sensor 154, a voltage that corresponds to the surrounding temperature is applied thereto. Furthermore, the temperature sensor 154 is connected via the electrode rod 144 to an adapter side sensor terminal 157 that is provided at a rear end surface of the adaptor body portion 128. When the optical adapter 123 is attached to the distal end of the insertion portion 102, the adapter side sensor terminal 157 is in contact with the insertion portion side sensor terminal 158 that is provided at the distal end surface of the distal end hard portion 115, and the two are in a state of conduction with each other. As is shown in FIG. 18, the insertion portion side sensor terminal 158 is electrically connected via an electric wire 125 to a temperature detecting section (i.e., a detecting device) 159 that is provided in the drum portion 104.

The temperature detecting section 159 is electrically connected to an analysis section (i.e., a brightness altering device) 162 that makes analyses in accordance with detection results from the temperature detecting section 159. Low level threshold values $T_L$ and high level threshold values $T_H$ (see FIG. 19) relating to temperature are stored in advance in the analysis section 162. The analysis section 162 is electrically connected to a current control unit (i.e., a light amount adjusting device) 163 that is connected to the LED power supply 153. The current control unit 163 performs switching control to switch the value of the current supplied from the LED power supply 153 between a low level current value $I_L$ and a high level current value $I_H$.

Next, the operation of the endoscope 101 of the present embodiment will be described.

Firstly, the optical adapter 123 is attached to the insertion portion 102 and the insertion portion 102 is inserted into an object. Next, as is described below, current that has been set to a high level current value $I_H$ is supplied from the LED power supply 153 to the LED 139 and illumination light is irradiated from the LED 139. Next, reflection light from the object is obtained via the observation optical system 130. This reflection light is converted into electrical signals in the form of image pickup signals by the CCD 118 and these image pickup signals are input via the CCD cable 119 into the CCU 152. Predetermined processing is then performed by the CCU 152 on the image pickup signals, and the image pickup signals are then supplied to the LCD monitor 113 as image signals. As a result, an observation image is displayed on the LCD monitor 113. At this time, by operating the remote controller and then being the bending portion 114, the distal end portion of the insertion portion 102 is made to face in a desired direction. An operator then observes the object by observing the observation image and various types of processing can be performed.

Here, by driving the LED 139, an observation image whose brightness corresponds to the high level current value $I_H$ is displayed on the LCD monitor 113, however, if the temperature of the LED 139 rises and exceeds a predetermined value, then there is a deterioration (i.e., noise and the like is generated) in the image quality of the LCD monitor 113. Namely, conventionally, it has not been possible to easily obtain an observation image having an appropriate brightness when the LED 139 and CCD 118 are made to function in their most appropriate states. In the endoscope 101 of the present embodiment, the observation image on the LCD monitor 113 is set to an appropriate image with little noise in the manner described below.

Figure 19:
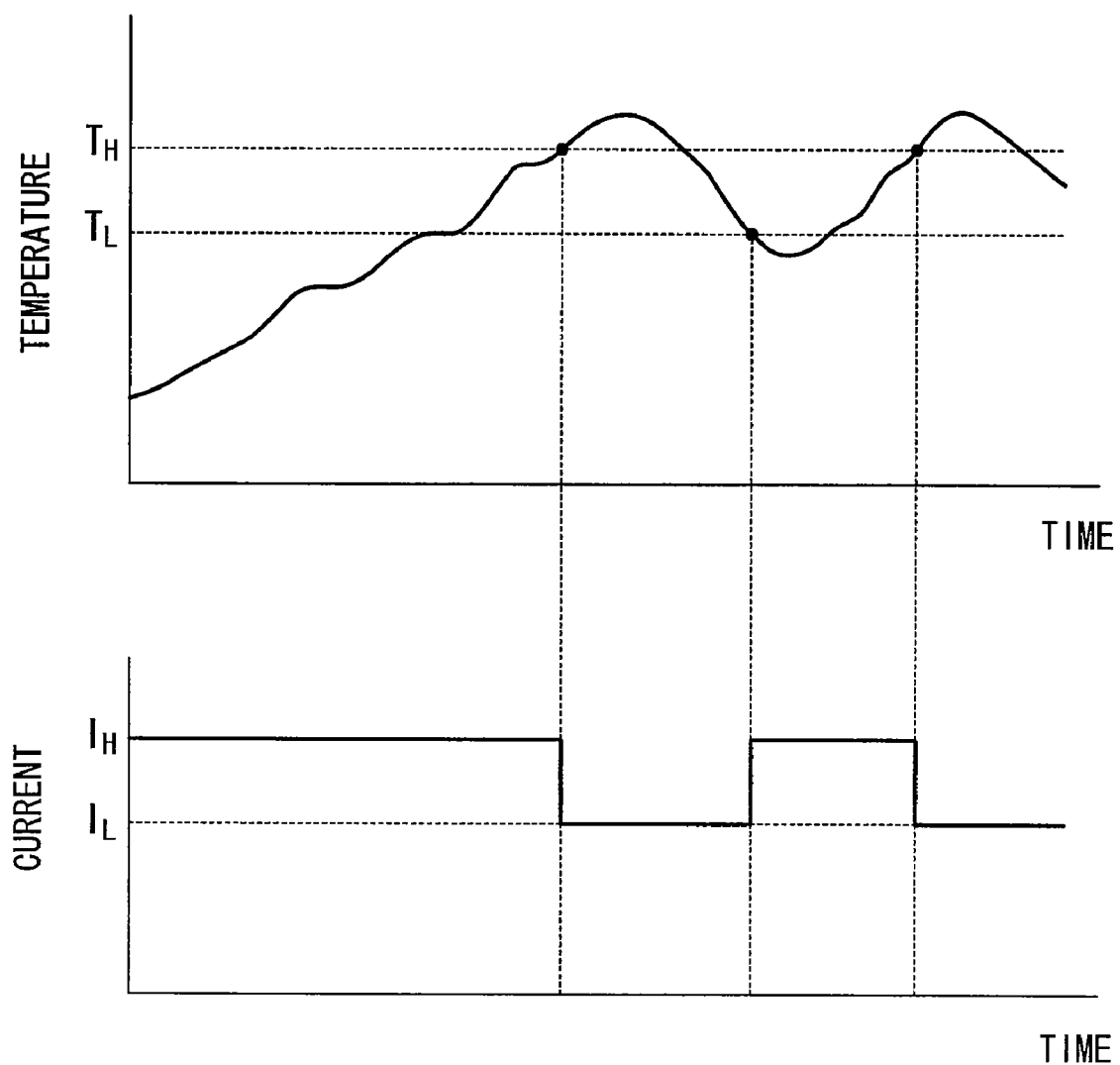
FIG. 19 is a graph showing changes in the temperature around an LED and also a state when a current value is switched in the sixth embodiment of the endoscope of the present invention.

Namely, as is shown in FIG. 19, if the LED 139 is driven, then there is a rise in the temperature around the LED 139. During this observation, the temperature surrounding the LED 139 is detected by the temperature sensor 154 and the temperature detecting section 159, and the detection signals are input into the analysis section 162. The analysis section 162 compares the temperature around the LED 139 based on these detection signals with the high level threshold value $T_H$ that has been set in advance. If the temperature around the LED 139 exceeds the threshold value $T_H$, a switching signal is output. This switching signal is input into the current control unit 163 and the current from the LED power supply 153 is switched by the current control unit 163 from the high level current value $I_H$ to the low level current value $I_L$. As a result, the amount of light from the LED 139 is reduced and the amount of generated heat is also reduced. In addition, by reducing the amount of light from the LED 139, noise and the like in the observation image displayed on the LCD monitor 113 is reduced and the image can be adjusted to a suitable image.

Furthermore, by reducing the amount of heat generated by the LED 139, the temperature around the LED 139 is lowered, however, if this temperature falls below the low level threshold value $T_L$, a switching signal is output from the analysis section 162 and the current from the LED power supply 153 is switched by the current control unit 163 to the high level current value $I_H$. By then repeating this series of operations the brightness of the LCD monitor 113 can be appropriately adjusted.

By employing the above described structure, according to the endoscope 101 it is possible to accurately and easily adjust the brightness of an observation image that is displayed on the LCD monitor 113 in accordance with the temperature around the LED 139.

Moreover, because the temperature around the LED 139 is detected and the current value is then switched, it is possible to prevent the temperature around the LED 139 from becoming too hot. As a result, not only is it possible to obtain a high quality image, but it is also possible to improve the durability of the LED 139 and maintain the integrity of the LED 139 for a longer period of time.

Figure 20:
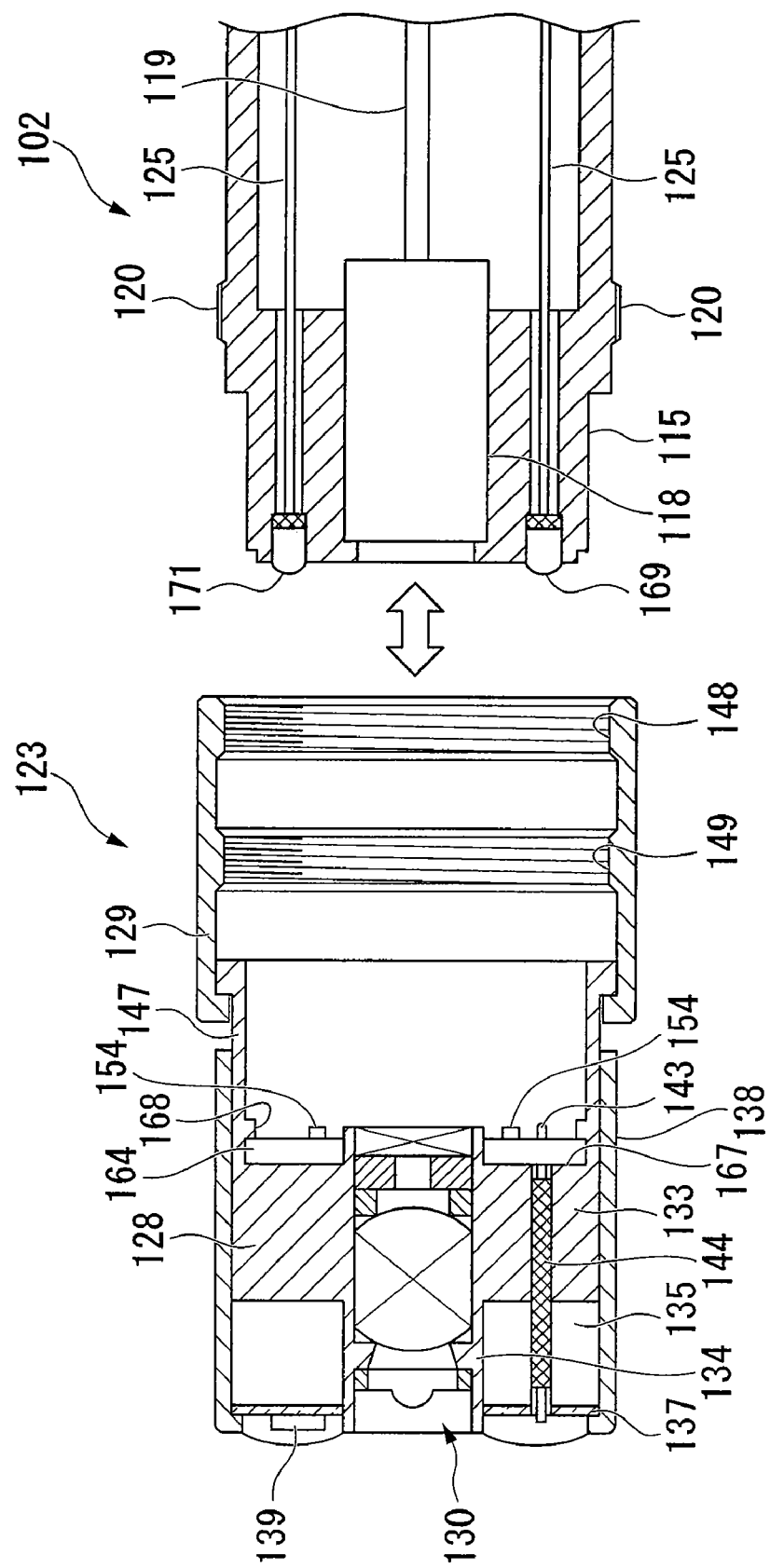
FIG. 20 is a side cross-sectional view showing a variant example of the insertion portion and optical adaptor of the sixth embodiment of the endoscope of the present invention.
Figure 21:
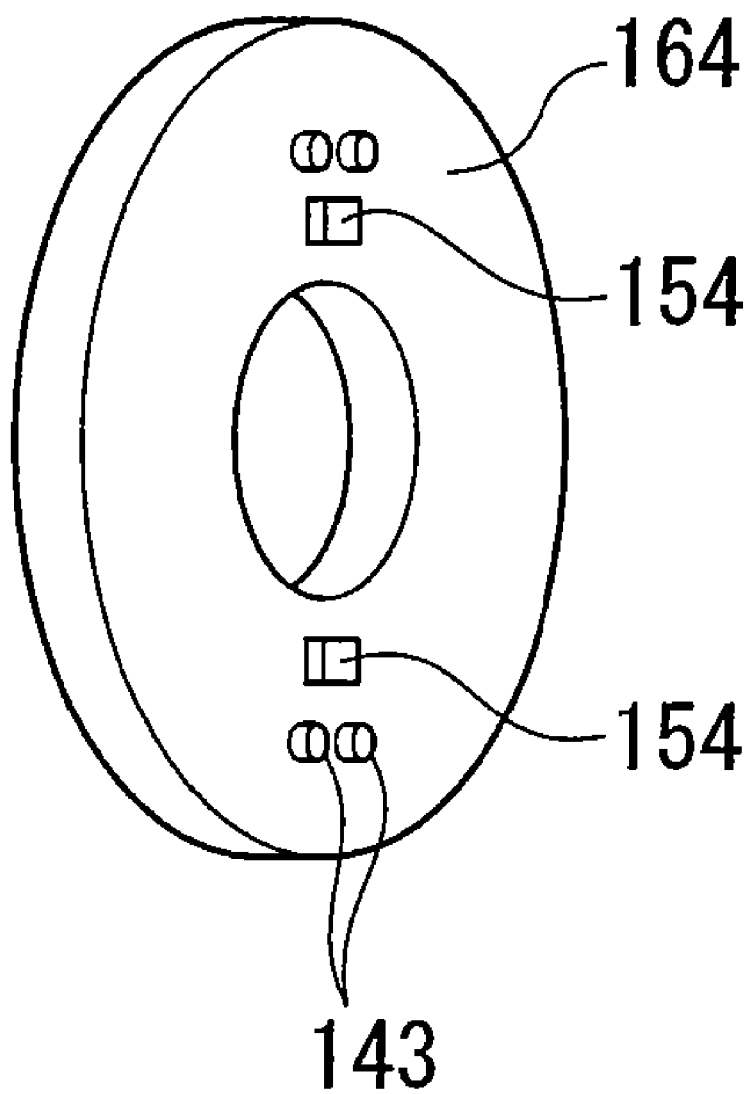
FIG. 21 is a perspective view as seen from the viewpoint of an operator of an adaptor provided in the variant example shown in FIG. 20.

Note also that in the present embodiment, the temperature sensor 154 is provided on the flexible substrate 137, however, the present invention is not limited to this and it is also possible for the placement position of the temperature sensor 154 to be altered as is appropriate. For example, as is shown in FIGS. 20 and 21, temperature sensors 154 may also be provided on an adaptor substrate 164. Namely, a concave portion 167 is formed in a rear end surface of the adaptor body portion 128, and a donut-shaped adaptor substrate 164 is provided in this concave portion 167. The adaptor substrate 164 is supported by a protruding portion 168 that is formed on an inner circumferential surface of the joining portion 147. Furthermore, an insertion portion side electrode terminal 169 and an insertion portion side sensor terminal 171 are formed from anisotropic conductive rubber, and are made conductive when the insertion portion 102 is compressed in the longitudinal direction thereof. By employing this type of structure, the number of elements packaged on the flexible substrate 137 can be limited and the diameter of the optical adaptor 123 can be made narrower.

Figure 22:
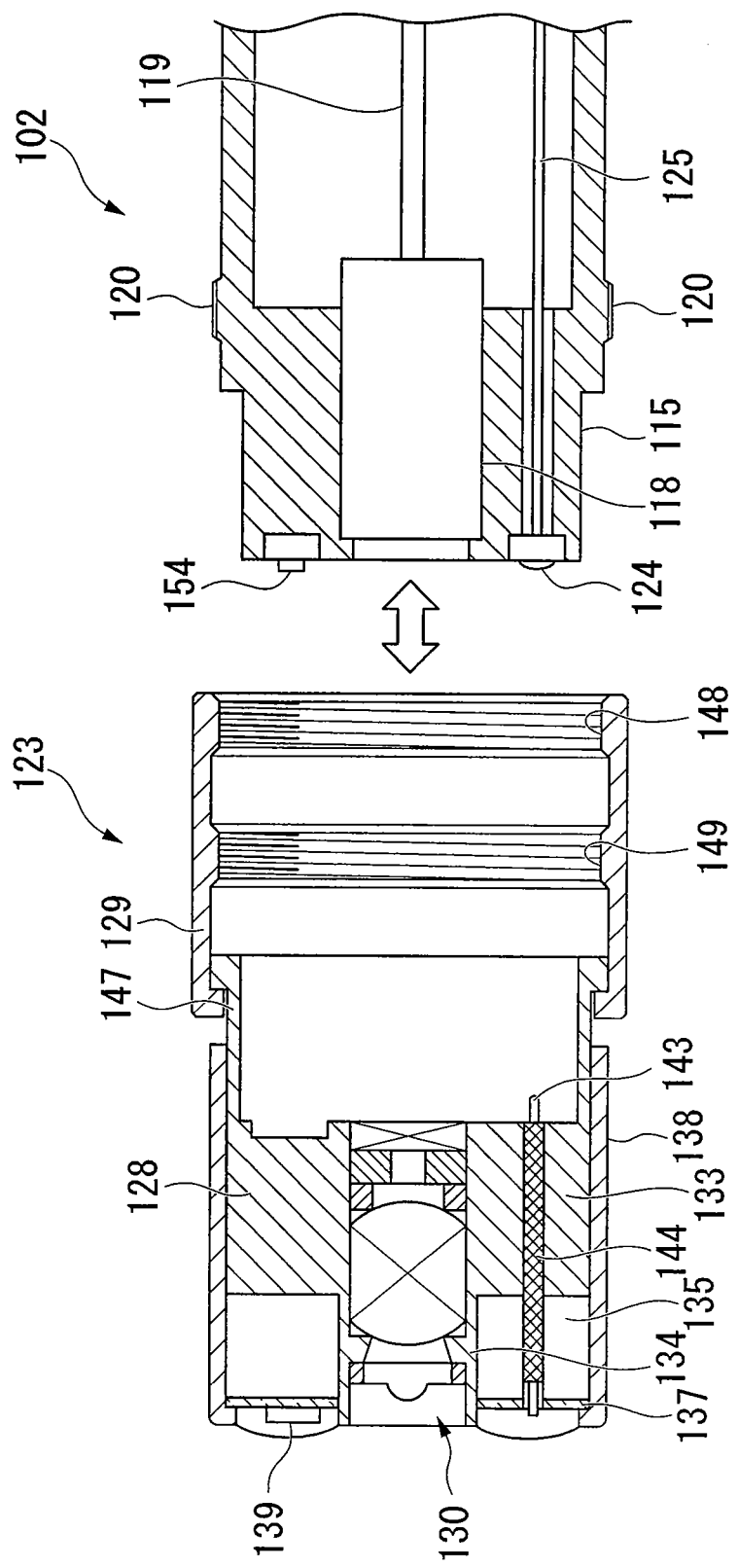
FIG. 22 is a side cross-sectional view showing another variant example of the insertion portion and optical adaptor of the sixth embodiment of the endoscope of the present invention.
Figure 23:
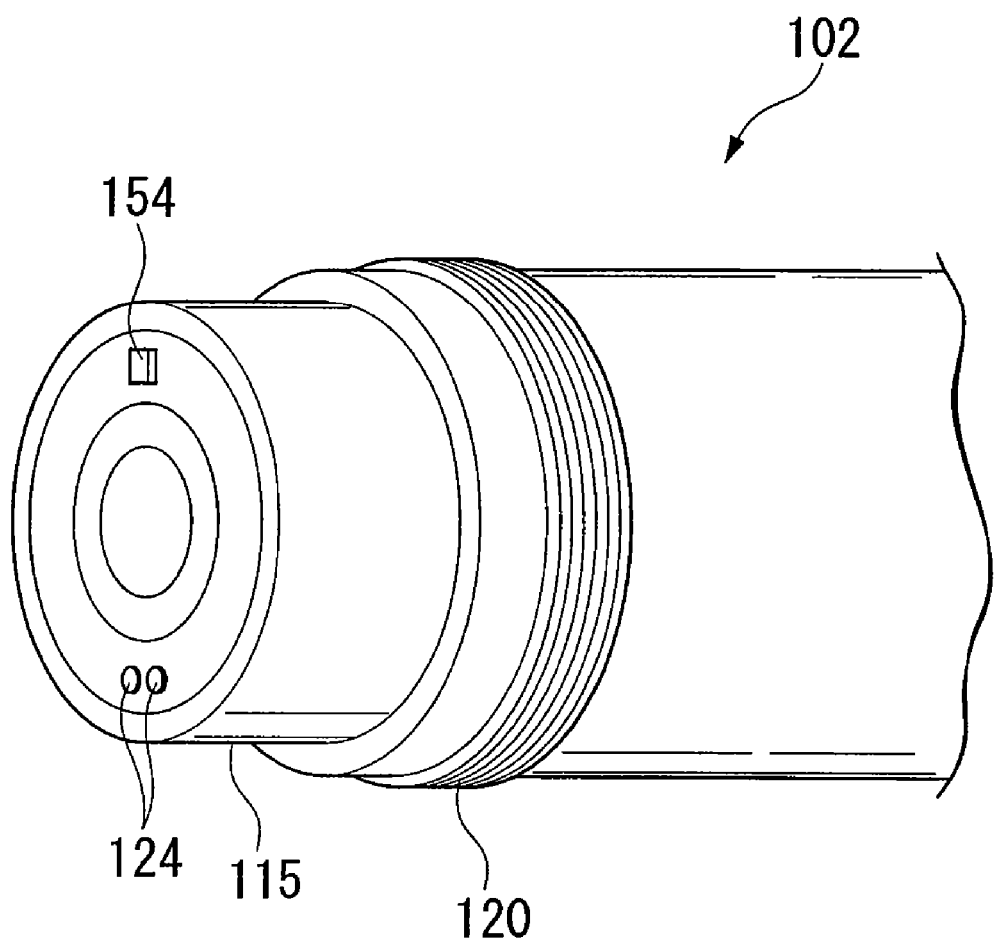
FIG. 23 is a perspective view showing a distal end surface of the insertion portion provided in the variant example shown in FIG. 22.

Moreover, as is shown in FIGS. 22 and 23, a temperature sensor 154 may also be provided on a distal end surface of the distal end hard portion 115. This allows the structure of the optical adaptor 123 to be simplified.

Either one or a plurality of temperature sensors 154 may be provided, however, the number may be set to one if a reduction in size is desired, while a plurality may be provided if there is sufficient space and an accurate measurement can be made by taking the average of this plurality.

Figure 24:
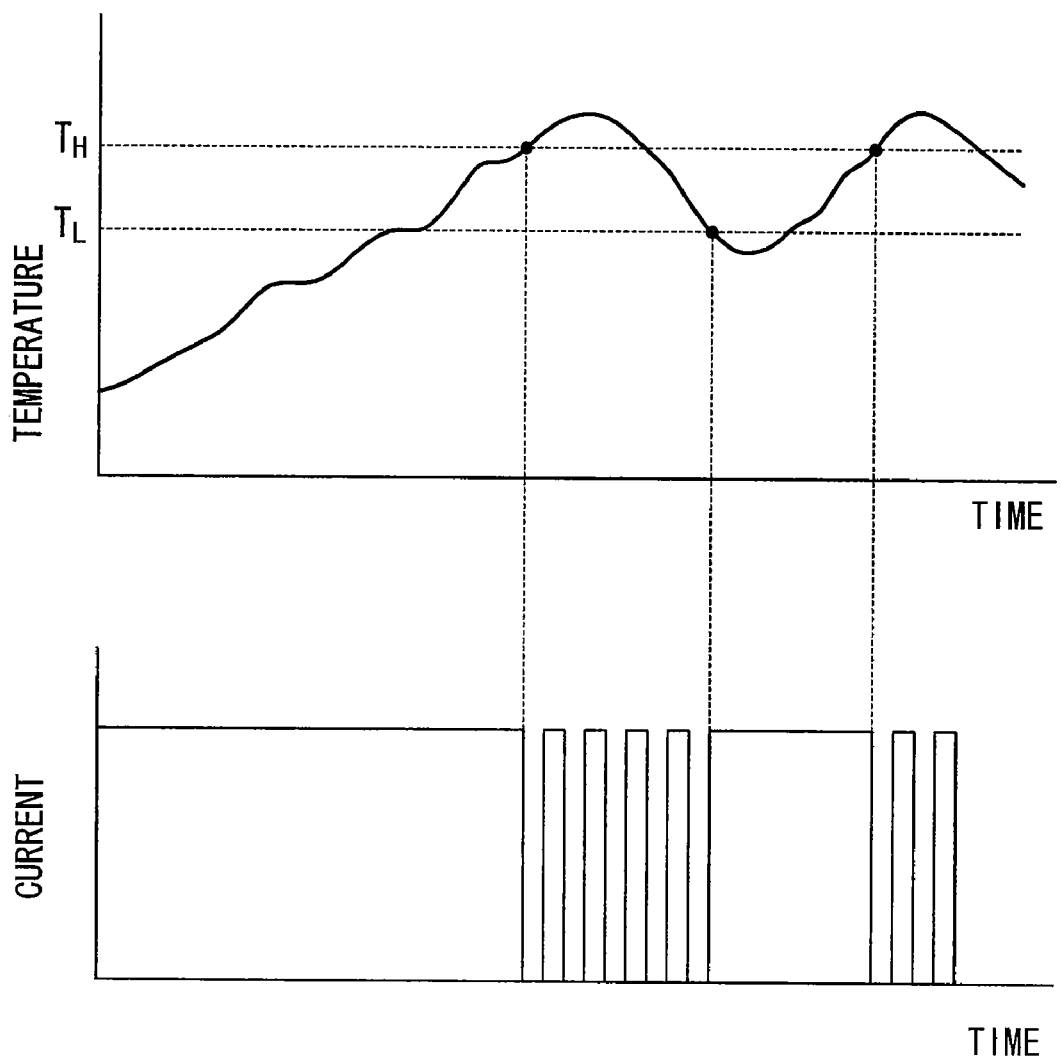
FIG. 24 is a variant example of a graph showing changes in the temperature around an LED and also a state when a current value is switched, and is a graph showing a state when the current is switched to a pulse current.

Moreover, the current value of the current supplied from the LED power supply 153 is switched between $I_H$ and $I_L$ by the current control unit 163, however, the present invention is not limited to this and the brightness altering device may be changed as is appropriate. For example, as is shown in FIG. 24, it is also possible to drive the LED 139 at first with stationary current and, when the temperature around the LED 139 increases to a threshold value $T_H$, to switch to a pulse current having a predetermined width. When the temperature then drops to a threshold value $T_L$, the current may then be switched back to a stationary current.

Figure 25:
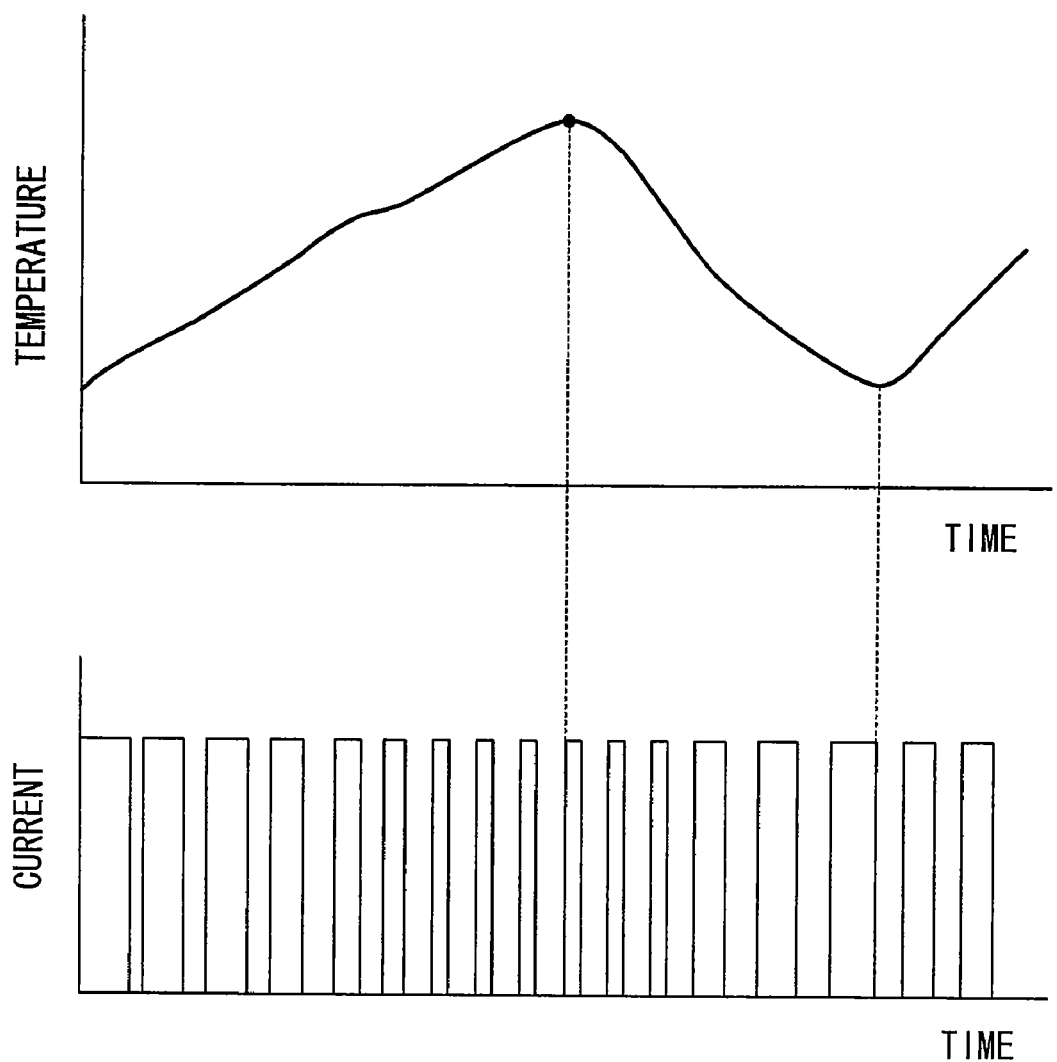
FIG. 25 is a variant example of a graph showing changes in the temperature around an LED and also a state when a current value is switched shown in FIG. 24, and is a graph showing a state when the pulse width is adjusted in accordance with the temperature.

It is also possible, as is shown in FIG. 25, to adjust the pulse width of a pulse current in accordance with the temperature around the LED 139. Namely, pulse widths corresponding to temperatures are set in advance, and the pulse width may then be set to correspond to the current temperature.

Note that if the temperature sensor 154 is provided not on the flexible substrate 137 where the LED 139 is positioned, but, as is shown in FIG. 20 or FIG. 24, adjacent to a joining portion joining the optical adaptor 123 to the insertion portion 102 which is slightly away from the LED 139, then the threshold value temperature may be set lower than when the temperature sensor 154 is provided on the flexible substrate 137.

(Seventh Embodiment)

Figure 26:
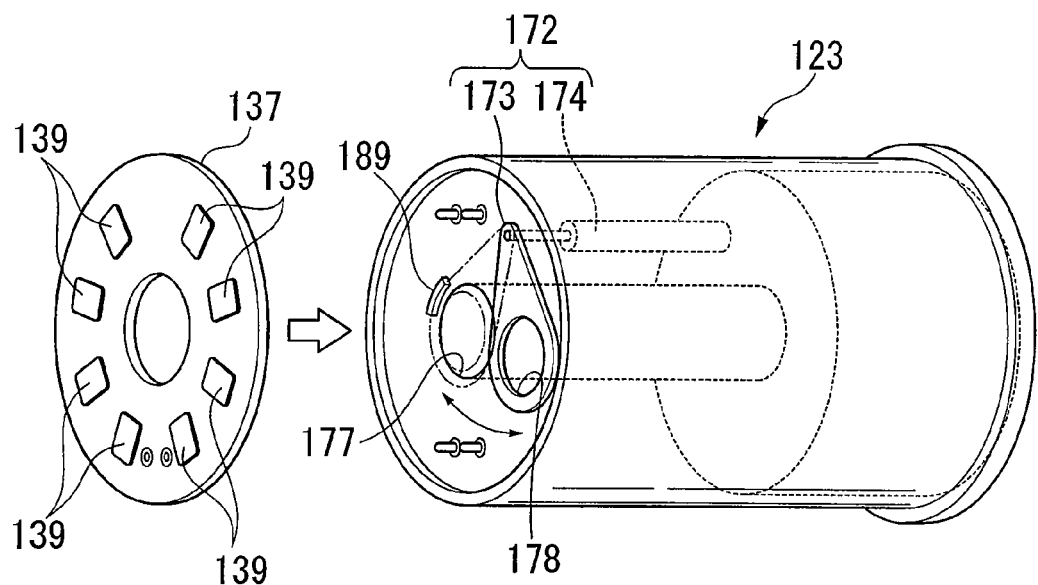
FIG. 26 is an exploded perspective view showing principal portions of a seventh embodiment of the endoscope of the present invention.
Figure 27:
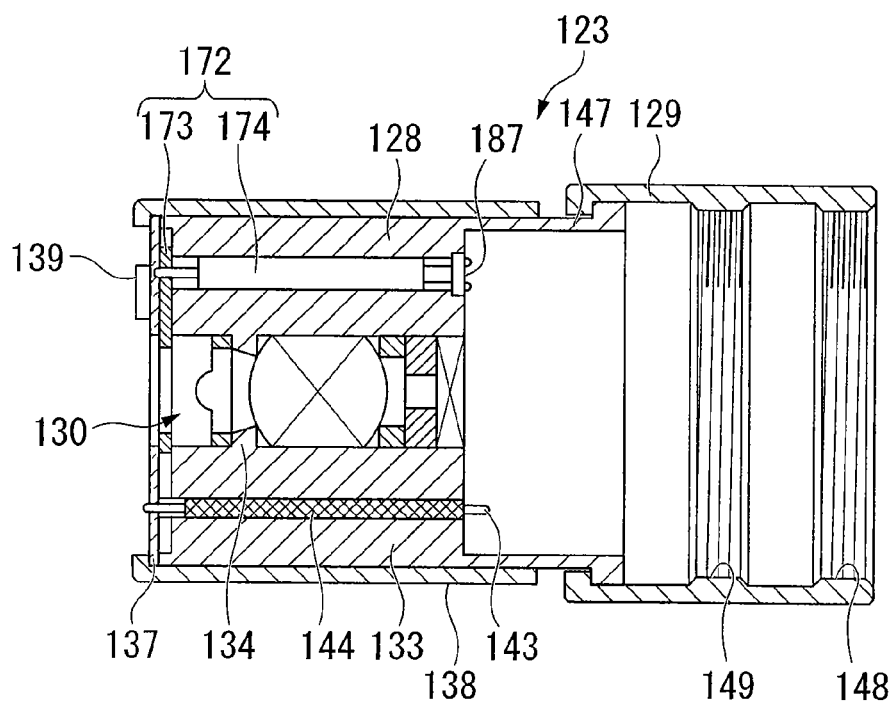
FIG. 27 is a side cross-sectional view showing an optical adaptor of the seventh embodiment of the endoscope of the present invention.
Figure 28:
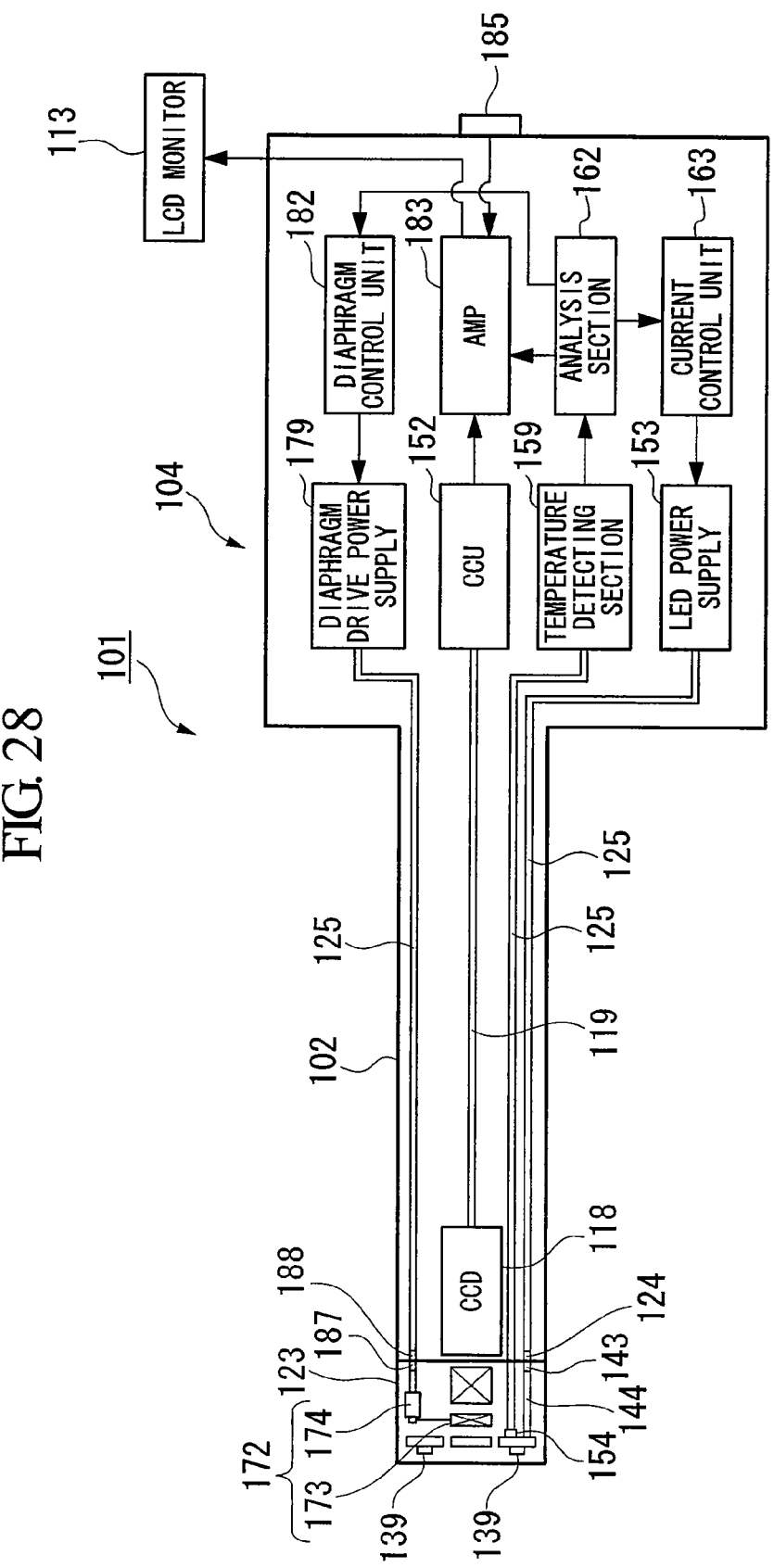
FIG. 28 is a block diagram for illustrating finctions of the seventh embodiment of the endoscope of the present invention.

Next, the seventh embodiment of the endoscope of the present invention will be described with reference made to FIG. 26 through FIG. 28. In FIG. 26 through FIG. 28, component elements that have the same structure as those described in FIG. 15A through FIG. 25 are given the same symbols and a description thereof is limited.

The basic structure of the present embodiment is the same as that of the first embodiment, and only points of difference with the first embodiment are described here.

In the present embodiment, as is shown in FIGS. 26 and 27, a diaphragm mechanism 172 that adjusts the amount of reflection light that is taken in is provided in the optical adaptor 123. The diaphragm mechanism 172 is provided with a diaphragm portion 173 that has a diaphragm hole 178 whose diameter is smaller than that of the cylinder hole in an adaptor body portion 184, and with a motor 174 that rotates the diaphragm portion 173. As is shown in FIG. 28, the motor 174 is electrically connected to a diaphragm drive power supply 179 via an adaptor side motor terminal 187 and an insertion portion side motor terminal 188. The motor 174 is driven when power is supplied thereto from the diaphragm drive power supply 179. In addition, by driving the motor 174, the diaphragm portion 173 is moved reciprocally between a diaphragm position where the diaphragm hole 178 is placed on a front surface of an acquisition hole 177 (shown in FIG. 26), and an open position where the acquisition hole 177 is left open.

The diaphragm drive power supply 179 is electrically connected to a diaphragm control unit (i.e., a diaphragm control device) 182 and is controlled by the diaphragm control unit 182. The diaphragm control unit 182 is electrically connected to the analysis section 162.

Furthermore, the CCD 152 is connected to the LED monitor 113 via an amp 183. The amp 183 is connected to an image switching switch 185 that is provided on an outer surface of the drum portion 104.

Note that the symbol 189 shown in FIG. 26 indicates a stopper that restricts the rotation of the diaphragm portion 173.

Figure 29:
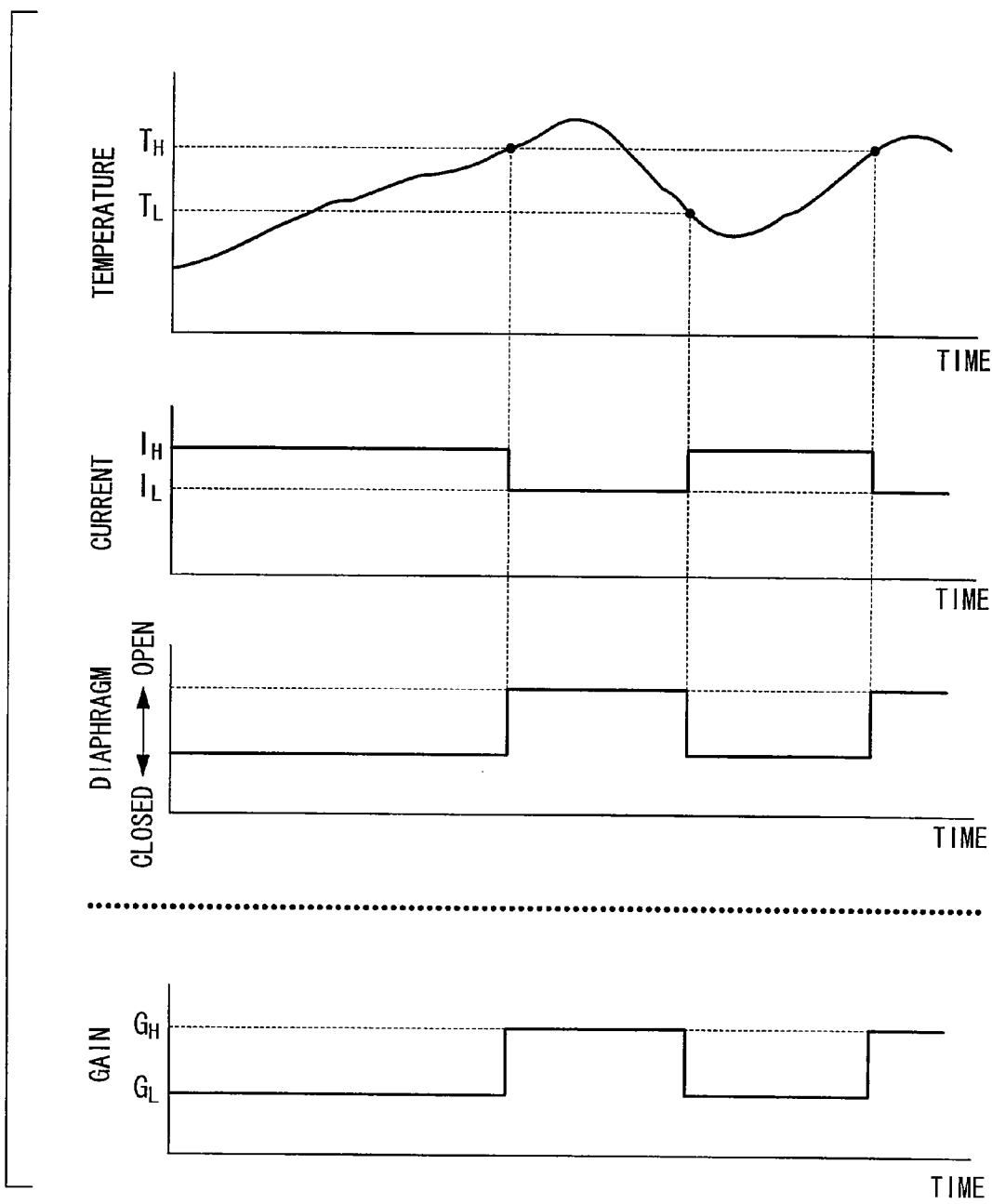
FIG. 29 is a graph showing changes in the temperature around an LED, a state when the current value is switched, changes when a diaphragm is opened and closed, and changes in gain in the seventh embodiment of the endoscope of the present invention.

Based on the above described structure, as is shown in FIG. 29, a high level current value $I_H$ is supplied at first from the LED power supply 153 and the diaphragm portion 173 is placed in the diaphragm position. At this time, there is a large amount of illumination light from the LED 139 and the reflection light taken into the distal end of the insertion portion 102 passes through the diaphragm hole 178, which results in the amount of light arriving at the CCD 118 being restricted. In addition, an image corresponding to this amount of light is displayed on the LCD monitor 113. When the temperature around the LED 139 then exceeds the threshold value $T_H$, a switching signal and a drive signal are output from the analysis section 162. The switching signal is input into the current control unit 163 and, in the same way as is described above, the current supplied from the LED power supply 153 is switched to the current value $I_L$. In contrast, the drive signal is input into the diaphragm control unit 182 and power is supplied from the diaphragm drive power supply 179 to the motor 174 based on the control of the diaphragm control unit 182. The motor 174 is then driven and the diaphragm portion 173 is placed in the open position.

As a result of this structure, the amount of heat generated by the LED 139 is restricted and the amount of illumination light is also restricted. At this time, because the diaphragm portion 173 is placed in the open position, the reflection light arrives at the CCD 118 without the amount of this reflection light that is taken into the insertion portion 102 being restricted. Namely, as a result of the analysis section 162 functioning as a joint control unit and the diaphragm control unit 182 and the current control unit 163 being jointly controlled, a uniform amount of light from before and after the switching arrives at the CCD 118. Note that, when the image that is displayed on the LCD monitor 113 is dark, by turning on the image switching switch, the output from the amp 183 is switched from a low level gain $G_L$ to a high level gain $G_H$. The result of this is that the image signals output from the CCU 152 are further amplified and the brightness of the screen is adjusted.

By employing this structure, according to the endoscope 101 of the present embodiment, not only is it possible to achieve the same effects as those of the first embodiment, but it is also possible to control the amount of illumination light from the LED 139 in conjunction with the amount of reflection light that is taken in, and the brightness of an image can be adjusted to a more appropriate brightness to correspond to the temperature around the LED 139.

Figure 30:
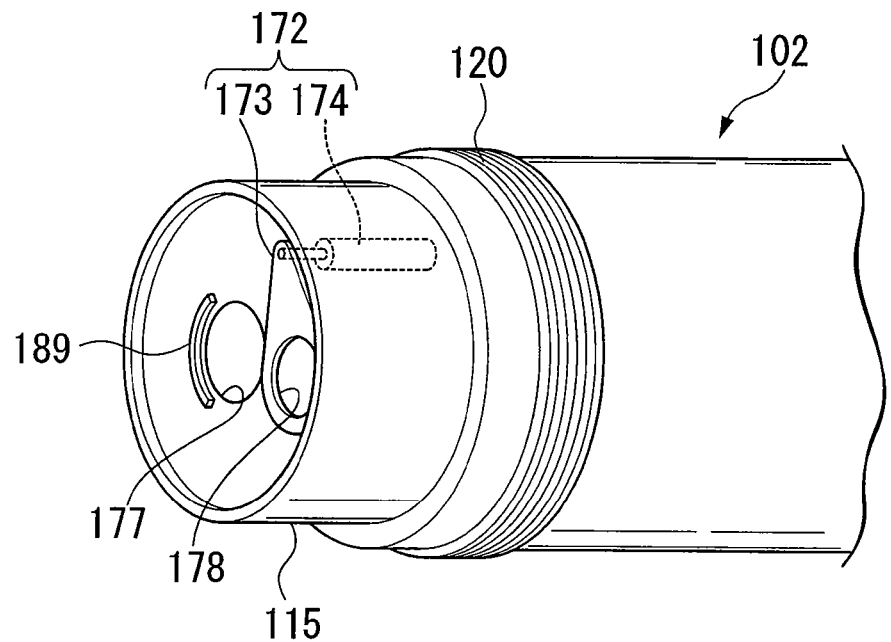
FIG. 30 is a perspective view showing a state when the diaphragm mechanism that is provided in the seventh embodiment of the endoscope of the present invention is installed in another location.
Figure 31:
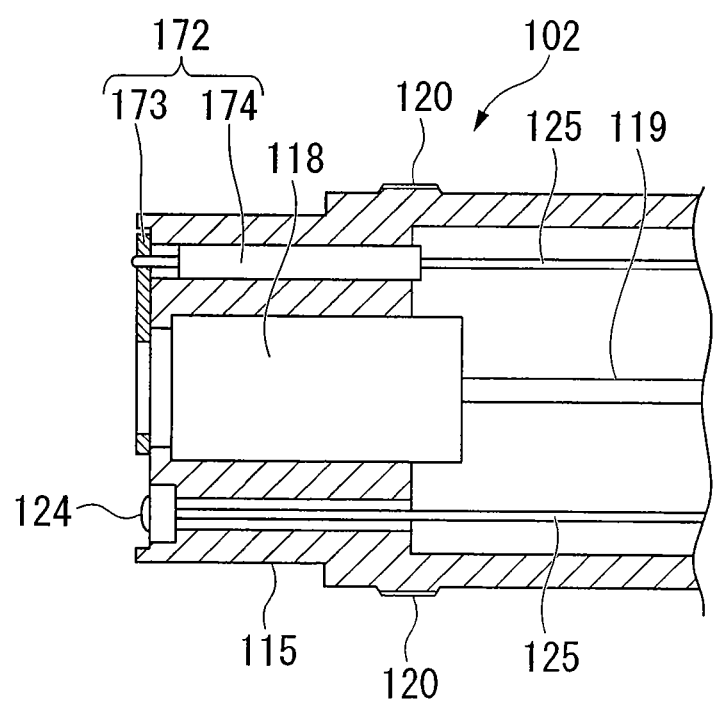
FIG. 31 is a side cross-sectional view of the insertion portion shown in FIG. 30.

Note that, in the present embodiment, the diaphragm mechanism 172 is provided in the optical adaptor 123, however, the present invention is not limited to this and, as is shown in FIG. 30 and FIG. 31, it may also be provided on the insertion portion 102 side.

Figure 32:
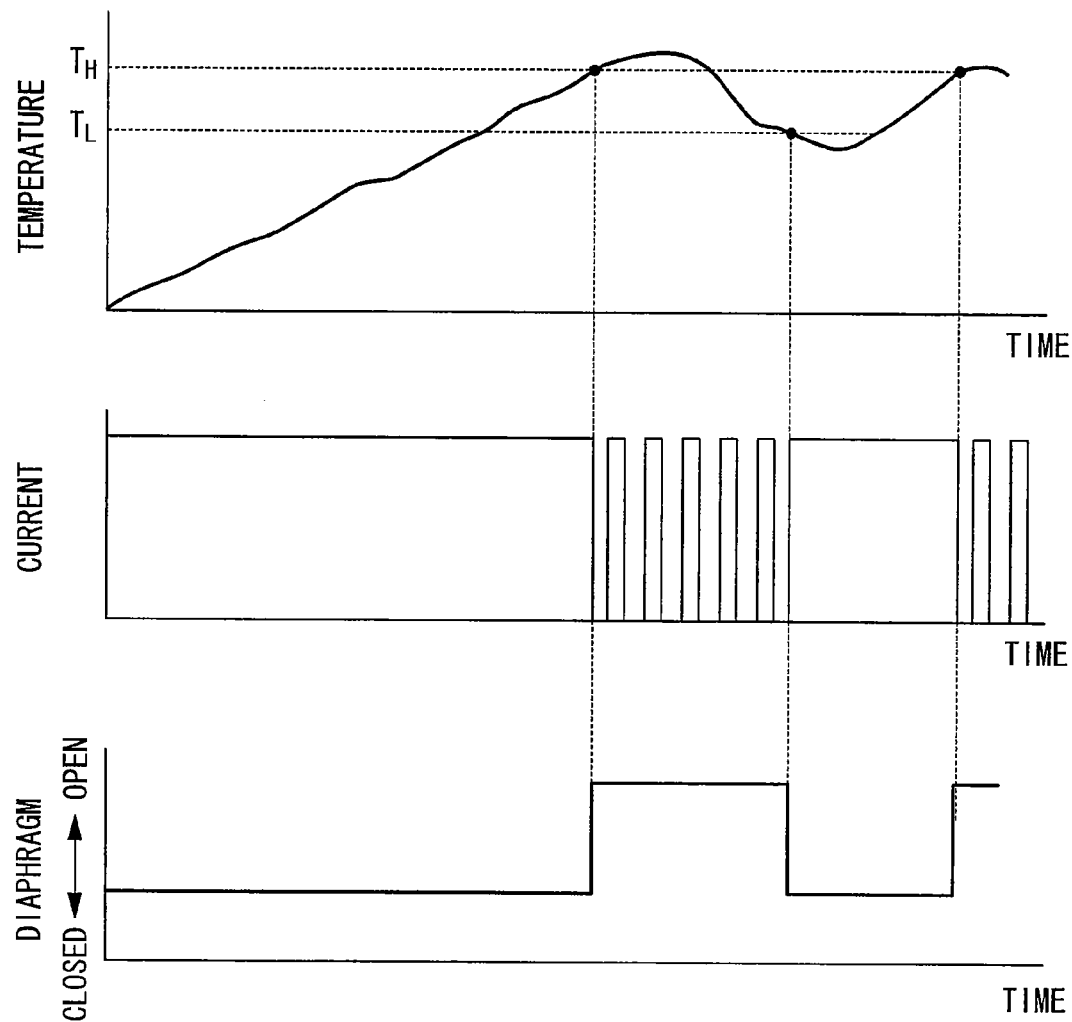
FIG. 32 is a variant example of the graph showing changes in the temperature around an LED, a state when the current value is switched, changes when a diaphragm is opened and closed, and changes in gain shown in FIG. 29, and is a graph showing a state when the current is switched to a pulse current.

Moreover, the current value of the current supplied from the LED power supply 153 is switched by the current control unit 163 between $I_H$ and $I_L$, however, the present invention is not limited to this and the device for altering brightness may be altered as is appropriate. For example, as is shown in FIG. 32, it is also possible to drive the LED 139 at first with stationary current and, when the temperature around the LED 139 increases to a threshold value $T_H$, to switch to a pulse current having a predetermined width. When the temperature then drops to a threshold value $T_L$, the current may then be switched back to a stationary current.

(Eighth Embodiment)

Figure 33:
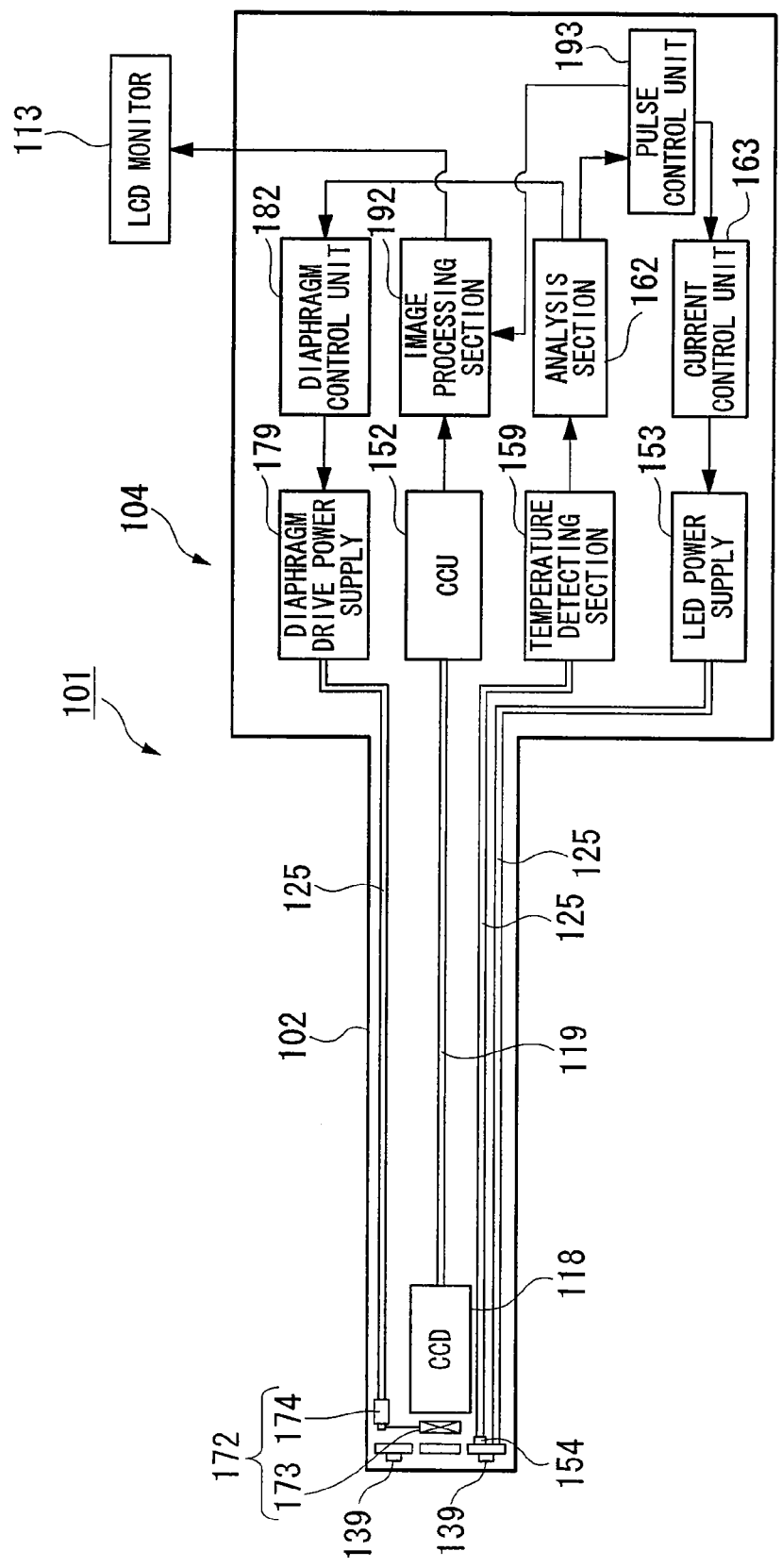
FIG. 33 is a block diagram for illustrating finctions of an eighth embodiment of the endoscope of the present invention.

The eighth embodiment of the present invention will now be described with reference made to FIG. 33.

In the present embodiment, the CCU 152 is electrically connected via an image processing section 192 to the LCD monitor 113. In addition, the analysis section 162 is connected via a pulse control unit 193 to the current control unit 163. Output signals from the pulse control unit 193 are input into the image processing section 192 and the current control unit 163.

Figure 34:
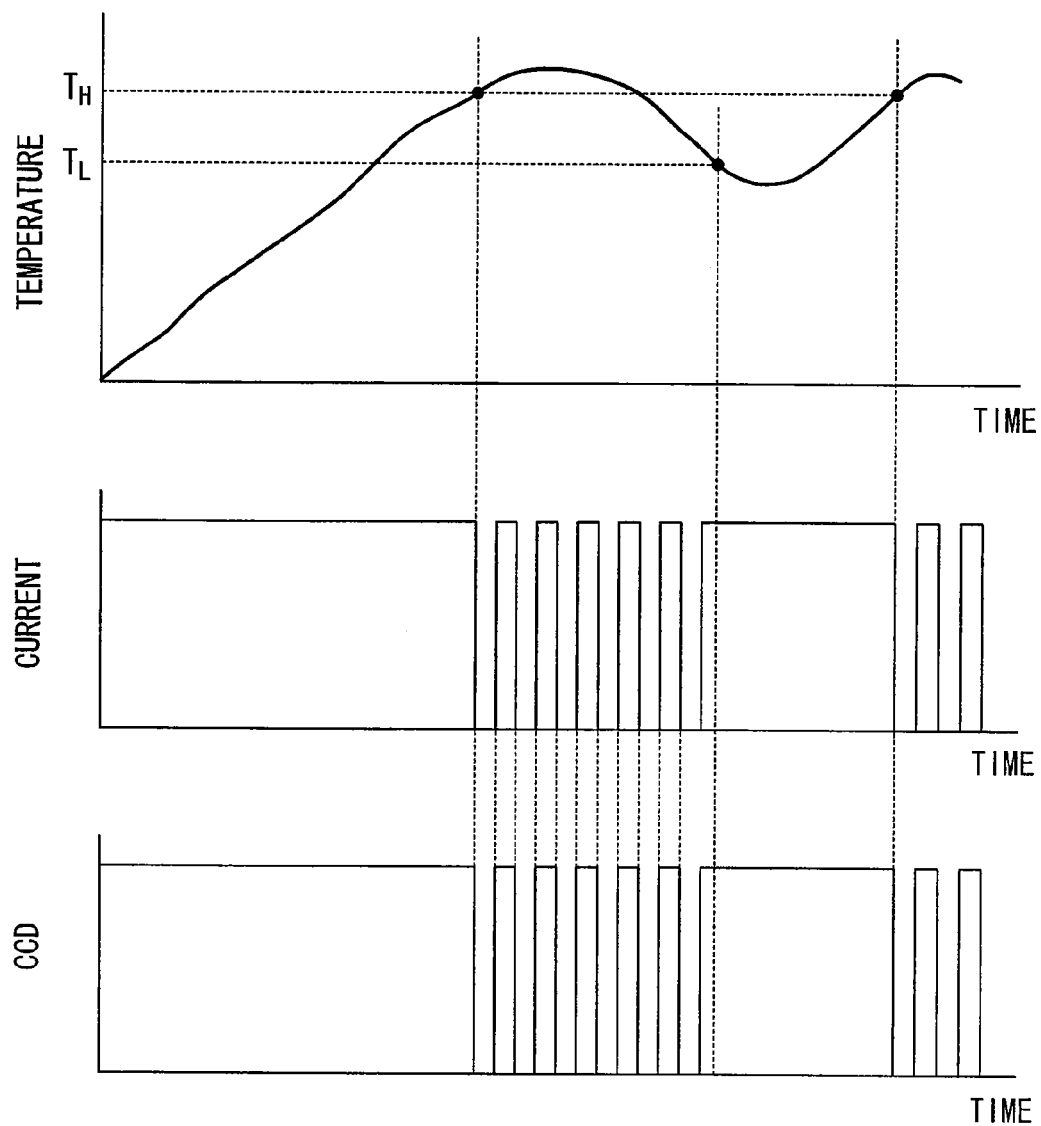
FIG. 34 is a graph showing changes in the temperature around an LED, a state when the current value is switched, and changes when a CCD is turned on and off in the eighth embodiment of the endoscope of the present invention.

Based on this structure, as is shown in FIG. 34, at first, stationary current is supplied from the LED power supply 153. During this time, image signals from the CCU 152 are supplied by the image processing section 192 unmodified to the LCD monitor 113. If the temperature around the LED 139 subsequently exceeds the threshold value $T_H$, a drive signal and a switching signal are output from the analysis section 162. In the same way as is described above, the drive signal is input into the diaphragm control unit 182 and the switching signal is input into the pulse control unit 193. The result of this is that the pulse control unit 193 outputs a pulse switching signal and a pulse fetching signal. The pulse switching signal is input into the pulse control unit 163, which causes the stationary current supplied from the LED power supply 153 to be switched to a pulse current having a predetermined width. In contrast, the pulse fetching signal is input into the image processing section 192. When this pulse fetching signal is input, the image processing section 192 fetches an image while the LED 139 is turned on. If the LED 139 is turned off, the image processing section 192 creates a switching image signal using the immediately prior still picture. The switching image signal is then supplied to the LCD monitor 113 and an observation image is displayed. The image at this time is an intermittent image due to a fetched image being displayed when the LED 139 is on and the immediately prior still picture being displayed when the LED 139 is off.

By employing this structure, according to the endoscope 101 of the present embodiment, not only is it possible to achieve the same effects as those of the second embodiment, but it is also possible to obtain a higher quality image with only a small amount of noise and the like.

(Ninth Embodiment)

Figure 35:
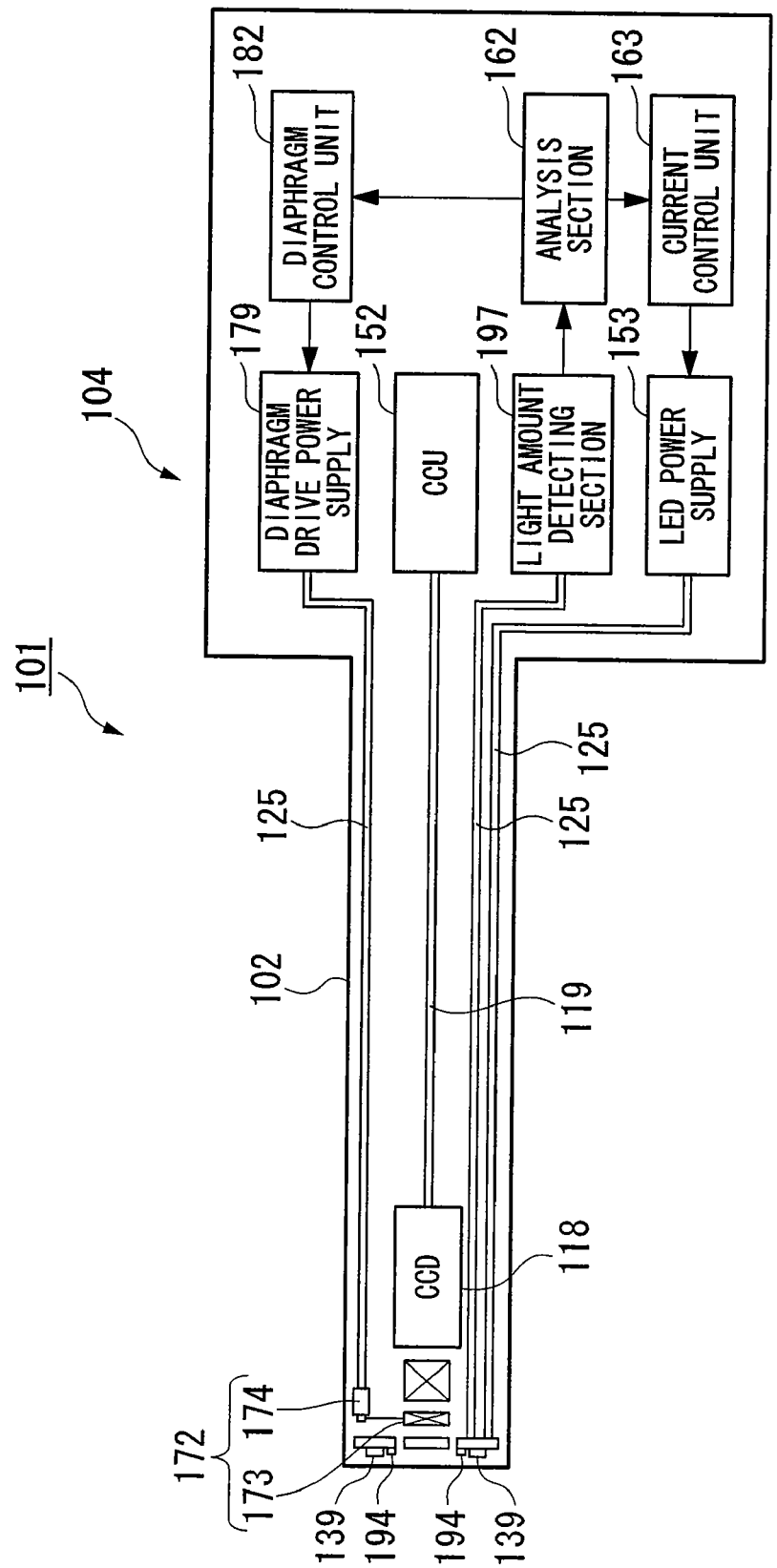
FIG. 35 is a block diagram for illustrating functions of a ninth embodiment of the endoscope of the present invention.

The ninth embodiment of the present invention will now be described with reference made to FIG. 35.

In the present embodiment, instead of the temperature sensor 154, a photo detector (PD) 194 is provided as a light amount sensor. The PD 194 is connected to a light amount detecting section (i.e., a detecting device) 197, and output signals from the light amount detecting section 197 are input into the analysis section 162.

Based on this structure, the amount of reflection light that is taken in is detected by the PD 194 and the light amount detecting section 197 and current having a pulse width corresponding to the results of this detection is supplied from the LED power supply 153.

By employing this structure, when the image displayed on the LCD monitor 113 is dark, the amount of illumination light that is irradiated from the LED 139 can be increased, while when the image is too bright, the amount of illumination light can be reduced. Accordingly, an image can be adjusted to the appropriate brightness in accordance with the amount of reflection light that is taken in, and a high quality image can be obtained easily and rapidly.

Figure 36:
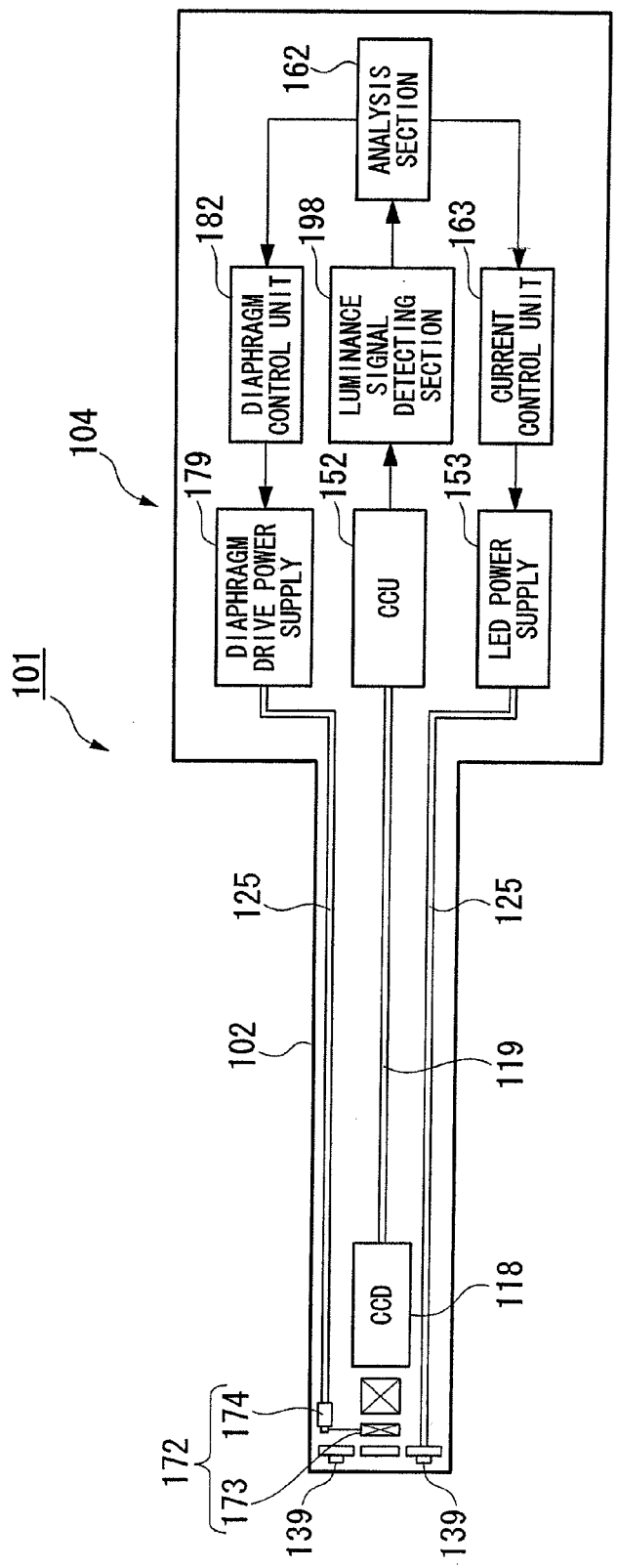
FIG. 36 is a block diagram showing a variant example of the ninth embodiment of the endoscope of the present invention.

Note that the PD 194 is provided in the present embodiment, however, instead of this, for example, as is shown in FIG. 36, it is also possible for the CCD 152 to be connected to the analysis section 162 via a luminance signal detecting section 198. The luminance signal detecting section 198 detects the amount of reflection light that is taken in from luminance signals from the CCU 152. The amount of illumination light irradiated from the LED 139 is then adjusted in accordance with the results of this detection. Note that, in this case, the CCD 118 functions as a light amount sensor.

(Tenth Embodiment)

Next, the tenth embodiment of the present invention will be described with reference made to FIGS. 37 and 38.

Figure 37:
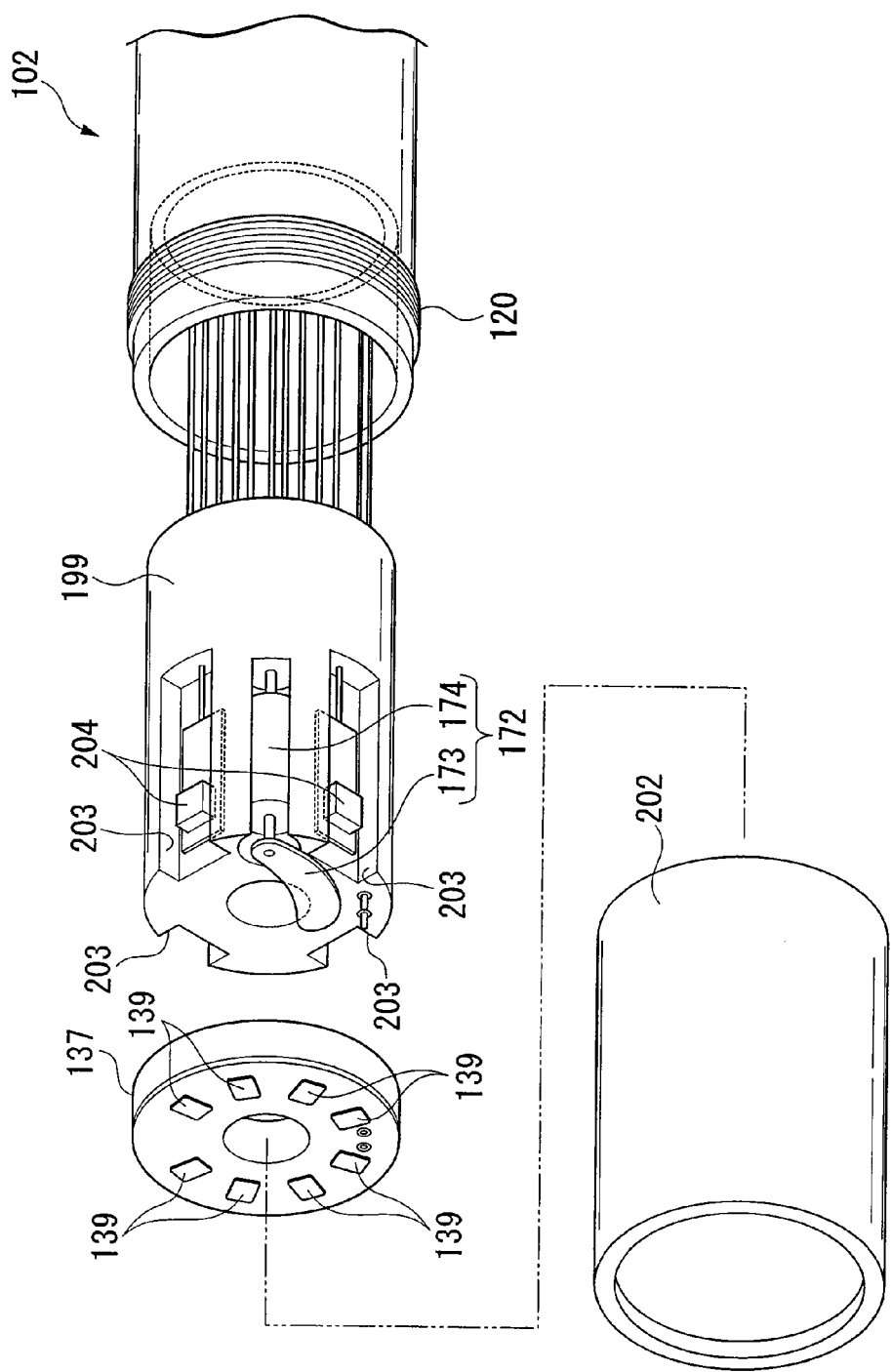
FIG. 37 is an exploded perspective view showing an insertion portion of a tenth embodiment of the endoscope of the present invention.
Figure 38:
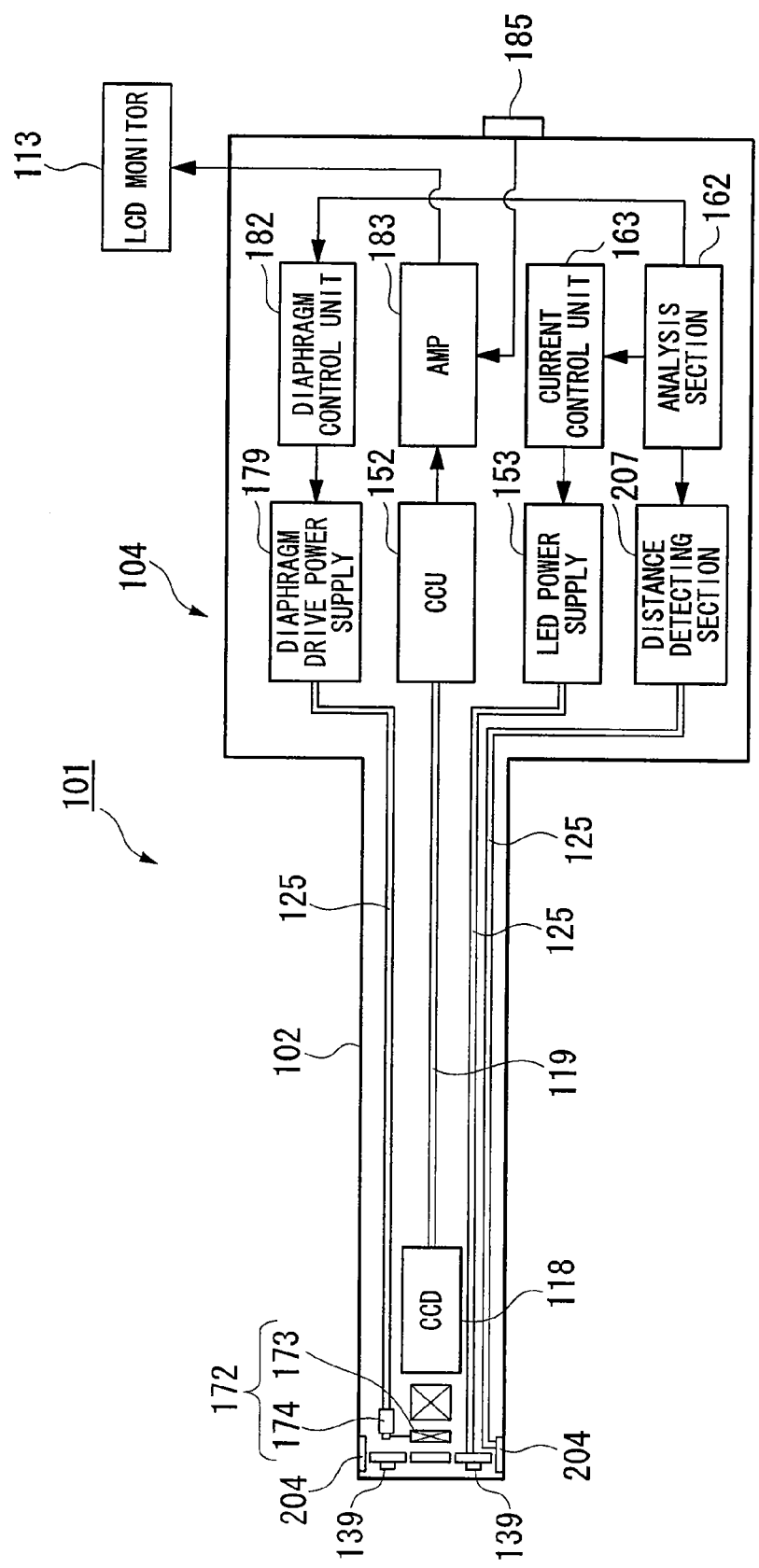
FIG. 38 is a block diagram for illustrating functions of the tenth embodiment of the endoscope of the present invention.

In the present embodiment, as is shown in FIG. 37, a substantially circular cylinder-shaped lens cylinder portion 199 is fitted into the distal end of the insertion portion 102, and an aluminum substrate 135 is provided at a front surface of the lens cylinder portion 199. In addition, a circular cylinder-shaped distal end outer cylinder portion 202 covers the distal end of the insertion portion 102.

Four concave portions 203 are formed spaced equidistantly from each other in the circumferential direction on a circumferential surface of the lens cylinder portion 199. A distance sensor (i.e., a detecting device) 204 that detects a distance from a detected object by generating an eddy current is provided in each one of the plurality of concave portions 203. Namely, four distance sensors 204 are provided spaced equidistantly from each other. As is shown in FIG. 38, these distance sensors 204 are electrically connected to a distance detecting section (i.e., a detecting device) 207. The distance detecting section is connected to an analysis section 162. Note that, as is shown in FIG. 37, the diaphragm section 173 is formed in a substantially crescent shape, and the amount of reflection light that is transmitted is precisely adjusted by precisely adjusting the position of the diaphragm portion 173.

Based on this structure, for example, when the insertion portion 102 is placed inside a pipe and the pipe is observed, the distance at four points from the insertion portion 102 to the inner circumferential surface of the pipe is calculated by the distance detecting section 207 and the four distance sensors 204. Based on the distance at these four points, the size of the pipe is calculated and the amount of illumination light from the LED 139 is adjusted in accordance with the size of the pipe.

By employing this structure, it is possible to easily and rapidly obtain images having an appropriate amount of light that corresponds to the size of the pipe.

Note that four distance sensors 204 are provided in the present embodiment, however, the present invention is not limited to these and the number of distance sensors 204 that are installed can be altered as is appropriate.

Moreover, the size of the pipe is calculated by the distance calculating section 207 and the distance sensors 204, however, the present invention is not limited to this and it is also possible to calculate the position of the insertion portion 102 inside the pipe. In addition, it is also possible to restrict the amount of light from the LED 139 that is placed on the side close to the inner circumferential surface of the pipe, and to increase the amount of light from the LED 139 that is placed on the side farthest from the inner circumferential surface. Furthermore, it is also possible to control the diaphragm control unit 182 in conjunction with the current control unit 163 by calculating the distance from an inspected object. For example, if the distance is close, then the amount of illumination light is increased and the diaphragm is made narrower. If, however, the distance is far, then the amount of illumination light is restricted and the diaphragm is opened.

By employing this structure, an image having the appropriate brightness in accordance with the distance can be obtained rapidly and easily.

Figure 39:
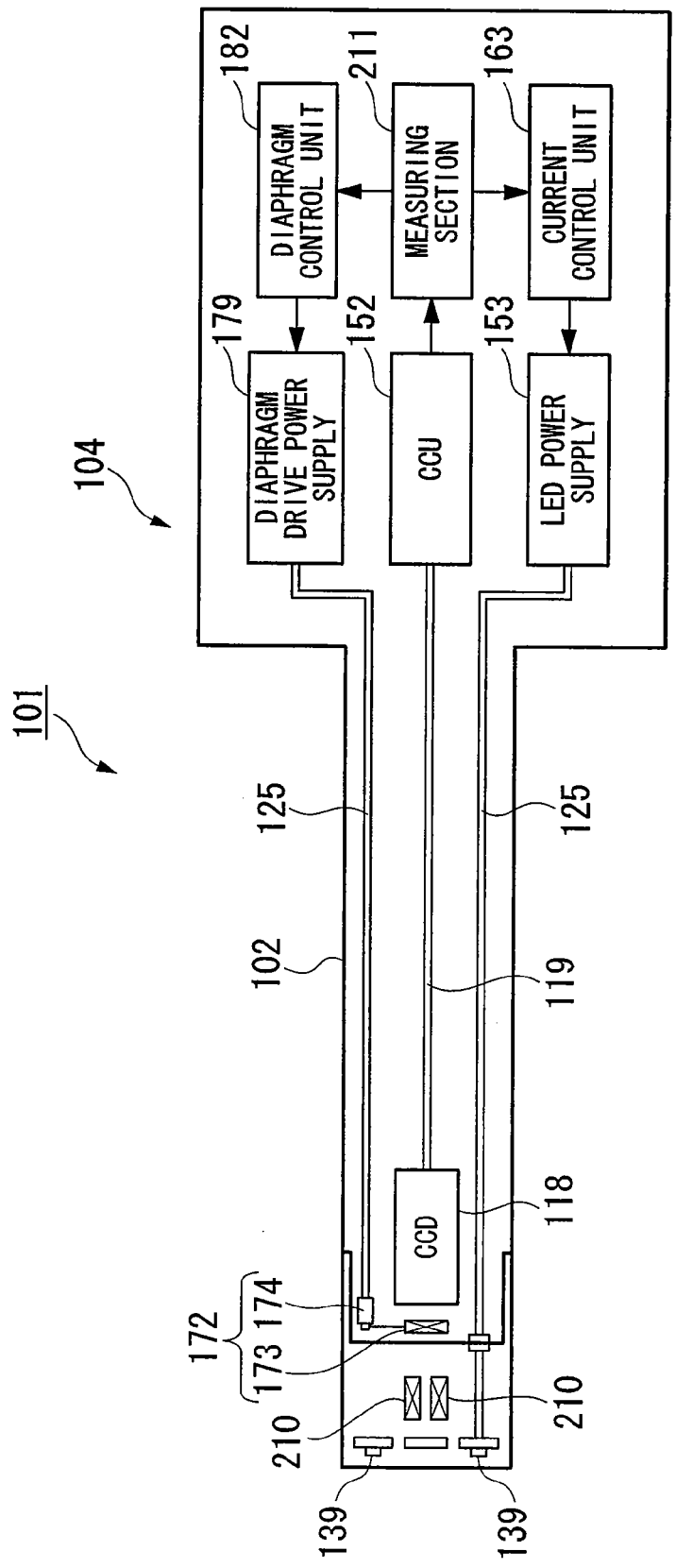
FIG. 39 is a block diagram showing a variant example of the tenth embodiment of the endoscope of the present invention.

Moreover, although the distance sensor 204 and the distance detecting section 207 are provided, instead of these, as is shown in FIG. 39, it is also possible to use an insertion portion 102 for stereo measurement that is provided with a plurality of subjective optical systems 210. In this case, the CCU 152 is electrically connected to a measuring section 211 and the measuring section 211 is connected to the current control unit 163 and the diaphragm control unit 182. On the basis of this structure, the distance to an inspected object can be calculated by the measuring section 211 using triangulation, and the brightness of the LED 139 as well as the diaphragm can be changed.

(Eleventh Embodiment)

Figure 40:
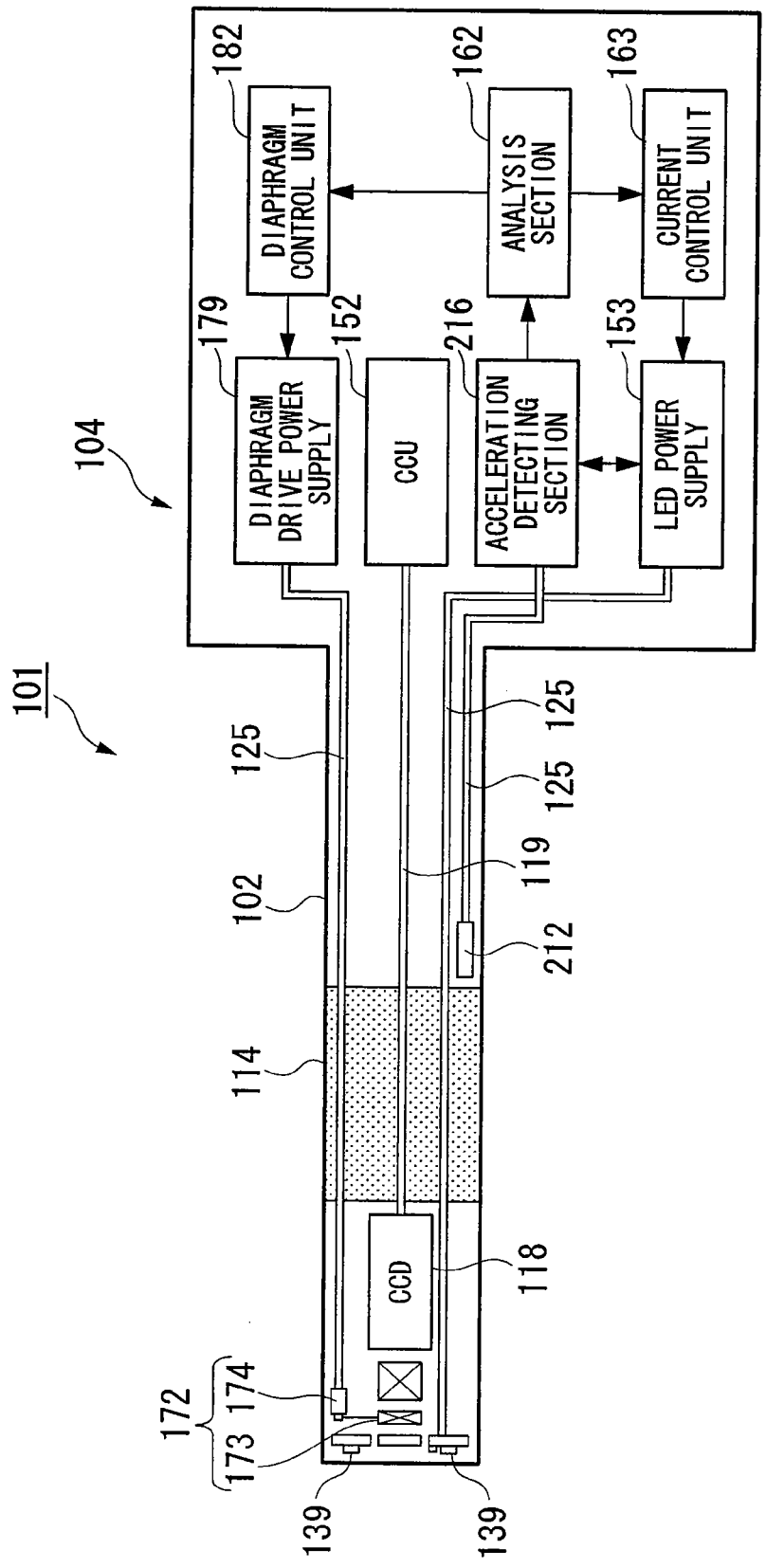
FIG. 40 is a block diagram for illustrating the respective functions of an eleventh embodiment of the endoscope of the present invention.

Next, the eleventh embodiment of the present invention will be described with reference made to FIG. 40.

The endoscope 101 of the present embodiment is provided with an acceleration sensor (i.e., a detecting device) 212 as a detecting device. The acceleration sensor 212 is provided in the insertion portion 102 in front of the bending portion 114. The acceleration sensor 212 is electrically connected to an acceleration detecting section (i.e., a detecting device) 216, and the acceleration detecting section 216 is electrically connected to the analysis section 162.

Here, when the insertion portion 102 is inserted into a pipe or the like and is fed forward, it is normal to observe the entire internal circumference of the pipe and to look for locations that need to be observed in detail such as scratches and cracks. In addition, when the insertion portion 102 is moving forward slowly, an operator is normally occupied with other tasks that do not require observation.

Figure 41:
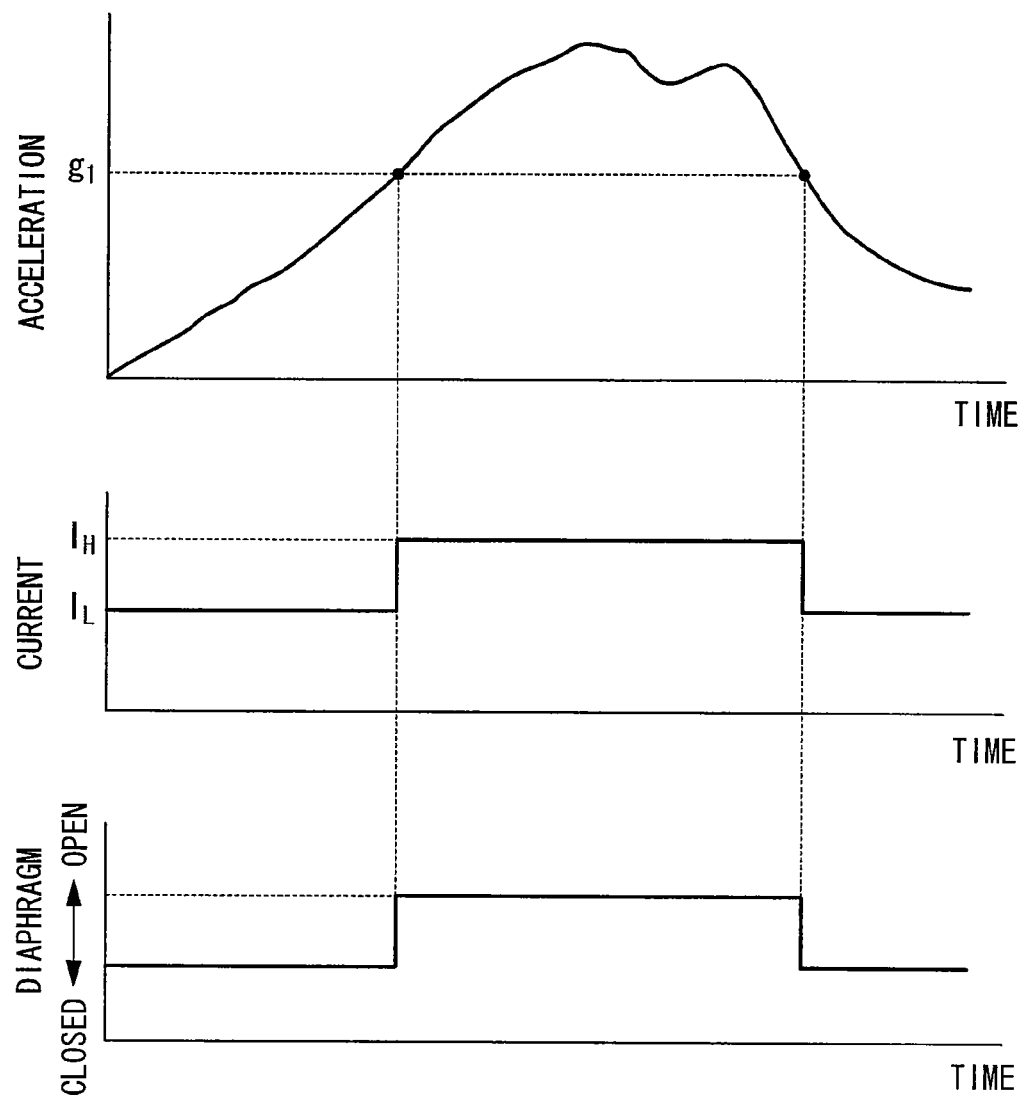
FIG. 41 is a graph showing changes in the rate of acceleration of an insertion portion, a state when the current value is switched, and changes when a diaphragm is opened and closed in the eleventh embodiment of the endoscope of the present invention.

In the present embodiment, the acceleration of the insertion portion 102 is detected by the acceleration sensor 212 and the acceleration detecting section 216, and the current control unit 163 is controlled in conjunction with the diaphragm control unit 182 in accordance with this acceleration. Specifically, as is shown in FIG. 41, when there is low acceleration, namely, when the insertion portion 102 is advancing slowly, the current that is supplied from the LED power supply 153 is the low level current value $I_L$, and the diaphragm is closed. As a result, power consumption is restricted. When the acceleration of the insertion portion 102 exceeds a threshold value $g_1$, namely, when the insertion portion is advancing quickly and the entirety of an object is being observed, the current that is supplied from the LED power supply 153 is switched to the high level current value IH and the diaphragm is opened. As a result, an image suitable for a full observation is obtained.

Note that when the insertion portion 102 is stopped and a scratch or the like is observed in detail, by turning on a switch (not shown) the amount of illumination light from the LED 139 is forcibly increased.

By employing the above structure, according to the endoscope 101 of the present embodiment, it is possible to easily and quickly obtain an image with an appropriate amount of light to correspond to the acceleration of the insertion portion 102.

Moreover, because the acceleration sensor 212 is provided in front of the bending portion 114, the acceleration of the distal end of the insertion portion 102 during the bending of the bending portion 114 is not detected so that the detection accuracy is improved.

(Twelfth Embodiment)

Figure 42:
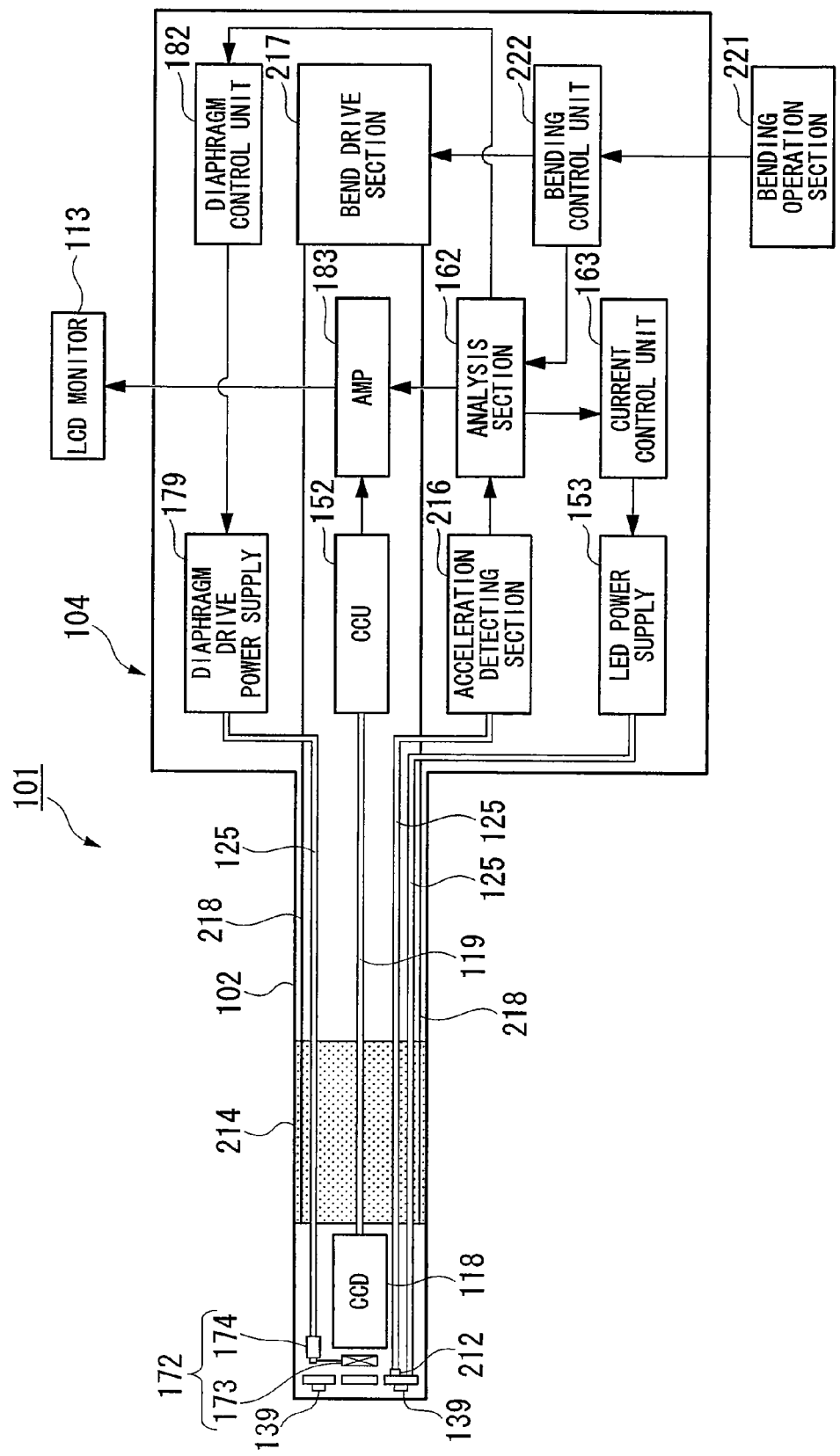
FIG. 42 is a block diagram for illustrating functions of a twelfth embodiment of the endoscope of the present invention.

Next, the twelfth embodiment of the present invention will be described with reference made to FIG. 42.

In the present embodiment, an acceleration sensor (for example, a three axis sensor) 212 is provided at a distal end portion of the insertion portion 102, and the movement when the insertion portion 102 is inserted in an axial direction as well as an operation to bend the bending portion 114 can both be detected. Moreover, the endoscope 101 is provided with a bending operation section 221 such as a joystick that causes the bending portion 114 to perform a bending operation. Output signals from the bending operation section 221 are input into a bending control unit 222. The bending control unit 222 is electrically connected to the analysis section 162 and to a bending drive section 217 that bends the bending portion via an angle wire 218.

On the basis of the above structure, when an insertion operation is performed, in the same way as is described above, the acceleration of the insertion portion 102 is detected. During the insertion operation, in order to perform a full observation, the current supplied to the LED 139 is set to the high level current value $I_H$ and the diaphragm is opened to the maximum as is shown in the "insertion operation" area in FIG. 43.

When the insertion portion 102 is stopped and the joystick is operated, a bending operation signal is output from the bending operation section 221 and is input into the bending control unit 222. When this bending operation signal is input, the bending control unit 222 outputs a detection command signal and a drive command signal. The detection command signal is input into the analysis section 162 while the drive command signal is input into the bending drive section 217. As a result, the bending section 114 is made to perform a bending operation by the bending drive section 217, and the acceleration during this bending is detected by the acceleration sensor 212 and the acceleration detecting section 216 and detection signals are input into the analysis section 162. Namely, by detecting bending operation signals from the bending operation section 221, the analysis section 162 analyses whether a bending operation is being performed or whether an insertion operation is being performed.

Figure 43:
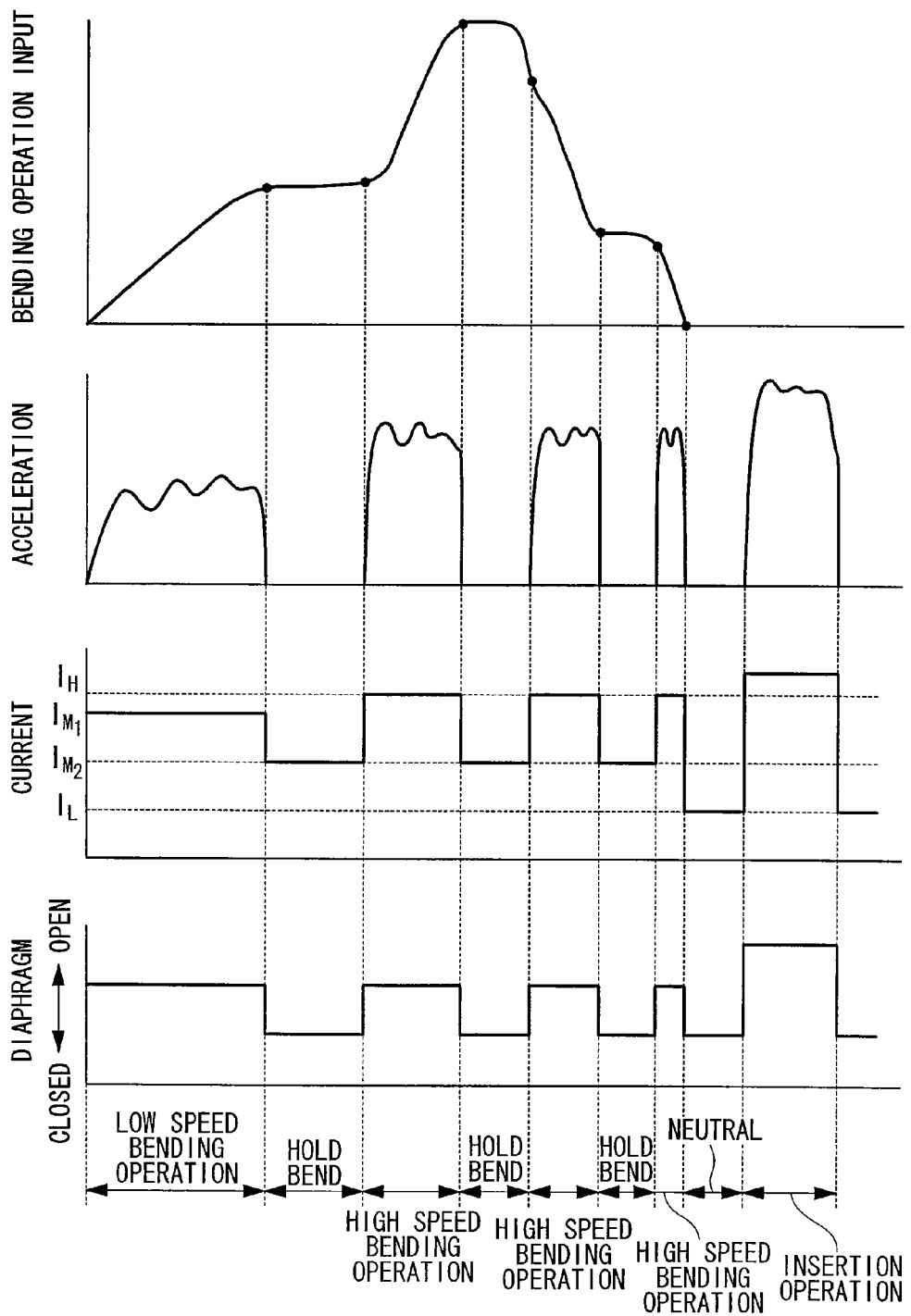
FIG. 43 is a graph showing changes in an input to perform a bend operation on an operation section, changes in the rate of acceleration of an insertion portion, a state when the current value is switched, and changes when a diaphragm is opened and closed in the twelfth embodiment of the endoscope of the present invention.

At this time, as is shown in the "Low speed bending operation" and "High speed bending operation" areas in FIG. 43, the current supplied to the LED 139 is adjusted to a current value $I_{M1}$, that is smaller than the high level current value $I_H$. In conjunction with this, the diaphragm is slightly closed. Namely, because scratches and cracks and the like are often observed in detail during a bending operation, the image quality is improved by increasing the brightness and slightly closing the diaphragm.

Furthermore, when a bend is held, as is shown in the "Hold bend" areas in FIG. 43, the current supplied to the LED 139 is set to a current value $I_{M2}$ that is even smaller than the current value $I_{M1}$, and the diaphragm is further closed.

When the insertion portion 102 is in a stopped state and the bending portion 114 is in a neutral state in which it is not bending, as is shown in the "Neutral" area in FIG. 43, the current supplied to the LED 139 is set to the low level current value $I_L$ that is even smaller than the current value $I_{M2}$. Namely, when the insertion portion 102 is in a neutral state, the brightness is left at a low level. At this time, it is also possible to increase the gain of the amp 183 by turning on a switch (not shown).

Note that it is also possible to change the proportions of the current supplied to the LED 139 and the opening angle of the diaphragm to correspond to the size of the object being examined.

By employing the above structure, during a bending operation the amount of light from the LED 139 is increased and the diaphragm is slightly closed. As a result, picture quality can be improved. In addition, during an insertion operation, in order to perform a full observation priority is given to brightness so as to make the image brighter even if the image quality consequently deteriorates slightly. Furthermore, when the insertion portion 102 is stopped, it is possible to keep the amount of light from the LED 139 as low as possible.

Accordingly, it is possible to quickly and easily obtain an image with an appropriate brightness that corresponds to the usage state of the insertion portion 102.

Note that it is also possible for the acceleration sensor 212 to be provided not in one location, but in two locations at both the front and rear of the bending portion 114. In this case, the front acceleration sensor 212 may be a two axis acceleration sensor that detects a bending operation of the bending portion 114, while the rear acceleration sensor 212 may be a single axis acceleration sensor that detects an insertion operation of the insertion portion 102.

(Thirteenth Embodiment)

Figure 44:
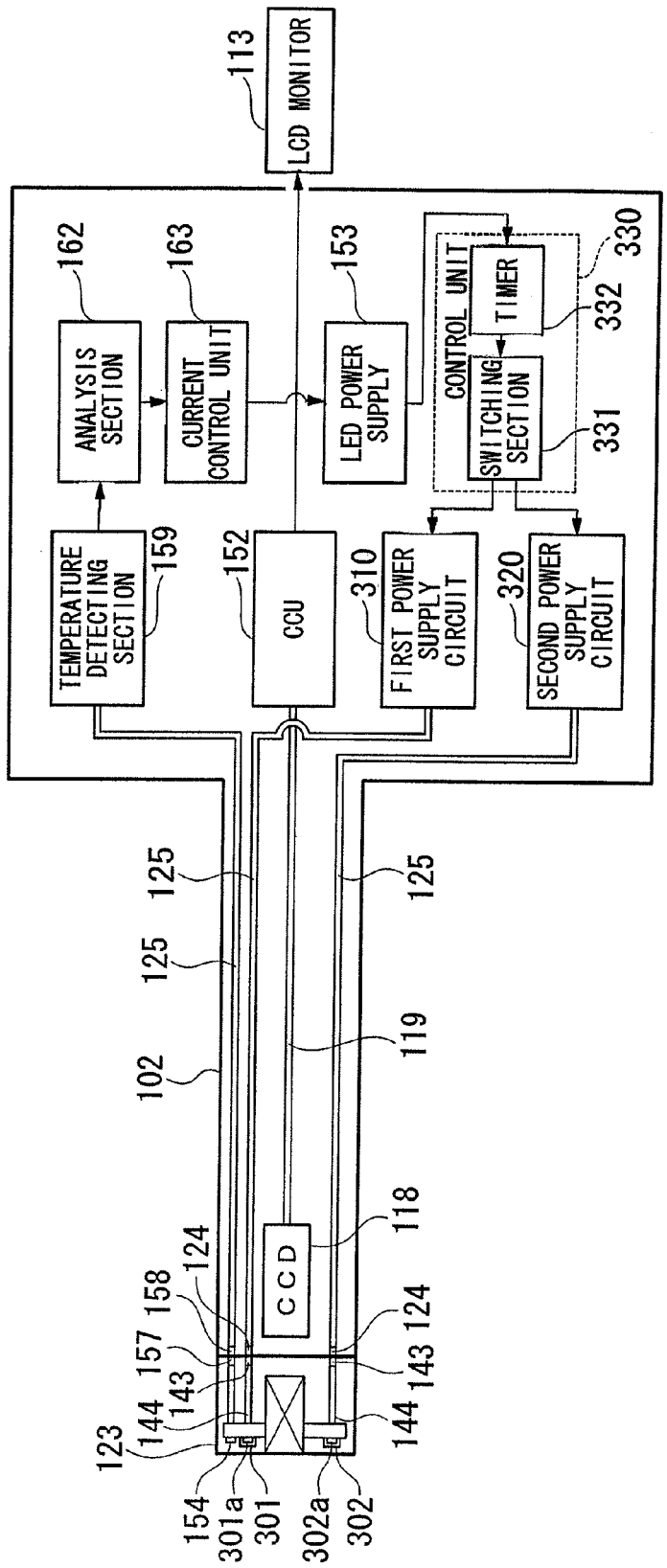
FIG. 44 is a block diagram for illustrating functions of a thirteenth embodiment of the endoscope of the present invention.

Next, the thirteenth embodiment of the present invention will be described with reference made to FIG. 44.

In the present embodiment, a first LED unit 301 and a second LED unit 302 are provided inside the optical adaptor 123. The first LED unit 301 is provided with a plurality of first LED chips 301a, and the second LED chip 302 is also provided with a plurality of second LED chips 302a.

The first LED unit 301 is connected to an adaptor side electrode terminal 143 via an electrode rod 144, and the second LED unit 302 is also connected to an adaptor side electrode terminal 143 via an electrode rod 144. The two adaptor side electrode terminals 143 are both exposed to the rear end surface of the optical adaptor 123.

When the optical adaptor 123 is fitted to the distal end of the insertion portion 102, the electrode rod 144 that is connected to the first LED unit 301 is connected to one insertion portion side electrode terminal 124 that is provided at a distal end surface of the insertion portion 102. The electrode rod 144 that is connected to the second LED unit 302 is connected to another insertion portion side electrode terminal 124 that is fitted to the distal end surface of the insertion portion 102.

The one insertion portion side electrode terminal 124 is connected via a cable 125 to a first power supply circuit (i.e., a constant current supply device) 310, while the other insertion portion side electrode terminal 124 is connected via a cable 125 to a second power supply circuit (i.e., a constant current supply device) 320. The first power supply circuit 310 and the second power supply circuit 320 are connected to a control unit 330. The control unit 330 is provided with a switching section 331 that is connected to the first power supply circuit 310 and the second power supply circuit 320, and with a timer 332 that outputs switching signals at regular time intervals.

Based on this structure, the first power supply circuit 310 and the second power supply circuit 320 are driven alternatingly at regular time intervals by the switching section 332 in accordance with switching signals from the timer 332.

In the endoscope 101 of the present embodiment, by causing the first LED chip 301a and the second LED chip 302a to alternatingly emit light, excessive heat generation from the first LED chip 301a and the second LED chip 302a is restricted.

When the first LED unit 301 and the second LED unit 302 are driven, the temperature around them rises, although this rise is gradual rather than abrupt. During this time, the temperature around the first LED unit 301 and the second LED unit 302 is detected by the temperature sensor 154 and the temperature detecting section 159, and detection signals therefrom are input into the analysis section 162. The analysis section 162 compares the temperature around the first LED unit 301 and the second LED unit 302 that are based on the detection signals with a high level threshold value $T_H$ that has been set in advance. When the temperature around the first LED unit 301 and the second LED unit 302 exceeds the threshold value $T_H$, the analysis section 162 outputs a switching signal. This switching signal is input into the current control unit 163 and the current from the LED power supply 153 is switched by the current control unit 163 from the high level current value $I_H$ to the low level current value $I_L$. As a result, the amount of light from the first LED unit 301 and the second LED unit 302 is reduced and the amount of generated heat is also reduced. In addition, by reducing the amount of heat that is generated from the first LED unit 301 and the second LED unit 302, the observation image that is displayed on the LCD monitor 113 is adjusted to an accurate image that has little noise and the like.

Furthermore, by reducing the amount of heat that is generated from the first LED unit 301 and the second LED unit 302, the temperature around the first LED unit 301 and the second LED unit 302 also becomes lower. When this temperature falls below the low level threshold value $T_L$, a switching signal is output from the analysis section 162 and the current from the LED power supply 153 is switched by the current control unit 163 to the high level current value $I_H$. By then repeating this series of operations the image displayed on the LCD monitor 113 is adjusted to a high quality image that has little noise and the like.

By employing the above structure, according to the endoscope 101 of the present embodiment, by causing the first LED chip 301a and the second LED chip 302a to emit light alternatingly, the heat generated by the first LED chip 301a and the second LED chip 302a is kept under control. As a result, it is possible to restrict the temperature inside the insertion portion 102 from rising. Furthermore, it is possible to accurately and easily adjust the brightness of an observation image displayed on the LCD monitor 113 in accordance with the temperature around the first LED unit 301 and the second LED unit 302.

Note that, in the above described sixth through thirteenth embodiments, the "usage environment" of the insertion portion 102 that is detected by the detecting device is taken as the temperature or amount of light, or as the size of the object being examined or the distance thereto, however, the present invention is not limited to this and the usage environment may be another environment such as pressure or the like.

In addition, the "usage state" of the insertion portion 102 detected by the detecting device is taken as acceleration, however, the present invention is not limited to this and it is also possible for the usage state to be another state such as speed, angle, rotational velocity or the like.

Moreover, the LED 139 is used as an illumination device, however, the present invention is not limited to this and it is also possible for the illumination device to be another type that uses a lamp or laser light.

Furthermore, the CCD 118 is used as an image pickup device, however, the present invention is not limited to this and it is also possible for another image pickup device to be used such as a C-MOS, an image guide fiber, or the like.

Moreover, the LCD monitor is used as a display device, however, the present invention is not limited to this and another type of monitor may be used.

In the above described embodiment a description is principally given of an industrial endoscope, however, the present invention is not limited to this and the present invention can also be applied to a medical endoscope.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as limited by the foregoing description and is only limited by the scope of the appended claims.

What is claimed is:

1. An endoscope that has an insertion portion that is inserted into an interior of an object and an image pickup device that is provided in the insertion portion, and that observes the interior of the object via the image pickup device, the endoscope comprising:

a first LED unit provided in the insertion portion and comprising an LED chip positioned and configured to irradiate light into the interior of the object;

a second LED unit provided in the insertion portion and comprising an LED chip positioned and configured to irradiate light into the interior of the object;

an alternating conduction control unit positioned and configured to conduct power alternatingly to the first LED unit and to the second LED unit;

an acceleration detecting device provided in the insertion portion and positioned and configured to detect a rate of acceleration of the insertion portion;

a simultaneous conduction control unit that conducts power simultaneously to the first LED unit and the second LED unit, and the driving of the alternating conduction control unit or the simultaneous conduction control unit is switched in accordance with an output from the acceleration detecting device; and a temperature detecting device configured to detect temperatures, wherein the first LED unit and the second LED unit are configured so as to have a substantially equal brightness, and the alternating conduction control unit is configured to switch conduction to the first LED unit or to the second LED unit when a detection signal from the temperature detecting device reaches a predetermined threshold value that has been set in advance.

2. The endoscope according to claim 1, wherein the alternating conduction control unit alternatingly switches power conduction between the first LED unit and the second LED unit at regular time intervals.

3. The endoscope according to claim 1, wherein the temperature detecting device is provided adjacent to the LED chip.

4. An endoscope that has an insertion portion that is inserted into an interior of an object and an image pickup device that is provided in the insertion portion, and that observes the interior of the object via the image pickup device, the endoscope comprising:
- a first LED unit that is provided in the insertion portion and has an LED chip positioned and configured to irradiate light into the interior of the object;
- a second LED unit that is provided in the insertion portion and has an LED chip positioned and configured to irradiate light into the interior of the object;
- an alternating conduction control unit positioned and configured to conduct power alternatingly to the first LED unit and to the second LED unit;
- an acceleration detecting device provided in the insertion portion and positioned and configured to detect a rate of acceleration of the insertion portion; and
- a simultaneous conduction control unit that conducts power simultaneously to the first LED unit and the second LED unit, and the driving of the alternating conduction control unit or the simultaneous conduction control unit is switched in accordance with an output from the acceleration detecting device.

5. The endoscope according to claim 1, wherein: the first LED unit is provided with a plurality of first LED chips; the second LED unit is provided with a plurality of second LED chips; and the first LED chips and the second LED chips are placed in the insertion portion so as to alternate in the circumferential direction of the insertion portion.

6. The endoscope according to claim 1, wherein there is further provided a constant current supply device that is provided in the first LED unit and the second LED unit, and that supplies current of a fixed magnitude.

7. An endoscope comprising:
- an insertion portion configured to inserted into an interior of an object;
- a first LED unit provided in the insertion portion and comprising an LED chip positioned and configured to irradiate light into the interior of the object;
- a second LED unit provided in the insertion portion and comprising an LED chip positioned and configured to irradiate light into the interior of the object;
- an alternating conduction control unit positioned and configured to conduct power alternatingly to the first LED unit and to the second LED unit;
- an acceleration detecting device provided in the insertion portion and positioned and configured to detect a rate of acceleration of the insertion portion;
- a simultaneous conduction control unit that conducts power simultaneously to the first LED unit and the second LED unit, and the driving of the alternating conduction control unit or the simultaneous conduction control unit is switched in accordance with an output from the acceleration detecting device;
- an image pickup device that is provided in the insertion portion;
- a display device that displays an image that has been picked up by the image pickup device;
- a detecting device that detects a usage environment or a usage state of the insertion portion;
- a brightness altering device that alters a brightness of an image that is displayed on the display device in accordance with a result of a detection by the detecting device, and
- a temperature detecting device positioned and configured to detect temperatures,
- wherein the first LED unit and the second LED unit are configured so as to have a substantially equal brightness, and the alternating conduction control unit is configured to switch conduction to the first LED unit or to the second LED unit when a detection signal from the temperature detecting device reaches a predetermined threshold value that has been set in advance.

* * * * *